(12) United States Patent
Reah et al.

(10) Patent No.: US 8,591,584 B2
(45) Date of Patent: Nov. 26, 2013

(54) TEXTILE-BASED PLATE IMPLANT AND RELATED METHODS

(75) Inventors: Christopher Reah, Taunton (GB); Peter Butcher, Wollaton (GB); Alan McLeod, Taunton (GB)

(73) Assignee: NuVasive, Inc., San Diego, CA (US)

( * ) Notice: Subject to any disclaimer, the term of this patent is extended or adjusted under 35 U.S.C. 154(b) by 1060 days.

(21) Appl. No.: 12/274,345

(22) Filed: Nov. 19, 2008

(65) Prior Publication Data

US 2009/0138082 A1    May 28, 2009

Related U.S. Application Data

(60) Provisional application No. 61/003,752, filed on Nov. 19, 2007, provisional application No. 61/009,465, filed on Dec. 28, 2007, provisional application No. 61/048,906, filed on Apr. 29, 2008.

(51) Int. Cl.
    *A61F 2/44*    (2006.01)
(52) U.S. Cl.
    USPC .......... 623/17.11; 623/13.2; 606/60; 606/151
(58) Field of Classification Search
    USPC .............. 623/13.19, 13.2, 17.11; 606/60, 191
    See application file for complete search history.

(56) References Cited

U.S. PATENT DOCUMENTS

| | | |
|---|---|---|
| 889,614 A | 6/1908 | Johnsen |
| 924,795 A | 6/1909 | Klemm et al. |
| 2,687,703 A | 8/1954 | Shotsky |
| 3,183,868 A | 5/1965 | Shotsky |
| 3,270,696 A | 9/1966 | Lowenstein |
| 3,859,941 A | 1/1975 | Krieger |
| 4,517,910 A | 5/1985 | Jalowsky |
| 4,776,851 A | 10/1988 | Bruchman et al. |
| 4,790,850 A | 12/1988 | Dunn et al. |
| 4,904,260 A | 2/1990 | Ray et al. |
| 4,946,377 A | 8/1990 | Kovach |
| 5,004,474 A | 4/1991 | Fronk et al. |
| 5,108,397 A | 4/1992 | White |
| 5,192,322 A | 3/1993 | Kock et al. |
| 5,540,703 A | 7/1996 | Barker, Jr. et al. |
| 5,571,189 A | 11/1996 | Kuslich |
| 5,794,555 A | 8/1998 | Kwang |
| 5,800,543 A | 9/1998 | McLeod et al. |
| 5,990,378 A | 11/1999 | Ellis |
| 6,033,429 A | 3/2000 | Magovern |

(Continued)

FOREIGN PATENT DOCUMENTS

| | | |
|---|---|---|
| EP | 0192949 A1 | 9/1986 |
| EP | 0260970 A2 | 3/1988 |

(Continued)

OTHER PUBLICATIONS

Extended European Search Report in corresponding European Application No. 09253647.4 dated Feb. 2, 2010.

*Primary Examiner* — Thomas J Sweet
*Assistant Examiner* — Christopher D Prone
(74) *Attorney, Agent, or Firm* — Jonathan Spangler; Heather Prado

(57) ABSTRACT

A textile-based plate implant (and related methods) that supports tissue ingrowth within the implanted implant structure and is suitable for use in a variety of surgical applications, including but not limited to anterior, posterior and lateral surgical approaches directed towards the lumbar, thoracic and cervical regions of the spine.

11 Claims, 36 Drawing Sheets

(56) References Cited

U.S. PATENT DOCUMENTS

| | | | |
|---|---|---|---|
| 6,093,205 | A | 7/2000 | McLeod et al. |
| 6,248,106 | B1 | 6/2001 | Ferree |
| 6,263,817 | B1 | 7/2001 | Tajima et al. |
| 6,283,998 | B1 | 9/2001 | Eaton |
| 6,368,326 | B1 | 4/2002 | Dakin et al. |
| 6,416,776 | B1 | 7/2002 | Shamie |
| 6,419,704 | B1 | 7/2002 | Ferree |
| 6,428,544 | B1 | 8/2002 | Ralph et al. |
| 6,592,625 | B2 | 7/2003 | Cauthen |
| 6,620,196 | B1 | 9/2003 | Trieu |
| 6,712,853 | B2 | 3/2004 | Kuslich |
| 6,746,485 | B1 | 6/2004 | Zucherman et al. |
| 6,893,466 | B2 | 5/2005 | Trieu |
| 7,156,848 | B2 | 1/2007 | Ferree |
| 7,214,225 | B2 | 5/2007 | Ellis et al. |
| 7,229,441 | B2 | 6/2007 | Trieu et al. |
| 7,338,531 | B2 | 3/2008 | Ellis et al. |
| 7,601,166 | B2 | 10/2009 | Biedermann et al. |
| 7,655,044 | B2 | 2/2010 | Kwak |
| 7,713,463 | B1 | 5/2010 | Reah et al. |
| 7,828,855 | B2 | 11/2010 | Ellis et al. |
| 7,942,104 | B2 | 5/2011 | Butcher et al. |
| 7,946,236 | B2 * | 5/2011 | Butcher ................... 112/475.18 |
| 2001/0027319 | A1 | 10/2001 | Ferree |
| 2003/0074075 | A1 | 4/2003 | Thomas, Jr. et al. |
| 2003/0078579 | A1 | 4/2003 | Ferree |
| 2004/0015166 | A1 | 1/2004 | Gorek |
| 2004/0078089 | A1 | 4/2004 | Ellis et al. |
| 2004/0113801 | A1 | 6/2004 | Gustafson et al. |
| 2004/0186573 | A1 | 9/2004 | Ferree |
| 2006/0179652 | A1 | 8/2006 | Petersen et al. |
| 2007/0005062 | A1 | 1/2007 | Lange et al. |
| 2007/0073293 | A1 | 3/2007 | Martz et al. |
| 2007/0204783 | A1 | 9/2007 | Chong |
| 2007/0239158 | A1 | 10/2007 | Trieu et al. |
| 2007/0276490 | A1 | 11/2007 | Mateyka |
| 2007/0276494 | A1 | 11/2007 | Ferree |
| 2008/0015697 | A1 | 1/2008 | McLeod et al. |
| 2008/0147098 | A1 * | 6/2008 | Trieu ........................ 606/151 |
| 2008/0173223 | A1 | 7/2008 | Butcher et al. |
| 2008/0178786 | A1 | 7/2008 | Butcher et al. |
| 2008/0234753 | A1 | 9/2008 | Trieu |
| 2009/0131984 | A1 | 5/2009 | Linares |
| 2009/0138082 | A1 | 5/2009 | Reah et al. |

FOREIGN PATENT DOCUMENTS

| | | | |
|---|---|---|---|
| EP | 0314412 A1 | 5/1989 | |
| EP | 0599419 A2 | 6/1994 | |
| EP | 0744165 B1 | 2/2003 | |
| EP | 0744162 B1 | 5/2003 | |
| EP | 2189123 A1 | 5/2005 | |
| FR | 269338 A1 | 4/1994 | |
| FR | 2710520 A1 | 4/1995 | |
| FR | 2929101 A1 | 10/2009 | |
| GB | 2276823 A | 10/1992 | |
| WO | WO 90/11735 A1 | 10/1990 | |
| WO | WO 92/03988 A1 | 3/1992 | |
| WO | WO 92/10982 A1 | 7/1992 | |
| WO | WO 99/37242 A1 | 7/1999 | |
| WO | WO 01/21246 A1 | 3/2001 | |
| WO | WO 01/30269 A1 | 5/2001 | |
| WO | WO 02/30306 A1 | 4/2002 | |
| WO | WO 02/30324 A1 | 4/2002 | |
| WO | WO 2004/002374 A1 | 1/2004 | |
| WO | WO 2005/092211 A1 | 10/2005 | |
| WO | WO 2005/092247 A1 | 10/2005 | |
| WO | WO 2005/092248 A1 | 10/2005 | |
| WO | WO 2006/133130 A2 | 12/2006 | |
| WO | WO 2007/012070 A2 | 1/2007 | |

* cited by examiner

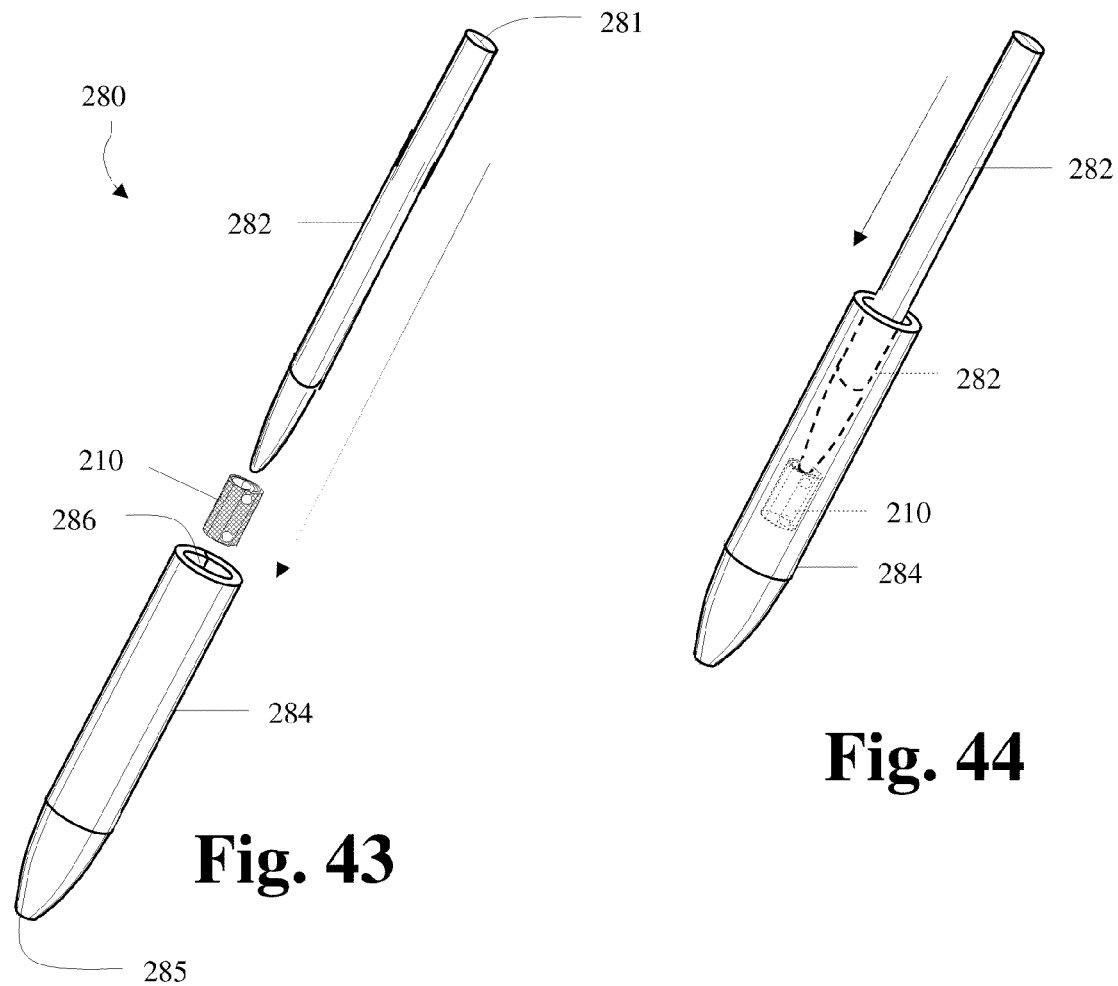
Fig. 43
Fig. 44
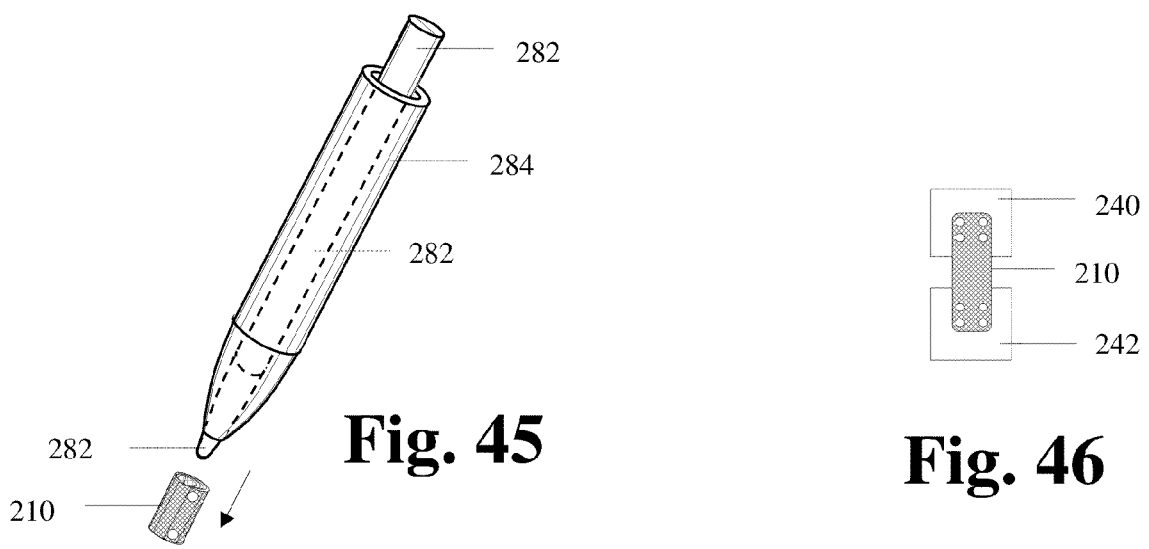
Fig. 45
Fig. 46

TEXTILE-BASED PLATE IMPLANT AND RELATED METHODS

CROSS REFERENCES TO RELATED APPLICATIONS

The present application is a non-provisional patent application claiming the benefit of priority under 35 USC 119(e) from U.S. Provisional Application Ser. No. 61/003,752, filed on Nov. 19, 2007, U.S. Provisional Application Ser. No. 61/009,465, filed on Dec. 28, 2007, and U.S. Provisional Application Ser. No. 61/048,906, filed on Jul. 1, 2008, the entire contents of which are hereby expressly incorporated by reference into this disclosure as if set forth fully herein. The present application also incorporates by reference the following documents into this disclosure in their entireties: U.S. Pat. No. 7,338,531, issued Mar. 4, 2008 and entitled "Textile Prosthesis;" U.S. Pat. No. 7,214,225, issued May 8, 2007 and entitled "Connector;" and U.S. patent application Ser. No. 11/968,157, filed Dec. 31, 2007 and entitled "Using Zigzags to Create Three-Dimensional Embroidered Structures."

BACKGROUND OF THE INVENTION

I. Field of the Invention

The present invention relates to implants and methods generally aimed at surgery and, more particularly, to implants and methods aimed at safely repairing and/or reconstructing affected skeletal structures.

II. Discussion of the Prior Art

Each year millions of people suffer from back pain arising from defects in the intervertebral disc space. The affected vertebrae generally create pain through compression of neural tissues as they move through a range of motion, or alternatively can result from permanent vertebral impingement against neural tissues. Movement-generated pain is generally treated by applying techniques to immobilize affected vertebrae in an orientation which prevents neural impingement. Commonly, surgical interventions directed at promoting fusion across the affected joint are employed to permanently provide long term pain relief to the patient. Thus current therapies include the steps of orienting affected structures in a preferred alignment, and then preserving the constructed alignment through the use of static devices which attach to the affected and surrounding tissues. The most commonly applied static devices include rigid plate assemblies, rod and screw assemblies, cages and fusion techniques, each of which have proven effective to immobilize of affected vertebral tissues.

Plate implants have been used for more than 40 years to aid in the promotion of fusion across affected vertebral disc spaces through stabilization of the joint. Early plate designs comprise static plates, generally comprised of metals, attached to the vertebral bodies adjacent to the affected disc space with screws inserted into the adjacent ostial tissues. These early plate designs were directed at complete immobilization of the affected joint while affording the optional benefit of concomitantly restricting fusion inducing materials such as bone grafts within said joint. While generally effective and accepted, the advent of modern material advancements afforded manufacturers the ability to provide alternative implant designs offering reduced plate profiles including any number of range limiting characteristics.

Although in many cases complete joint immobilization is preferred, in certain instances surgeons prefer to allow for retention of some limited mobility across the affected joint during the course of post operative fusion. As a result, some plate designs have incorporated elements which afforded limited motion across the affected joint. These plates generally restrict articular movements to flexional translational motion through the use of slideable housings traveling over rods incorporated into the plate. While successfully implemented and widely used, these devices generally afforded limited mobility only with a commensurate trade-off of implanting a higher profile device.

Currently a gap exists in the present state of plate technology in which an extremely low profile device providing limited flexibility across the intended receiving joint while providing physical characteristics which promote optimal tissue ingrowth within the device would reside.

The current invention overcomes the shortcomings of the prior art by providing a low profile textile based plate which restricts spinal extension while providing for greater mobility across the affected joint. Furthermore, the textile based plate structure promotes fusion within the lattice work of the appliance, thereby providing an exceptionally low, "encapsulated" profiled implant.

At times it may be advantageous to have a generally three-dimensional embroidered structure rather than a generally two-dimensional embroidered structure, but the processes by which three-dimensional embroidered structures may be formed have been complicated and not conducive to cost effective and repeatable mass production.

The first type of process for creating three-dimensional embroidered structures has been to build up the structural shape of the embroidered structure with layer upon layer of embroidered thread. The drawbacks to this technique are that it makes the embroidered structure thicker where the building up had been done. The building up only yields block-type structures and does not allow for the embroidering of curvatures.

A second process of manufacturing three-dimensional embroidered structures takes two or more generally flat embroidered structures and stitches them together such that they form a three-dimensional structure. While preserving the uniform thickness of the embroidered structures lost by the layering technique above and allowing for the simplicity of embroidering each flat section in two-dimensions, this process requires several stitching steps, that would typically be performed manually, which must be done three-dimensionally after the embroidering of the sections is completed. This process is costly, with repeatability concerns where the final results and dimensions will be subject to the skill and dexterity of the individual who performs the stitching.

A third known process creates a single, generally two-dimensional embroidered structure which may be folded such that the edge or edges of the structure meet and may be stitched together, again typically by a manual process, to form a three-dimensional structure. However, this process suffers from the same post-embroidering stitching steps in three-dimensions as the second process, and thus suffers from the same drawbacks.

SUMMARY OF THE INVENTION

According to one broad aspect of the present invention, a textile-based plate implant is provided that supports tissue ingrowth within the implanted appliance structure while limiting certain types of motion (e.g. flexion and/or extension). An implant according to the present invention is suitable for use in a variety of surgical applications, including but not limited to anterior, posterior and lateral surgical approaches directed towards the lumbar, thoracic and cervical regions of the spine. The compliant nature of the implant provides the required flexibility to support a range of physiological movements, as opposed to a completely static fusion surgery. In addition, the porosity and biocompatibility of the implant structure facilitates tissue ingrowth throughout part or all of the implant (as desired), which helps to secure and encapsulate a previously inserted complimentary implant within the affected joint, and enhance the promotion of bony fusion across the affected joint.

The implant of the present invention may have other useful purposes, such as for example ligament repair after insertion of a spinal implant. For example, after anterior spinal fusion surgery, it may be desirable or necessary to repair the anterior longitudinal ligament (ALL) to limit extension across the affected disc space. In such a case, the implant of the present invention would be fixed to adjacent vertebrae whilst spanning the fused disc space. The implant of the present invention also has the advantage of helping to maintain a bone graft or fusion cage within the disc space after implantation. This is especially true for lateral applications, since the major spinal ligaments would generally remain intact.

The implant of the present invention may be constructed in any number of suitable fashions without departing from the scope of the present invention. Generally the implant of the present invention comprises a network of load bearing filaments supported by a complex of stabilization, filler and aperture reinforcing filaments which together form a porous, flexible, lattice like structure. To secure fixation of the implant to receiving tissues, the implant also includes a plurality of apertures through which various types of fixation devices may be inserted into receiving.

The implant may be constructed from any of a variety of textile materials, for example including but not limited to (and by way of example only) permanent or resorbable polyester fiber, polypropylene, polyethylene, ultra high molecular weight polyethylene (UHMWPe), poly-ether-ether-ketone (PEEK), carbon fiber, glass, glass fiber, polyaramide, metal, copolymers, polyglycolic acid, polylactic acid, biodegradable fibers, silk, cellulosic and polycaprolactone fibers, aramid fibers or alginate fibers and the like. The implant may be manufactured using any number of textile processing techniques, for example including but not limited to embroidery, weaving, three-dimensional weaving, knitting, three-dimensional knitting, injection molding, compression molding, and cutting woven or knitted fabrics. In a preferred embodiment described herein, formation of the lattice like structure involves embroidery various types of filaments, including load bearing filaments, stabilization filaments and filler filaments into a dissolvable or permanent backing fabric in a predetermined pattern. Once completed, the embroidered design is isolated through dissolution of the backing material, thus providing an implant composed solely of the "freed" embroidered filaments.

It should be understood that "filament" as used herein is synonymous and interchangeable with "thread." Similarly, "substrate," "backing material," and "backing sheet" are also interchangeable terms as used herein. Furthermore, "backing thread" and "bobbin thread" are synonymous terms as used herein.

A general process of embroidering a textile implant is shown and described in U.S. Pat. No. 7,338,531, issued Mar. 4, 2008 and entitled "Textile Prosthesis," and U.S. Pat. No. 7,214,225, issued May 8, 2007 and entitled "Connector," the complete disclosures of which are hereby incorporated by reference in their entireties as if set forth fully herein. On a dissolvable substrate, a plurality of parallel, stationary backing threads are placed and secured on one surface (e.g. "backing surface"). On the opposing surface of the substrate (e.g. "stitching surface") is a plurality of stitching threads with one-to-one correspondence to the backing threads. Stitching may be done between one pair of threads at a time or in simultaneous multiplicity, as is described below.

The plurality of stitching threads from the stitching surface are passed through openings created in the dissolvable substrate by the passing of each individual thread to the backing surface. Each stitching thread is then looped over its corresponding backing thread, in essence picking up the backing thread and forming a lock stitch. Once each stitching thread has picked up its corresponding backing thread, the plurality of stitching threads are passed from the backing surface to the stitching surface through the openings in the dissolvable substrate created during the passage to the backing surface. The lock stitches prevent the stitching threads from completely pulling back out of the openings created in the dissolvable substrate. The plurality of stitching threads is then moved to a new stitching site and the process repeats until all the backing threads are joined by lock stitches to the corresponding stitching threads, creating a plurality of thread pairs.

A plurality of thread pairs may be enclosed by one or more pluralities of enclosing thread pairs. To enclose a plurality of thread pairs, a plurality of enclosing backing threads are placed and secured on the backing surface of a dissolvable substrate already holding at least one plurality of thread pairs, such that the plurality of enclosing backing threads covers the previously stitched plurality of backing threads. A plurality of enclosing backing threads is usually not parallel with the previous plurality of backing and stitching threads. A plurality of enclosing stitching threads, with one-to-one correspondence to the plurality of enclosing backing threads, are then stitched to the plurality of enclosing backing threads by the stitching process described above.

When the enclosing backing threads are all joined to the enclosing stitching threads by lock stitches, a plurality of enclosing thread pairs has been formed. This process may be repeated by stitching even more pluralities of enclosing thread pairs over all the previously stitched thread pairs, such that the first plurality is enclosed by the second plurality, which is enclosed by a third plurality, which is enclosed by a fourth plurality, etc. This process produces stable embroidered structures which do not unstitch into a pile of threads when the dissolvable substrate is removed.

The process of dissolvable substrate removal is dependent upon the composition of the dissolvable substrate material. Substrate materials are chosen such that the dissolution process which removes the dissolvable substrate will minimally, if at all, affect the physical properties of the remaining embroidered structure. The embroidered structure remains intact despite the removal of the dissolvable substrate because each stitching thread is stitched to its corresponding backing thread and vice versa. The backing thread is enclosed in one or more pluralities of enclosing thread pairs, which provides structural support.

Multiple fixation apertures are included within the implant matrix to exact fixation of the device to receiving tissues. The fixation apertures generally comprise reinforcing filaments stitched around load bearing filaments which generally define the aperture outline. The aperture reinforcing filaments may also extend at varying distances extending away from the aperture border so as to engage various filaments throughout the implant to provide optimal load sharing characteristics and structural integrity to the aperture and implant as a whole. The flexible nature of the aperture borders allows for insertion of fixation devices therethrough at any angle required by the physician in order to achieve optimal fixation device purchase within a receiving tissue. Additionally, the flexible nature of the aperture border allows for the insertion of fixation devices of differing shapes and dimensions without a requisite reconfiguration of aperture dimension.

The load bearing filaments of the present invention provide the major source of load bearing strength required by the implant to preferentially limit extension across the affected joint. Therefore, the load bearing filaments extend between and at least partially around the apertures, and ultimately transfer any encountered in situ loads to the fixation devices positioned therein and ultimately to their receiving tissues. Although shown and described herein as a "load bearing filament" in the singular, it should be understood (in light of the above discussion of the embroidery process) that each load bearing filament comprises at least a pair of threads (e.g. a stitching thread and a bobbin thread) embroidered on either side of the backing material. Once the backing material is dissolved away, the thread pair made up of the stitching and bobbin threads remains as a "load bearing filament." This understanding also applies to the support filaments, border filaments stabilization filaments, filler filaments, and aperture-reinforcing filament discussed in detail below.

Depending on the structural requirements of the individual implant, multiple load bearing filaments or filament passes may be laid down along the same load bearing filament path to provide additional implant strength where required. In general it is envisaged that any textile filament having the desired load bearing capabilities and flexibility for bending to lie along a circuitous path while withstanding encountered in situ loads will be suitable to comprise the filaments described herein. Moreover, filaments of any number of diameters and shapes including ovoid, square, rhomboid and the like of various circumferences can be appreciated by one skilled in the art as falling within the present invention.

The support filaments of the present invention generally provide a substrate capable of supporting tissue ingrowth while additionally providing a scaffold to which the load-bearing, border filaments and aperture reinforcing filaments can attach. Therefore, the support filaments generally extend between and around the apertures comprising any suitable predetermined pattern. Depending on the structural requirements of the individual implant, multiple support filaments or filament passes may be laid down along the same support filament path to adjust the tissue ingrowth or flexibility characteristics of the plate.

The border filaments of the present invention generally define the outermost marginal extent of the plate and provide a frame to which any of the several filaments comprising the plate may attach. Depending on the structural requirements of the individual implant, multiple border filaments or filament passes may be laid down along the same border filament path to adjust the strength and flexibility characteristics of the plate.

Implantation of the device is achieved by positioning the implant body across the affected disc space while aligning any suitable number of the fixation apertures with target receiving tissues. Once preferentially aligned, implantation is completed via insertion of fixation devices through the fixation apertures and into receiving tissue at any preferred angle.

According to a second broad aspect of the present invention, there is provided manufacturing techniques performed on a two-dimensional substrate which produces three-dimensional embroidered structures having the advantageous properties of a multi-modic tension feature imparting residual stretch and variable extension.

According to one embodiment, straight load bearing filaments and zigzag load bearing filaments may be used in an embroidered structure to create a multi-modic tension feature. By way of example only, straight load bearing filaments may create an initial limit to the extension of the embroidered structure under a load. Over time with repeated loading of the embroidered structure, the straight load bearing filaments may stretch out. At this point, the zigzag load bearing filaments may then act as a second limit on the extension of the embroidered structure. Zigzag load bearing filaments may be comprised of a stronger set of threads than straight load bearing filaments. Zigzag load bearing filaments have the capacity to further limit the extension of the embroidered structure after the initial extension limit of the straight load bearing filaments.

When the embroidered structure is in its initial relaxed state, the zigzag load bearing filaments have slack due to the zigzagged thread path. When the embroidered structure is stretched under a repeated load, the zigzag load bearing filaments straighten and are permanently fixated, thereby limiting the overall extension of the embroidered structure. The two sets of load bearing filaments (i.e. straight load bearing filaments and zigzag load bearing filaments) together create the bi-modic tension feature in the embroidered structure to limit stretch/extension across an affected joint or intervertebral disc space and give the embroidered structure residual stretch/variable extension over time.

According to another embodiment, thread paths of long stitches and thread paths of short stitches may be used in an embroidered structure to create a multi-modic tension feature. By way of example only, a thread path with long stitches may have long x-components and minimal y-components in between each lock stitch. As follows, when the thread path with long stitches stretches out, the minimal y-components in between each of the long stitches minimally add to the overall length of the x-component of the long-stitched thread path. In this way, a long-stitched thread path has minimal residual stretch.

By way of example only, a thread path with short stitches may have short x-components and maximal y-components in between each lock stitch. When the thread path with short stitches stretches out, the maximal y-components in between each of the short stitches greatly add to the overall length of the x-component of the short-stitched thread path. In this way, a short-stitched thread path has maximal residual stretch.

This property of adding extra thread length and creating residual stretch may be advantageously employed to give variable extension to an embroidered structure. By way of example only, long-stitched thread paths with minimal residual stretch may be used in an embroidered structure to create an initial limit to the extension of the embroidered structure under a load. Over time with repeated loading of the embroidered structure, the long-stitched thread paths may stretch out. At this point, short-stitched thread paths with maximal residual stretch may then act as a second limit on the extension of the embroidered structure. The two sets of thread paths (i.e. long-stitched thread paths and short-stitched thread paths) together create the bi-modic tension feature in the embroidered structure to limit stretch/extension across an affected joint and give the embroidered structure residual stretch/variable extension over time.

According to a third broad aspect of the present invention, a customizable plate is provided. The preferred plate composition and configuration provides the clinician with the ability to preoperatively or intra-operatively customize a textile plate where the flexibility is determined by filament composition, shape, diameter and number included within the plate. To achieve the desired flexibility afforded by a customizable plate, the pre-customized plate presents a configuration of filaments and apertures such that a large number of filaments and apertures may be cut or excised without destroying the functionality of the resultant customized plate. To achieve the above stated functionality, the plate may comprise any shape including but not limited to oval, rhomboid, triangular, rectilinear and like shapes suitable to achieve a desired therapeutic goal.

Multiple embodiments of the present invention illustrate the inclusion of apertures advantageously positioned within the plate matrix to facilitate anchoring of the device to tissues adjacent to the targeted affected tissue(s). The anchor receiving apertures generally comprise borders which provide preferential anchor engagement sites while concurrently providing attachment sites for plate filaments and other structures. The anchoring aperture borders may comprise any suitable material(s) including but not limited to textiles, metal, carbon fiber, nylon, plastics and the like to which the plate may be attached. Examples of textiles and textile anchoring aperture configurations are shown and described in the above-referenced '225 and '531 patents. The apertures of the present invention may be configured with aperture reinforcing structures including but not limited to additional filaments, grommet like devices and the like comprised of any suitable material including but not limited to plastics, polyester, carbon fiber, metal and the like.

Although illustrated as comprising fixation apertures, it can be appreciated that a plate prepared for implantation might not include prepared fixation apertures where the utility of a fixation device including but not limited to bone cement, sutures, wire and the like does not require an aperture to achieve fixation. Moreover, apertures may be included within the plate to accommodate intrusion of physiological features, and/or structures of complimentarily devices.

Once the device is aligned with receiving tissues, anchoring devices including but not limited to screws, wire, sutures, staples crimps and the like may be inserted through the tissue-aligned anchor receiving apertures and into the receiving tissue thereby affixing the plate thereto.

BRIEF DESCRIPTION OF THE DRAWINGS

In the interest of clarity, distinctions between elements within the drawings are indicated through the use of lines comprising various widths, shades and integrity. Consequently, dashed lines have been included only to identify and more easily distinguish between elements contained in each embodiment, and not to denote any other attribute nor imply any other information. Many advantages of the present invention will be apparent to those skilled in the art with a reading of this specification in conjunction with the attached drawings, wherein like reference numerals are applied to like elements and wherein:

FIG. 43 is a perspective view of an example of an implant insertion device and customizable plate prior to insertion into the implant insertion device according to one embodiment of the present invention;

FIG. 44 is a perspective view of the implant insertion device of FIG. 43 with the customizable plate inserted therein;

FIG. 45 is a perspective view of the implant insertion device of FIG. 43 after releasing the customizable plate; and FIG. 46 is a plan view of the customizable plate preferentially oriented and attached to a targeted implantation site after insertion through the implant insertion device of FIG. 43.

DETAILED DESCRIPTION OF THE PREFERRED EMBODIMENT

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related constraints, which will vary from one implementation to another. Moreover, it will be appreciated that such a development effort might be complex and time consuming, but would be a routine undertaking for those of ordinary skill in the art having the benefit of this disclosure. The textile-based plate system disclosed herein boasts a variety of inventive features and components that warrant patent protection, both individually and in combination.

Figure 1:
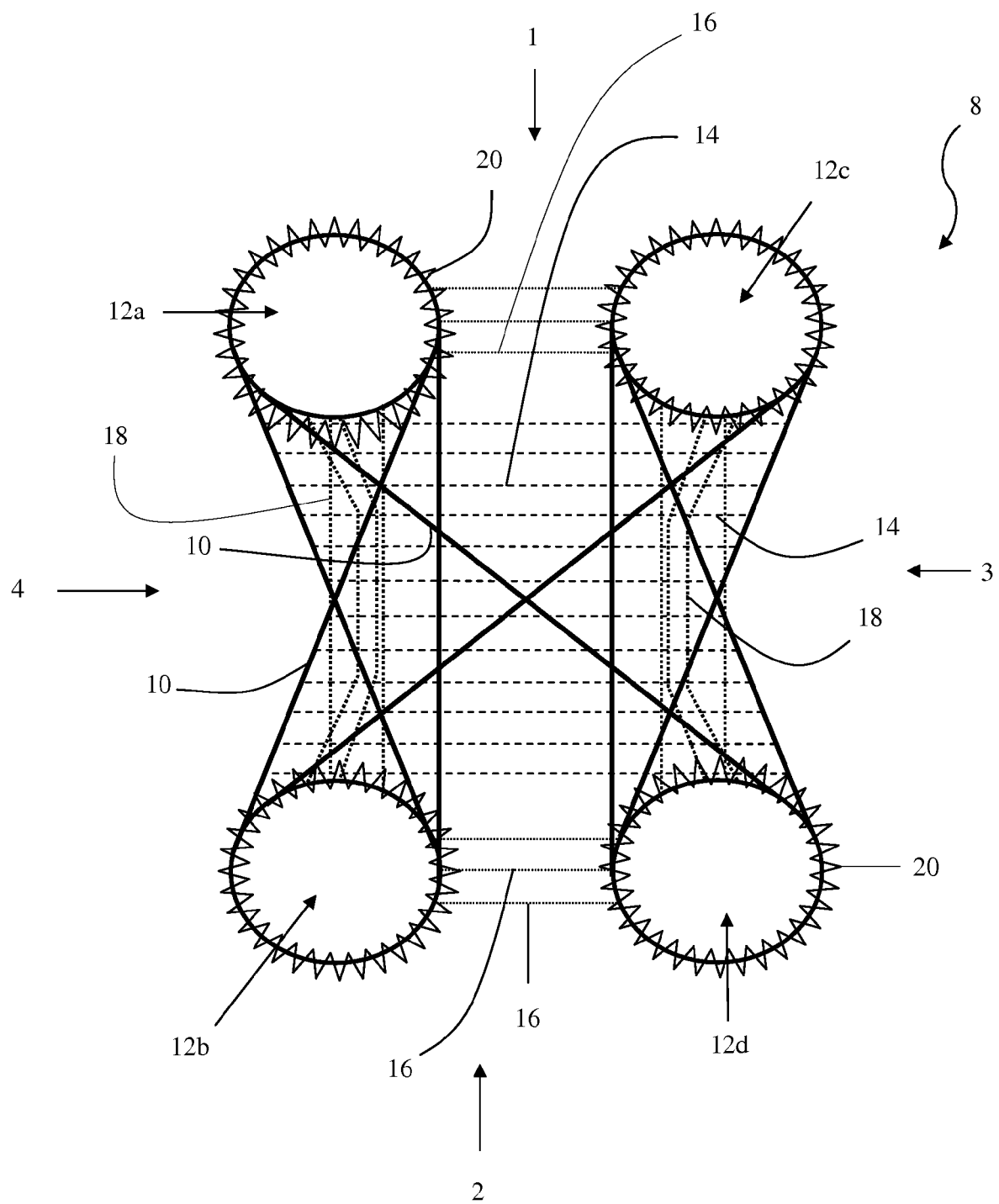
FIG. 1 is a top plan view of a textile-based plate implant according to one embodiment of the present invention having four screw apertures.

FIG. 1 illustrates an example of a textile-based plate implant 8 according to a first embodiment of the present invention. The implant 8 is suitable for posterior, lateral or anterior insertion within the lumbar, thoracic or cervical regions of the spine. In the interest of clarity, each of the below elements are illustrated within FIG. 1 with a line quality common to that element type. Therefore, the use of dotted lines in this and other illustrations within the present application is not intended to denote various views generally attributed to the use of such lines, but rather are meant to indicate different stitching types. The implant 8 generally comprises a lattice work of filaments including load bearing filaments 10, horizontal reinforcement filaments 14, inter-aperture support filaments 16, longitudinal reinforcement filaments 18, and aperture reinforcement filaments 20, which together define the dimensions of the implant 8 including apertures 12a-12d.

The implant may be constructed from any of a variety of textile materials, for example including but not limited to (and by way of example only) permanent or resorbable polyester fiber, polypropylene, polyethylene, ultra high molecular weight polyethylene (UHMWPe), poly-ether-ether-ketone (PEEK), carbon fiber, glass, glass fiber, polyaramide, metal, copolymers, polyglycolic acid, polylactic acid, biodegradable fibers, silk, cellulosic and polycaprolactone fibers, aramid fibers or alginate fibers and the like. The implant may be manufactured using any number of textile processing techniques, for example including but not limited to embroidery, weaving, three-dimensional weaving, knitting, three-dimensional knitting, injection molding, compression molding, and cutting woven or knitted fabrics. In a preferred embodiment described herein, formation of the lattice like structure involves embroidery various types of filaments, including load bearing filaments, stabilization filaments and filler filaments into a dissolvable or permanent backing fabric in a predetermined pattern. Once completed, the embroidered design is isolated through dissolution of the backing material, thus providing an implant composed solely of the "freed" embroidered filaments.

The implant may be sufficiently porous to allow for tissue ingrowth through the implant. Such ingrowth may allow for enhanced fusion of the target vertebrae as well as for increased adhesion of the plate to the bone. Such tissue ingrowth may be either soft or hard bone tissue, or a mixture of the two. Furthermore, the plate may be provided as having ingrowth-inhibiting properties, whether provided via the material of composition, through an additional treatment of the textile material, or by densely embroidering the implant so as to minimize the porosity of the plate. The implant may be formed wholly of one material or a combination of materials (for example different types of filaments comprising different materials based on the various functions of the filaments). For example, some materials may be better suited for tensile load bearing strength, while others may be chosen for density or other properties such as the ability to discourage tissue ingrowth. Additionally, different sections of the plate may be provided with tissue ingrowth promoting or inhibiting properties, for example encouraging ingrowth through certain areas (for example bone-contacting areas to improve adhesion of the plate to the bone) and inhibiting ingrowth in other areas (for example over the disc space to allow for motion retention of the joint) without departing from the scope of the present invention.

It should be understood that "filament" as used herein is synonymous and interchangeable with "thread." Similarly, "substrate," "backing material," and "backing sheet" are also interchangeable terms as used herein. Furthermore, "backing thread" and "bobbin thread" are synonymous terms as used herein.

Figure 2:
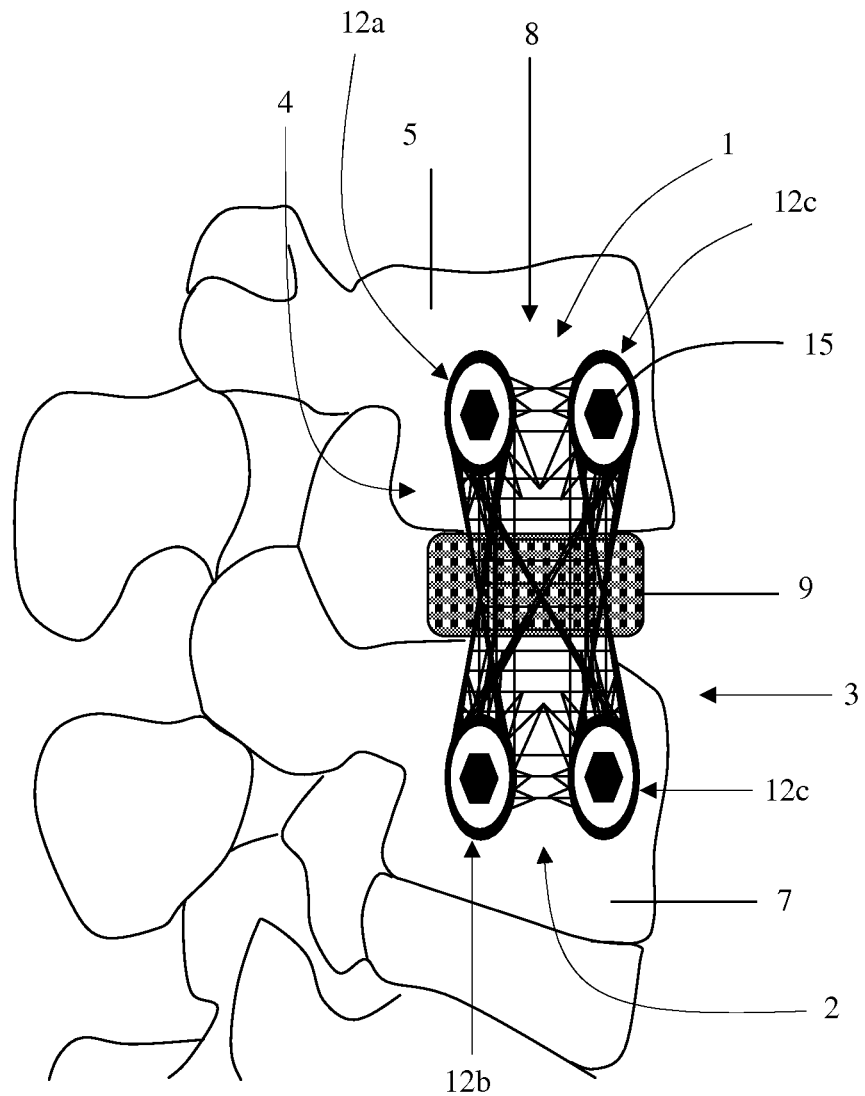
FIG. 2 is a lateral view of the a human spine with the textile-based plate implant of FIG. 1 implanted onto the lateral faces of adjacent vertebral bodies and restricting a fusion implant within a disc space according to the present invention.

As shown, the plate 8 has first and second sides 1, 2 respectively, of length shorter than third and fourth sides 3, 4 respectively, dimensioned thusly to afford preferential alignment with the implant receiving tissues 5, 7 adjacent to the affected joint (FIG. 2). As will be exemplified below, although presented in a generally rectilinear configuration, it can be appreciated that one skilled in the art would recognize that various geometrical plate configurations including but not limited to square, ovoid rhomboid and the like would fall within the scope of the present invention.

The finished plate 8 comprises apertures 12a, 12b, 12c, 12d dimensioned to receive and align fixation devices 15 with targeted fixation device receiving tissues 5, 7. Therefore, the fixation apertures 12a, 12b, 12c, 12d are generally aligned with the first and second plate sides 1, 2 which in turn align with the fixation device receiving tissues 5, 7 adjacent to the affected joint over which the plate 8 spans. Once aligned with receiving tissues 5, 7, any suitable fixation device 15 dimensioned for insertion within the fixation apertures 12a, 12b, 12c, 12d including but not limited to screws, wires, sutures, rivets, nails and the like may inserted said apertures 12a, 12b, 12c, 12d to preferentially affix the device 8 to receiving tissues 5, 7.

FIG. 2 illustrates, for example only, the present embodiment of the current invention after lateral implantation over an affected disc space located between a superior 5 and inferior 7 vertebrae. In the current example, the plate 8 restricts a therapeutic appliance 9 inserted within a disc space through an evacuated laterally oriented surgical corridor intruding through adjacent tissues and into the disc space. For example only, implantation of the plate 8 proceeds by aligning the first plate side 1 with the lateral surface of the superior vertebral body 5 adjacent to the disc space opening through which the previously placed therapeutic appliance 9 was inserted and resides, and orienting the remainder of the implant 8 to overlay the targeted disc space. Once preferentially positioned, fixation devices 15 including but not limited to screws, wires, sutures, rivets, nails and the like are inserted into apertures 12a, 12c to selectively attach said first side 1 to the receiving tissue 5. Subsequent to fixation of the first side 1, implantation of the plate 8 is completed by preferentially aligning the second plate side 2 with the lateral surface of the inferior vertebral body 7 adjacent to the disc space opening through which the therapeutic appliance 9 was inserted and resides. Once aligned, fixation devices 15 are selectively inserted through the apertures 12b, 12d and into the receiving tissue 7. Although illustrated as attached to a lateral aspect of adjacent vertebral bodies 5, 7, it can be appreciated that the present embodiment of the current invention may be affixed to any number of desired tissues including but not limited to generally lateral, anterior and posterior vertebral surfaces to effect a variety of therapeutic outcomes. As can be appreciated, the sequence of fixation device 15 insertion through the apertures 12a, 12b, 12c, 12d may proceed in any desired sequence, with the apertures 12a, 12b, 12c, 12d aligned with any preferred receiving tissue with said alternative implantation methods falling within the scope of the present invention. Furthermore, the implant 8 may or may not be used in conjunction with complimentary therapeutic devices.

FIGS. 3-8 illustrate sequentially one example of a method of embroidery employed to construct one embodiment of the present invention for use in the lumbar, thoracic or cervical region of the spine. To denote the sequence of embroidery leading to the completed implant, each of FIGS. 3-8 illustrate the inclusion of an additional filament type within the backing material 6. Therefore, in the interest of clarity, the newly included filament in a given figure is denoted by an emboldened line, while filaments introduced in earlier figures of the present embodiment are denoted by light, dotted lines.

Figure 3:
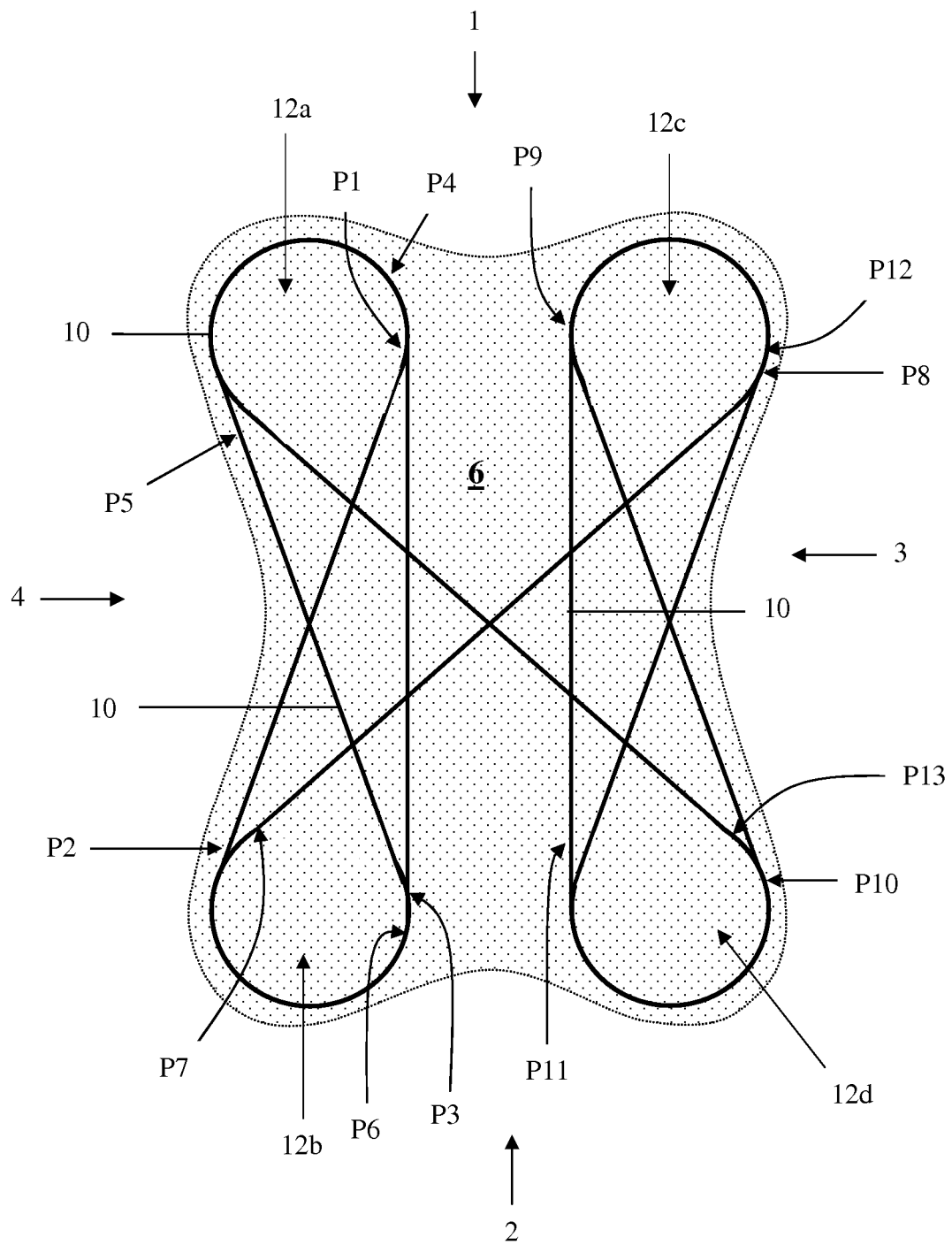
FIG. 3 is a top plan view of backing material with load bearing filaments embroidered thereon, forming part of the implant of FIG. 1.

Referring to FIG. 3, formation of the plate 8 is generally achieved through embroidery of the various filaments 10, 14, 16, 18, 20 in a predetermined pattern onto a dissolvable backing material 6. Construction of the plate begins with embroidery of load bearing filaments 10 into the backing material 6. The load bearing filament 10 prevents extension across the affected joint by transferring any in situ load encountered through fixation devices 15 to the fixation element receiving tissues 5, 7 (e.g. vertebral bodies). Therefore the load bearing filament 10 is stitched by example only into the backing material 6 in a continuous manner beginning at point P1 and continuing to point P11.

A general process of embroidering a textile implant is shown and described in U.S. Pat. No. 7,338,531, issued Mar. 4, 2008 and entitled "Textile Prosthesis," and U.S. Pat. No. 7,214,225, issued May 8, 15 and entitled "Connector," the complete disclosures of which are hereby incorporated by reference in their entireties as if set forth fully herein. The load bearing filaments of the present invention provide the major source of load bearing strength required by the implant to preferentially limit extension across the affected joint.

Therefore, the load bearing filaments extend between and at least partially around the apertures, and ultimately transfer any encountered in situ loads to the fixation devices positioned therein and ultimately to their receiving tissues. Although shown and described herein as a "load bearing filament" in the singular, it should be understood (in light of the above discussion of the embroidery process) that each load bearing filament comprises at least a pair of threads (e.g. a stitching thread and a bobbin thread) embroidered on either side of the backing material. Once the backing material is dissolved away, the thread pair made up of the stitching and bobbin threads remains as a "load bearing filament." This understanding also applies to the support filaments, border filaments stabilization filaments, filler filaments, and aperture-reinforcing filament discussed in detail below.

Embroidery of the load bearing filament 10 originates at point P1 and continues diagonally across the plate through point P2 and then looping around the outside of intended aperture 12b in a counterclockwise direction until reaching point P3. From point P3, embroidery of the filament 10 continues generally parallel to the longitudinal midline of the backing material 6 through point P4 and loops around the outside of intended aperture 12a in a counterclockwise direction until reaching point P5. Embroidery of the filament 10 then proceeds generally diagonally through point P6 and loops clockwise around the outside of intended aperture 12b until reaching point P7. Upon reaching point P7, the embroidery run continues generally diagonally across the material 6, passing through point P8 and looping counterclockwise around the outside of intended aperture 12c to reach point P9. From point P9, embroidery of the filament 10 proceeds to point P10, loops clockwise around the outside of intended aperture 12d before reaching point P11. The embroidery run then continues generally linearly across the plate 8, and loops in a clockwise direction around the outside of intended aperture 12c to arrive at point P12. From point P12 the embroidery run continues generally diagonally across the backing material 6 to loop counterclockwise around the outside of intended aperture 12d before reaching point P13. After reaching point P13, embroidery of the filament is completed by extending the embroidery run diagonally across the material 6 and then loops clockwise around the outside of intended aperture 12a before ending at point P1.

The amount of load supported by the completed implanted plate 8 is primarily determined by the number of load bearing filaments 10 deposited within the plate 8 matrix. Therefore it can be appreciated that any number of filament 10 passes of load bearing filaments 10 may be laid down along an intended filament 10 path in any number of path configurations to achieve optimal load bearing characteristics desired within the plate 8. Additionally, although described in the present embodiment as comprising a single length of filament, the predetermined load bearing filament pathway may be embroidered with multiple lengths of filaments to complete the desired filament 10 configuration. It is notable that the load bearing filaments 10 are only applied around the outside of intended apertures 12a-12d. This feature increases the integrity of the implant under load by ensuring minimal aperture deformation during load.

Figure 4:
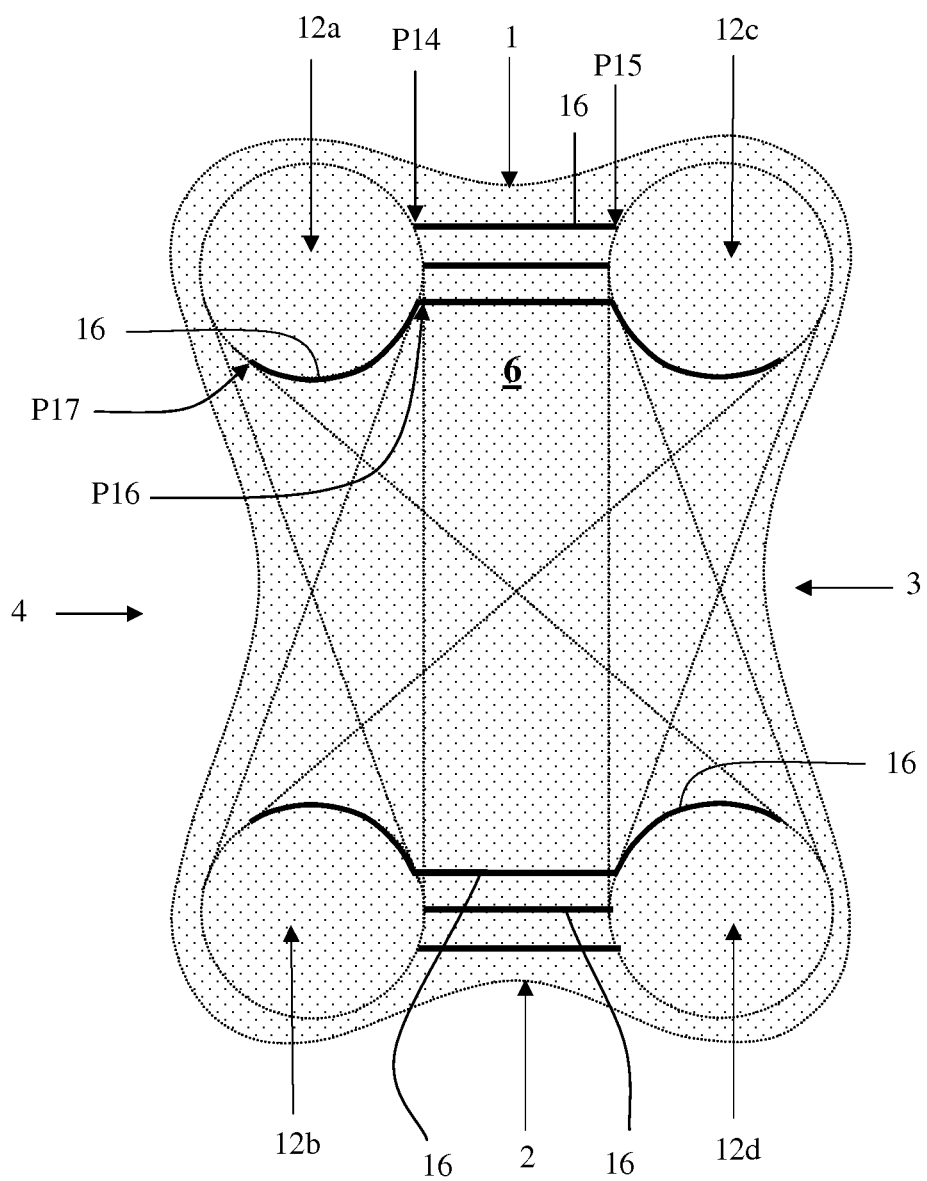
FIG. 4 is a top plan view of the backing material and load bearing filaments of FIG. 3 (shown in phantom) with inter-aperture support filaments embroidered thereon according to the present invention.

Referring to FIG. 4, embroidery of the inter-aperture support filaments 16 generally begins once embroidery of the load bearing filaments 10 is completed. The inter-aperture support filaments 16 are embroidered into the backing mesh 6 and extend between a pair of fixation apertures 12a-12c, 12b-12d proximate to either the first 1 or second 2 plate side, and complete the outline of the fixation apertures 12a-12d forming the remainder of the intended aperture borders by closing the open extent of the intended aperture outlined by the load bearing filaments 10. The inter-aperture support filaments 16 support aperture 12a, 12b, 12c, 12d orientation and integrity while concurrently fractionally sharing in situ plate 8 loads. Because the interior borders of the apertures 12a-12d are completed with non load-bearing threads, the completed apertures 12a-12d will not deform under loads.

An exemplary method of laying down the inter-aperture support filaments 16 comprises embroidery of a first inter-aperture reinforcement filament 16 to engage the aperture 12a border filament at a point P14 proximate to said first side 1. Embroidery of the filament 16 then proceeds across the backing material 6, generally parallel to said first plate side 1 to engage aperture border 12c filament 10 at point P15. After a predetermined number of filament 16 passes is embroidered over the first path, the embroidery apparatus then shifts toward said second side 2 to embroider a predetermined number of filament 16 passes over a second path. The second inter-aperture support filament 16 portion is then laid down generally parallel to the first filament 16 path to connect and engage the filaments 10 comprising the aperture borders of apertures 12a, 12c. The above mentioned process is repeated until the desired number of aperture support filaments have been laid down between said apertures 12a, 12c along the desired number of filament 16 pathways. Once embroidery of the aperture reinforcement filaments 16 for a given aperture pair is completed, an arc section of inter-aperture support filament 16 is then embroidered into the backing material 6 to close the generally circular outline of each fixation aperture 12a, 12c, for example between points P16 and P17 of aperture 12a. Upon completion of embroidery of the said arc sections, the aforementioned process is repeated for aperture pair 12b-12d. It can be appreciated that as each filament 16 pass continues, the filament 16 will engage any previously laid filament 10 encountered. Although exemplified in the present illustration as having a triad of inter-aperture support filaments 16 paths extending between adjacent aperture pairs 12a-12c, 12b-12d it can be appreciated that any number of inter-aperture support filaments 16 within any preferred number of filament 16 pathways may be included in any number of configurations and patterns suitable to sustain aperture 12a, 12b, 12c 12d orientation within the plate matrix 8. Furthermore it can be appreciated that the filaments 16 may or may not be provided for any pair of apertures within the plate 8.

Figure 5:
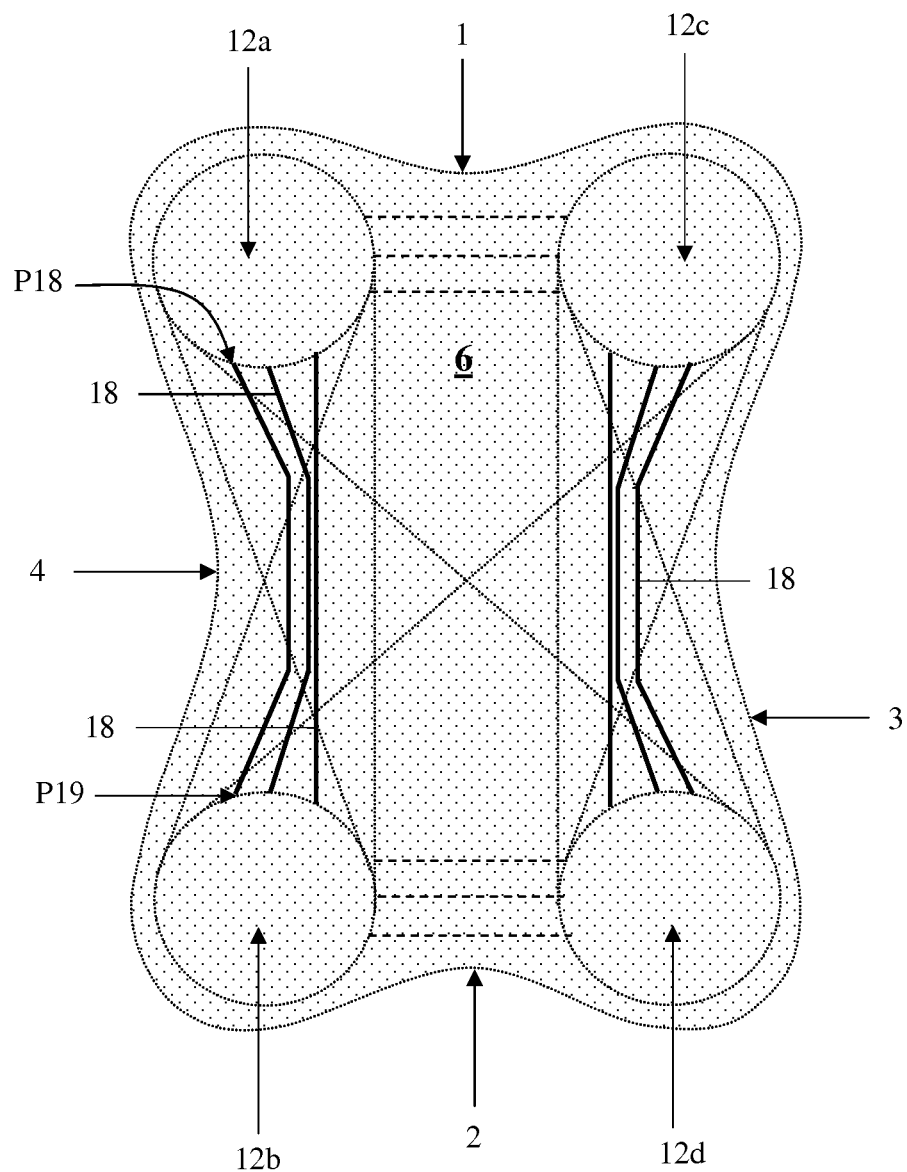
FIG. 5 is a top plan view of the backing material, load bearing filaments, and inter-aperture support filaments of FIG. 4 (shown in phantom) with longitudinal reinforcement filaments embroidered thereon according to the present invention.

Referring to FIG. 5, installation of longitudinal reinforcement filaments 18 commences once embroidery of inter-aperture support filaments 16 has been completed. The completely embroidered set of longitudinal support filaments 18 extend generally parallel to the third and fourth sides 3, 4 of plate 8 and between each aperture pair 12a-12b, 12c-12d while engaging each filament 10, 16 over which the longitudinal reinforcement filament 18 passes. The longitudinal reinforcement filaments 18 help maintain the structural integrity of the device by preserving load bearing filament 10 and aperture 12a, 12b, 12c, 12d orientation within the plate 8 matrix, without sharing any of the in situ load experienced by the load bearing filaments 10.

For example only, embroidery of the longitudinal reinforcement filament 18 commences at a point P18 generally proximate to said fourth 4 plate side on aperture 12a and continues along a generally linear path until engaging the filament comprising the border of aperture 12b at point P19. After embroidering a predetermined number of filament 18 passes along the aforementioned filament 18 path, the embroidery apparatus shifts a predetermined distance toward the longitudinal midline of the plate 8 in alignment with and engaging aperture border 12b to begin another generally linear embroidery pass toward and ultimately engaging the border of aperture 12b. The instantly above mentioned embroidery sequence is then repeated until a preferred number of embroidery passes and filaments 16 have been embroidered within the backing material and between said aperture pairs 12a-12b, 12c-12d.

Although illustrated in the present embodiment as including six longitudinal reinforcement filaments 18 it can be appreciated by one skilled in the art that any number of longitudinal support filaments 18 may be included within the plate 8 matrix in a variety of orientations, shapes and configurations to effect the desired level of support required by a given array of filaments 10, 16 residing within the plate 8.

Figure 6:
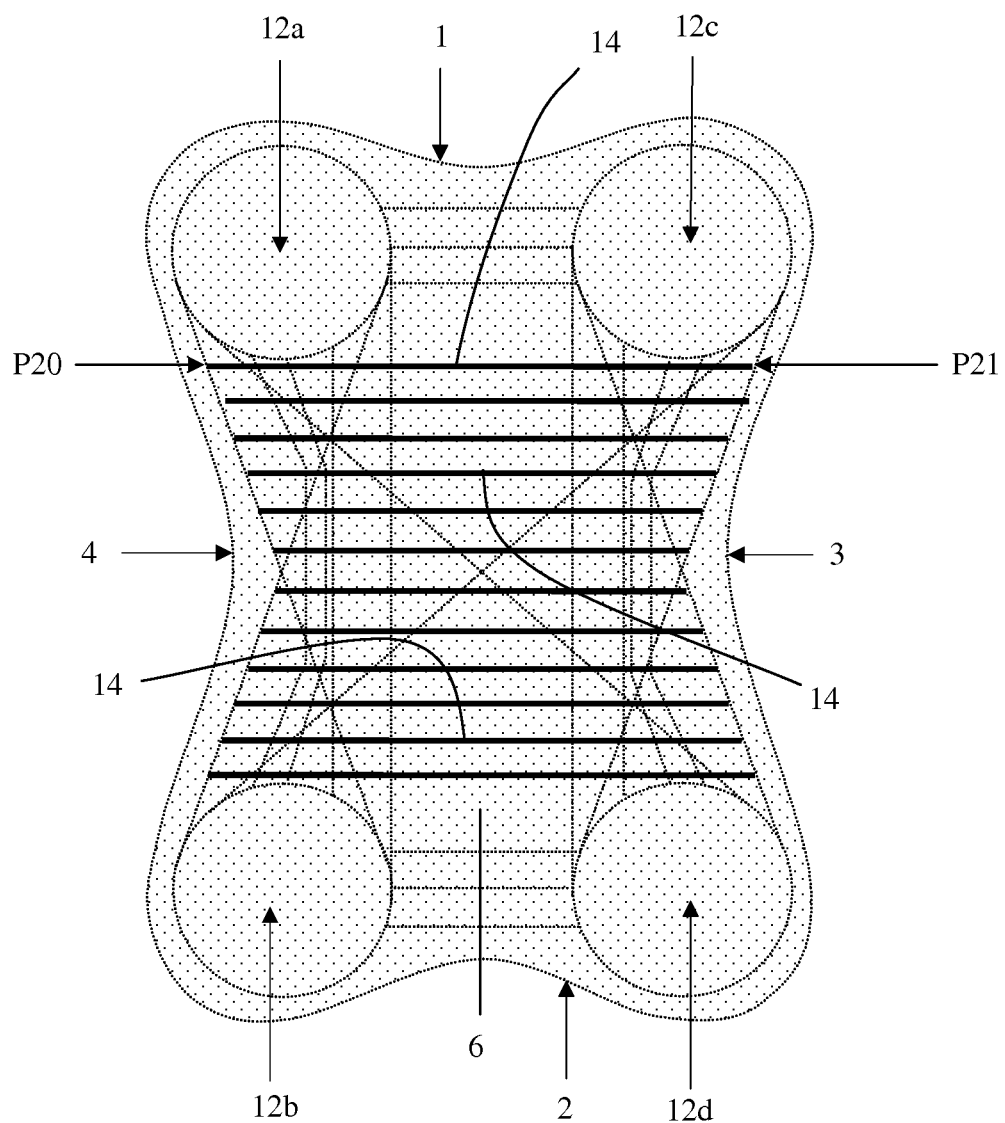
FIG. 6 is a top plan view of the backing material, load bearing filaments, inter-aperture support filaments, and longitudinal reinforcement filaments of FIG. 5 (shown in phantom) with lateral reinforcement filaments embroidered thereon according to the present invention.

As illustrated in FIG. 6, upon completion of longitudinal filament 18 embroidery, embroidery of the horizontal support filaments 14 commences. The horizontal support filaments 14 help maintain filament 10, 18 orientation within the plate matrix 8 by engaging filaments 10, 18 while concurrently providing "filler" material (or "backing mesh") to the plate without providing additional load bearing support to the plate 8. The horizontal support filaments 14 are embroidered within the backing material 6 generally parallel to the first 1 and second 2 plate sides and between the load bearing filaments 10 which define lateral boarders of the plate 8 and between and not engaging the outer extent of the fixation aperture 12a, 12b, 12c, 12d borders. For example only, embroidery of the filaments 14 begins at a point P20 on the load bearing filament 10 comprising the implant's fourth side 4 and proximate to aperture 12a. Embroidery begins by joining the filament 14 to the load bearing filament 10, and then proceeding along a generally linear path parallel to the first 1 and second 2 plate side until reaching and engaging the load bearing filament(s) 10 comprising the third plate side 3 at point P21. After embroidery of a predetermined number of filament 14 passes along the first path P20-P21, the embroidery apparatus shifts a predetermined distance toward the second plate side 2, and another generally linear filament 14 pass proceeds toward and ultimately engages the filaments 10 comprising the fourth plate side 4. Embroidery of the horizontal reinforcement filament continues in the instantly above manner until a predetermined filament 14 configuration is achieved. Although exemplified as including twelve embroidery paths, it can be appreciated that any number of horizontal support filament 16 paths may be included within the plate matrix 8. In addition to providing substance to the plate 8, the horizontal support filaments 16 also preserve preferred filament 10 orientation within the plate 8 matrix, in effect "sandwiching" the load bearing filaments 10 between the stitching and bobbin threads that comprise the horizontal support filaments 16.

Figure 7:
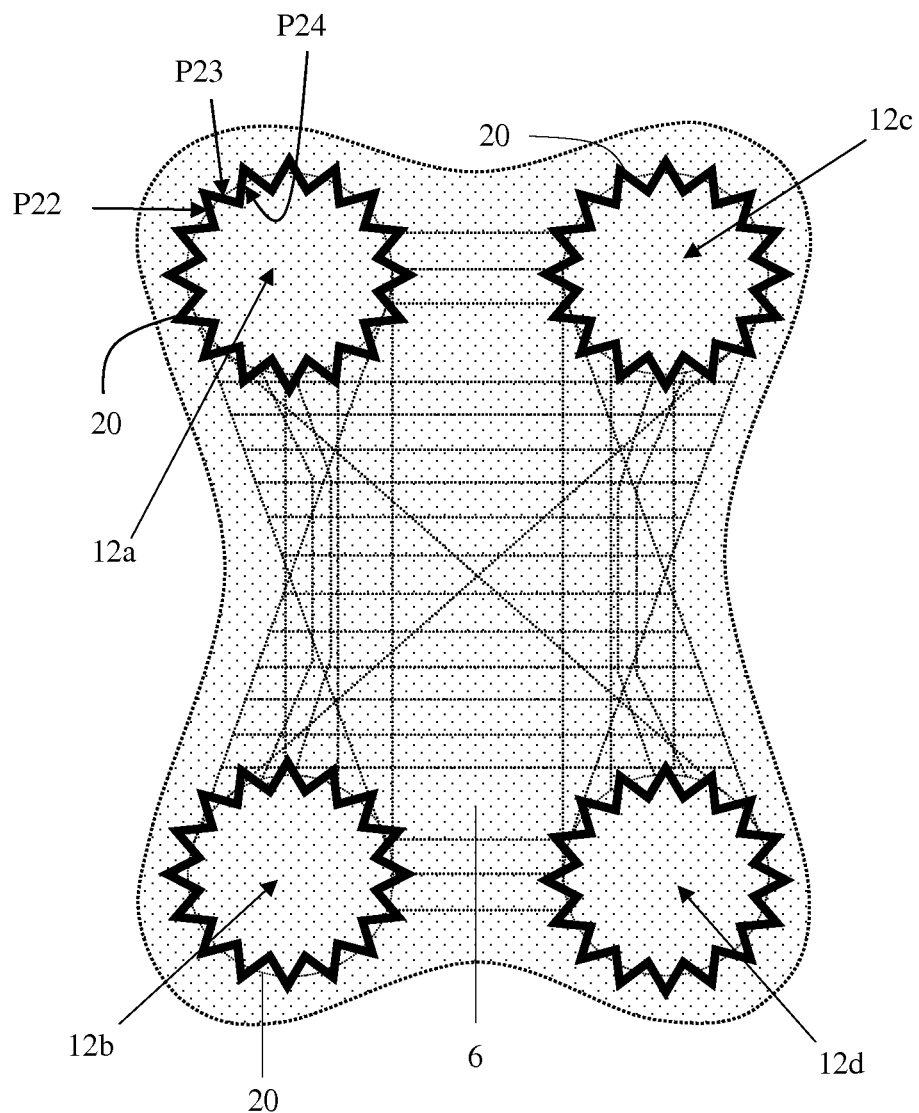
FIG. 7 is a top plan view of the backing material, load bearing filaments, inter-aperture support filaments, longitudinal reinforcement filaments, and lateral reinforcement of FIG. 6 (shown in phantom) with filaments and aperture reinforcement filaments embroidered thereon according to the present invention.

Referring to FIG. 7, the final step in the construction of the present plate 8 embodiment is completed through embroidery of aperture reinforcement filaments 20 over the lengths of filaments 10, 16 which outline each of the fixation apertures 12a, 12b, 12c, 12d (hereinafter collectively called the "aperture border filament"). The aperture reinforcement filaments 20 provide structural integrity to each aperture 12a, 12b, 12c, 12d border filament while concurrently holding the position of the load bearing filaments 10 around each aperture 12a, 12b, 12c, 12d (for example, between the stitching and bobbin threads that comprise the aperture reinforcement filaments 20). By example only embroidery of the aperture reinforcement filament 20 of the present embodiment begins at a point P22 on the aperture 12a border filament by joining said filament 20 to said aperture border filament. Embroidery then continues along a predetermined pathway until the aperture 12a border filament is preferentially reinforced. For example only, embroidery of the filament 20 of the present embodiment proceeds from the embroidery origination point P22 by initiating an embroidery run away from the aperture 12a for a predetermined distance along a line generally not perpendicular to the aperture's tangent at point P22 and potentially engaging any filament 10, 14, 18 in its path. After reaching the predetermined distance away from the aperture 12a border filament, the embroidery run then returns along a path to engage the aperture 12a border filament at a point P23 clockwise from the origination point P22 and continues for a predetermined distance toward the aperture's 12a midpoint. Upon reaching a predetermined distance, the embroidery run returns to and engages the border 12a filament at a point P24 clockwise from the previous border filament engagement point P23. Repetition of the above process, stitching a run away from the aperture 12 border filament for a predetermined distance at a first angle, then returning at a second angle to engage the aperture 12a border filament, while progressing in a clockwise direction ultimately results in a star like pattern which may engage a plurality of filaments 10, 14, 16, 18 to ultimately provide the preferred performance characteristics demanded by a given implant scenario. Upon completing the embroidery of the aperture reinforcement filament 20 for aperture 12a, embroidery of the remaining apertures 12b, 12c, 12d may be completed as described instantly above in any order including but not limited 12b, 12c and then finally 12d. Although illustrated as a plurality of triangular embroidery paths extending from the aperture border, it can be appreciated that any number of passes of aperture support filaments 20 may be embroidered into the backing material 6 in any geometrical shape suitable for securing and preserving aperture 12a, 12b, 12c, 12d positioning and shape within the plate 8 matrix including but not limited to square, oval, circular, rectilinear, rhomboid and like shapes suitable for preferentially engaging surrounding filaments 10, 14, 16, 18 within the plate 8.

Figure 8:
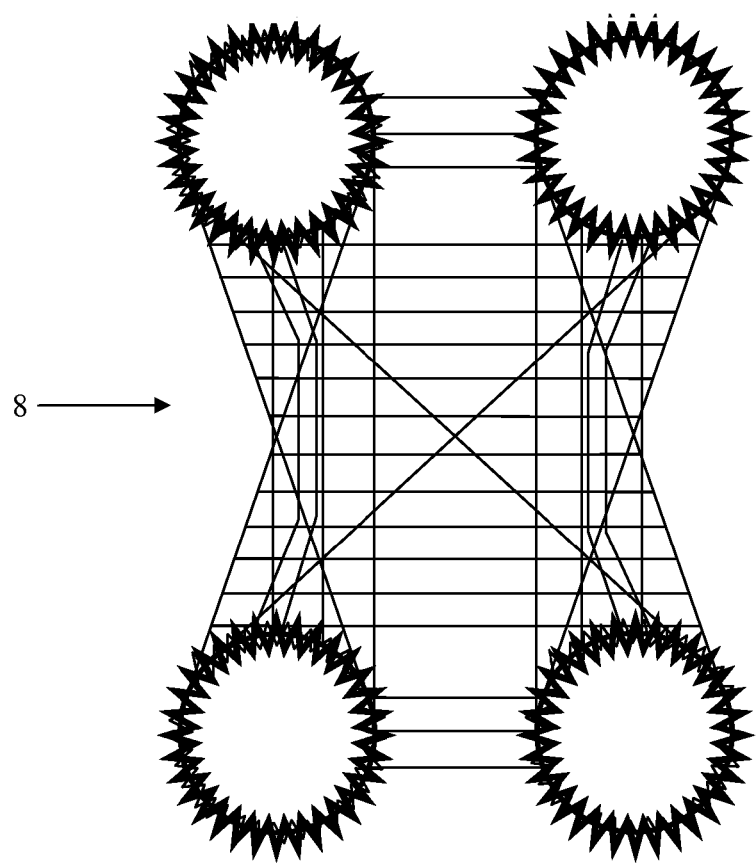
FIG. 8 is a top plan view of the textile-based plate implant of FIG. 7 after removal of the backing material according to the present invention.
Figure 9:
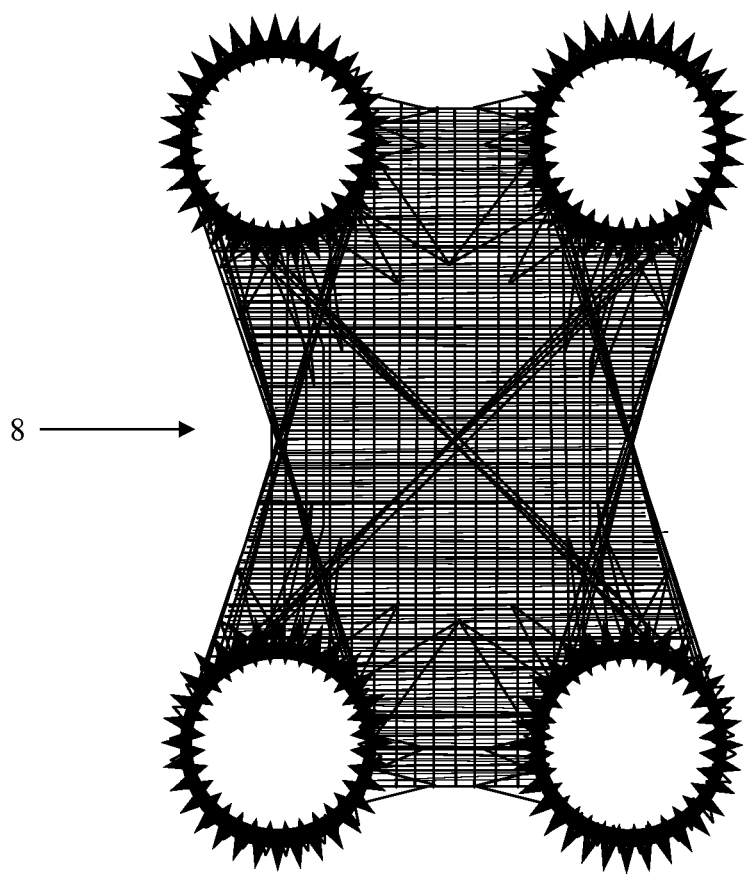
FIG. 9 is a top plan view of a textile-based plate implant of the type shown in FIG. 7 having an alternative filament path density according to the present invention.

Upon completing inclusion of the preferred number of filaments 10, 14, 18, 20 over the desired number of filament pathways, the backing material 6 is removed from the completed device, for example by dissolving the backing material 6 resulting in the finished implant 8 shown in FIG. 8. As illustrated in FIG. 9, alternative embodiments of the present invention may generally comprise an interconnected latticework of filaments provided through similar constructions methods resulting in a desired density as demanded by the given intended implantation site. The general appearance of the plate 8 may be altered by including more or less filler material.

Figure 10:
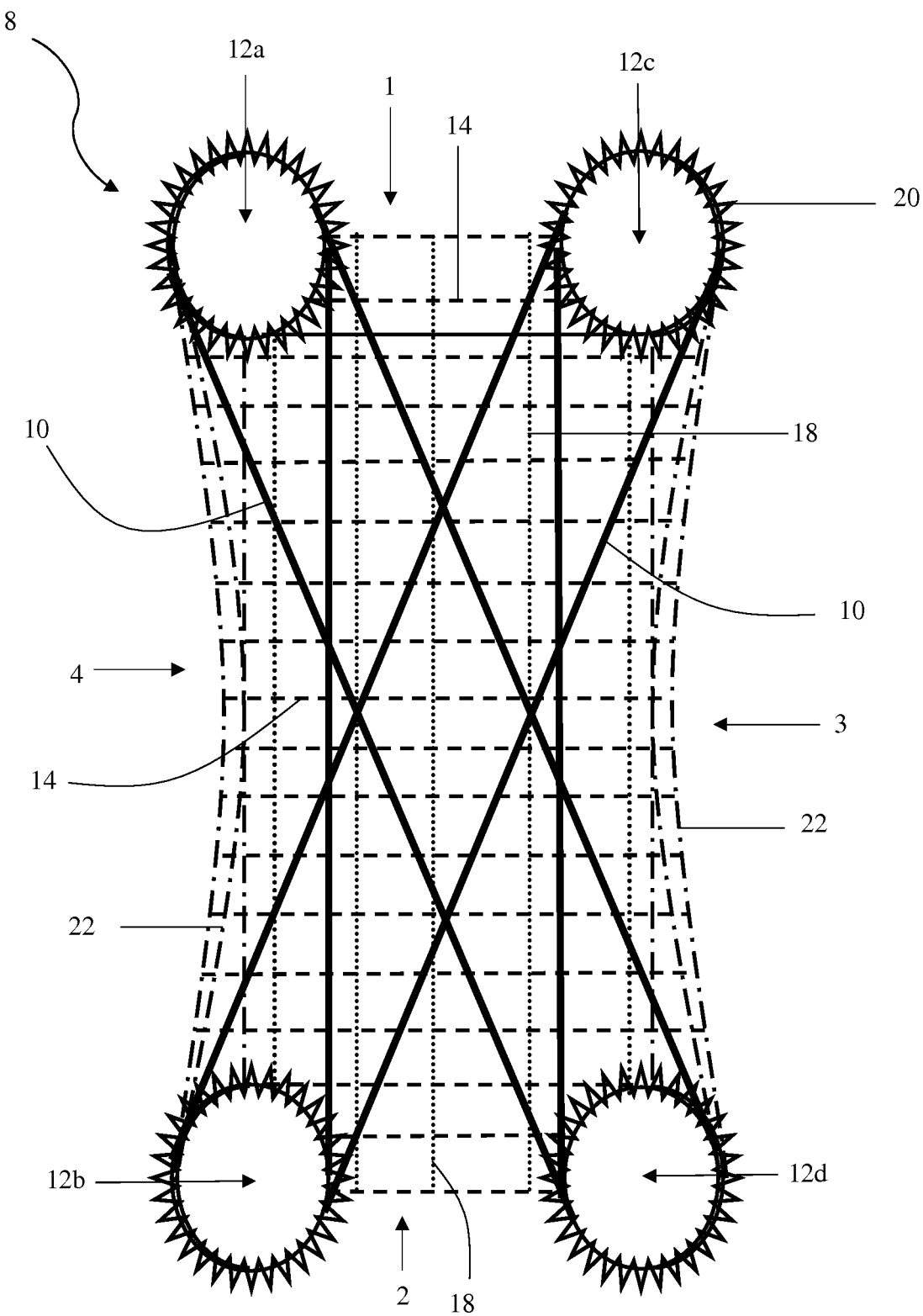
FIG. 10 is a top plan view of a textile-based plate implant according to an alternative embodiment of the present invention having four screw apertures.

As will be evident to one skilled in the art and as illustrated in FIG. 10, manufacture of the present invention via embroidery provides the manufacturer with the ability to create a variety of implants consisting of differing numbers and positions of apertures, and various strengths and properties determined by the number of filament passes embroidered over a variety of pathways into the backing material 6. Thus, it can be appreciated by one skilled in the art that multiple variations of the present device will be recognized as falling within the scope of the claimed invention. For example only, the present embodiment illustrates an implant comprising 4 fixation apertures 12a, 12b, 12c, 12d of similar configuration as the first described embodiment. Therefore, it can be appreciated that preferential implantation of the present embodiment can be described by FIG. 2 and the accompanying description describing implantation of the first embodiment above.

Although shown and described by example above as occurring in a particular order (load bearing filaments 10 first, inter-aperture support filaments 16 second, longitudinal support filaments 18 third, horizontal support filaments 14 fourth, and aperture reinforcing filaments 20 last), the various steps of the embroidery process described above may be performed in any order. However, embroidering the load bearing filaments 10 first advantageously helps maintain their desired orientation within the plate, due to the "sandwich" effect provided by the stitching and bobbin threads of the remaining filaments.

For example only FIGS. 11-16 illustrate the sequential construction of an alternative example of the textile-based plate implant 8 of the present invention dimensioned for use within the lumbar, thoracic and cervical regions of the spine. In the interest of clarity, each of the below elements are illustrated within FIG. 11 with a line quality common to that element type. Therefore, the use of dotted lines in this and other illustrations within the present application is not intended to denote various views generally attributed to the use of such lines.

The present example of plate 8 as illustrated in FIGS. 11-16 comprises a generally rectilinear and planar textile based plate 8 including four fixation apertures 12a, 12b, 12c, 12d and composed of load bearing filaments 10, horizontal reinforcement filaments 14, longitudinal aperture reinforcement filaments 22, longitudinal reinforcement filaments 18 and aperture reinforcement filaments 20. As shown, the plate 8 has first and second sides 1, 2 of length shorter than third and fourth sides 3, 4 dimensioned thusly to afford preferential alignment with the implant receiving tissues (e.g. vertebral bodies) adjacent to the affected joint. As will be exemplified below, although presented in a generally rectilinear configuration, it can be appreciated that one skilled in the art would recognize that various geometrical plate configurations would fall within the scope of the present invention.

To denote the sequence of embroidery leading to the completed implant, each of FIG. 11-15 illustrate the inclusion of an additional filament type onto the backing material 6. Therefore, in the interest of clarity, the newly included filament in a given figure is denoted by an emboldened line, while filaments introduced in earlier figures of the present embodiment are denoted by light, dotted lines.

Figure 11:
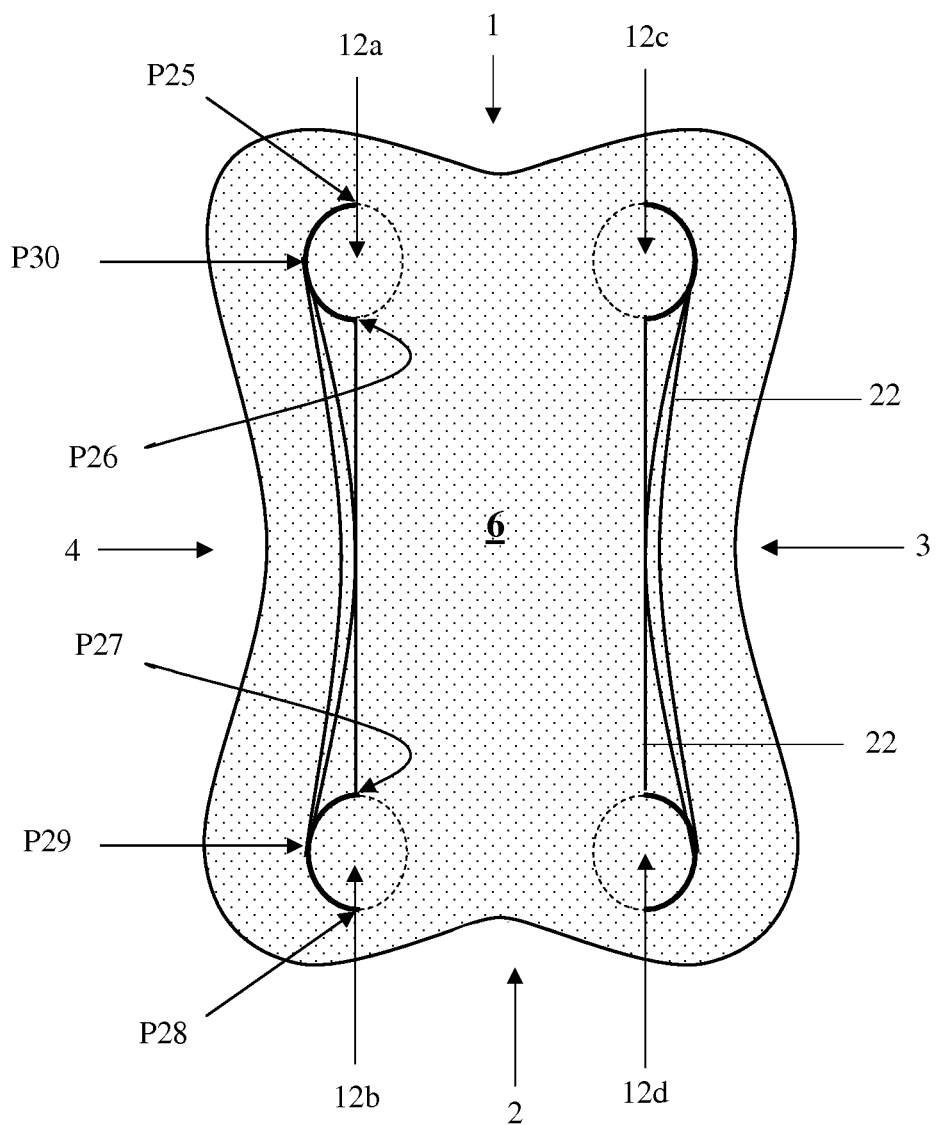
FIG. 11 is a top plan view of backing material with aperture support filaments embroidered thereon, forming part of the implant of FIG. 10 according to the present invention.

Embroidery of the present embodiment of plate 8 begins, for example only, with embroidery of the longitudinal aperture reinforcement filaments 22 onto backing sheet 6, as shown in FIG. 11. Longitudinal aperture reinforcement filaments 22 partially form and support the aperture 12a, 12b borders and provide minimal load bearing support across the plate 8 matrix. The longitudinal reinforcement filaments 22 extend between and partially outline two pair of intended fixation apertures 12a-12b and 12c-12d (illustrated by the dotted lines in FIG. 11) proximate to the third and fourth sides 3, 4 in order to support preferential fixation aperture 12a, 12b, 12c, 12d orientation within the plate 8 matrix. Generally and for example only, embroidery of the filament 22 begins by embroidering an arc portion of aperture border 12a beginning at point P25 and ending at point P26, then proceeds along a predetermined path across the plate 8 between points P26 and P27, generally parallel to the plate's longitudinal midline to stitch an arc portion of aperture 12b between points P27 and P28. After embroidering a predetermined number of filament 22 passes over the instantly above described first path, the embroidery apparatus shifts a predetermined distance toward the fourth side 4 and aligns with the aperture 12b border at point P29. Embroidery of another generally linear filament 22 over a second embroidery path begins by first engaging aperture 12b border at point P29 and then progresses toward and ultimately engages the filament 22 comprising aperture border 12a at point P30. After embroidery of a predetermined number of filaments 22 have been included within the instantly above described second embroidery path, a predetermined number of filament 22 passes then ensue over a predetermined number of embroidery paths extending between the aperture pair 12a-12b. Once the predetermined number of said passes has been laid over said paths, the above process is repeated between the second pair of intended fixation apertures 12c, 12d proximate to the fourth side 4.

Although illustrated in the above fashion, it can be appreciated by one skilled in the art that an implant of the present invention may include any of a variety of embroidery sequences, paths and configurations with which to include aperture reinforcement filaments 22 spanning the longitudinal length of the present invention and extending between included aperture pairs.

Figure 12:
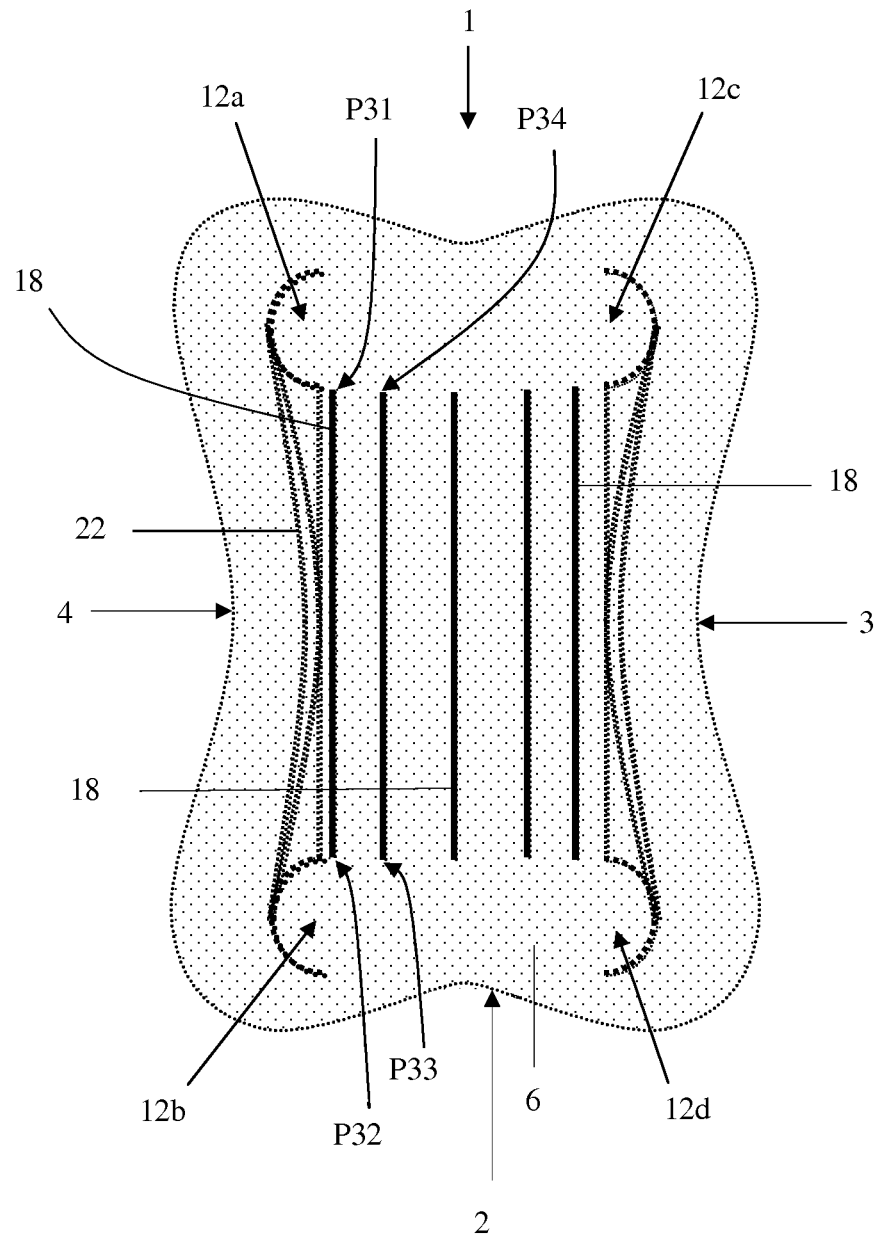
FIG. 12 is a top plan view of the backing material and aperture support filaments of FIG. 11 (shown in phantom) with longitudinal reinforcement filaments embroidered thereon according to the present invention.

FIG. 12 shows the addition of longitudinal reinforcement filaments 18 embroidered into the backing material 6. The longitudinal reinforcement filaments 18 are embroidered into the backing material 6 generally parallel to the longitudinal midline of plate 8 in order to provide load bearing support and structural integrity to the finished plate 8 matrix. Embroidery of the filaments 18 may begin with alignment of the embroidery apparatus with a point P31 proximate to the plate corner defined by the first and fourth sides 1, 4 of plate 8. Embroidery of the filament 18 proceeds by following a generally linear path parallel to the plate's longitudinal midline to a point P32 proximate to the location of intended aperture 12b. After embroidery of a predetermined number of filament 18 passes is completed, the embroidery apparatus shifts a predetermined distance toward the third plate side 3 to commence a first filament 18 embroidery pass over a second embroidery path. The embroidery assembly then begins a return pass over a second path originating at point P33. From point P33 embroidery of the filament 18 commences and proceeds generally linearly across the backing material and generally parallel to plate's midline until reaching a point P34 proximate to the plate's first side 1. After embroidering a predetermined number of filament 18 passes over said second path, the embroidery apparatus shifts a predetermined distance toward the third plate 3 side to begin a third embroidery pass over a third pathway. The above mentioned process is repeated until a preferred number of filaments 18 have been embroidered over a desired number of filament 18 paths. For example only, FIG. 12 illustrates an implant 8 including five longitudinal reinforcement filaments 18. However, it can be appreciated that devices containing any number of longitudinal reinforcement filament passes originating in any number of positions would be recognized by one skilled in the art as falling within the scope of the present invention.

Figure 13:
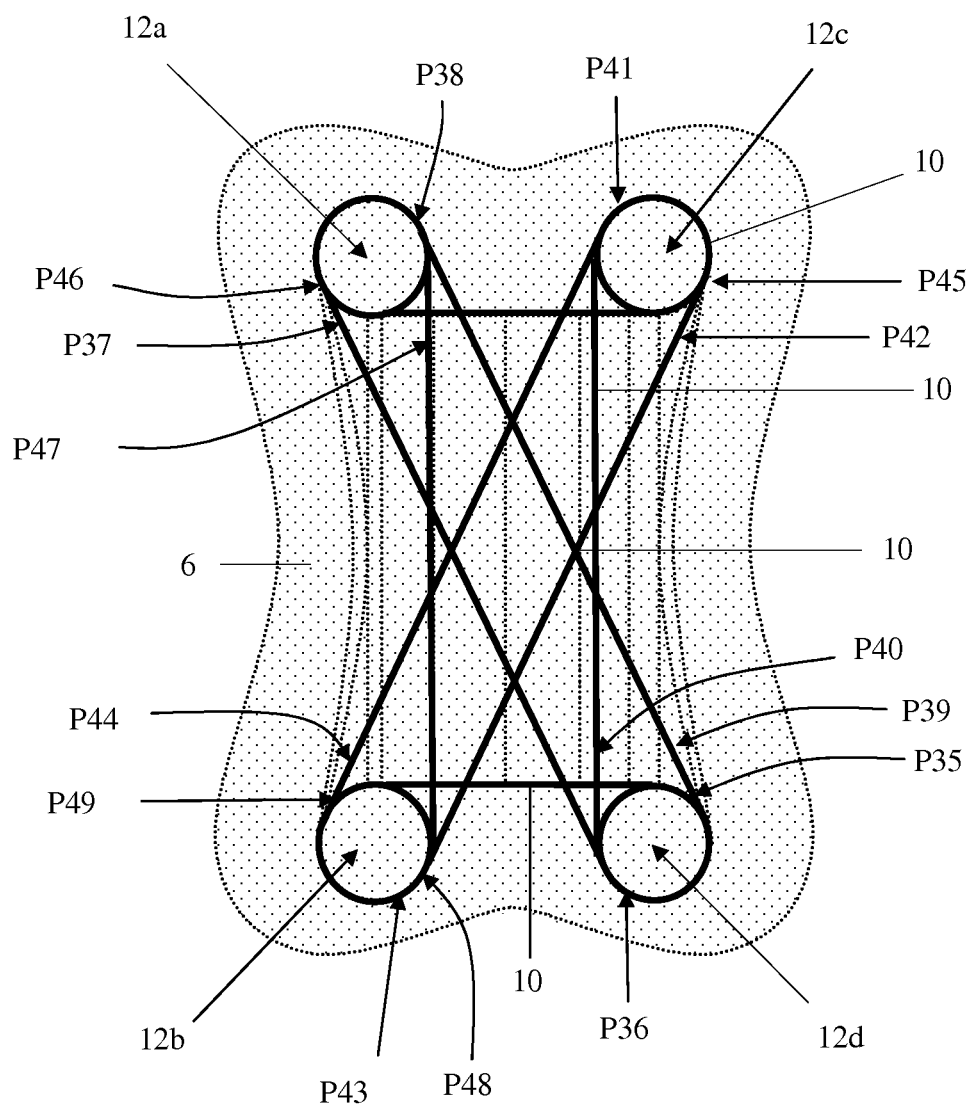
FIG. 13 is a top plan view of the backing material, aperture support filaments and longitudinal reinforcement filaments of FIG. 12 (shown in phantom) with load bearing filaments embroidered thereon according to the present invention.

FIG. 13 illustrates the inclusion of load bearing filaments 10 embroidered onto the backing material 6. The load bearing filaments 10 of the present embodiment provide the primary source of load bearing capacity exhibited by the plate 8, and therefore are generally provided as a single filament which at least partially encircles each fixation aperture present within the implant 8.

For example only, embroidery of the load bearing filament 10 of the present invention describes the inclusion of the filament 10 into the backing material 6 over a predetermined pathway as illustrated by the pathway beginning at point P35 and progressing through points P36-P49 before returning again to point P35. Embroidery of the filament 10 begins at point P35 proximate to the intended aperture 12d. From point P35 embroidery of the filament into the backing material 6 proceeds to loop around intended aperture 12d in a clockwise direction through point P36 before continuing generally diagonally across the material 6 and reaching point P37. From point P37 the embroidery apparatus loops the filament 10 around intended aperture 12a in a clockwise direction and reaches point P38 before embroidering the filament in a generally diagonal direction across the material 6 to reach point P39. From point P39 embroidery of the run continues to loop clockwise around intended aperture 12d before proceeding generally parallel to the plate's longitudinal midline through point P40 before reaching point P41. After reaching point P41, embroidery of the filament 10 continues to loop clockwise around intended aperture 12c, then continues through point P42 before diagonally crossing the material 6 and to reach point P43. After passing over P43, the embroidery run continues to loop clockwise around intended aperture 12b before passing through point P44 and continuing diagonally across the material 6, looping clockwise around intended aperture 12c and reaching point P45. Filament 10 embroidery then proceeds along a path generally perpendicular to the plate's longitudinal midline to reach point P46, and then loops clockwise around intended aperture 12a before reaching point P47. From point P47 embroidery of the filament 10 continues generally parallel to the plate's longitudinal midline to reach point P48, and then proceeds to loop clockwise around intended aperture 12b to point P49 before completing embroidery of the filament with a final run generally perpendicular to the longitudinal midline of the plate to reach point P35.

Although illustrated thusly, it can be appreciated by one skilled in the art that any variety of load bearing filament 10 configurations including any number of load bearing filament 10 strands embroidered to include fixation apertures 12a, 12b, 12c, 12d falls within the scope of the claimed invention. Furthermore, embroidery of the load bearing filament may begin at any number of points on the backing material with the resulting implant falling within the scope of the claimed invention.

Figure 14:
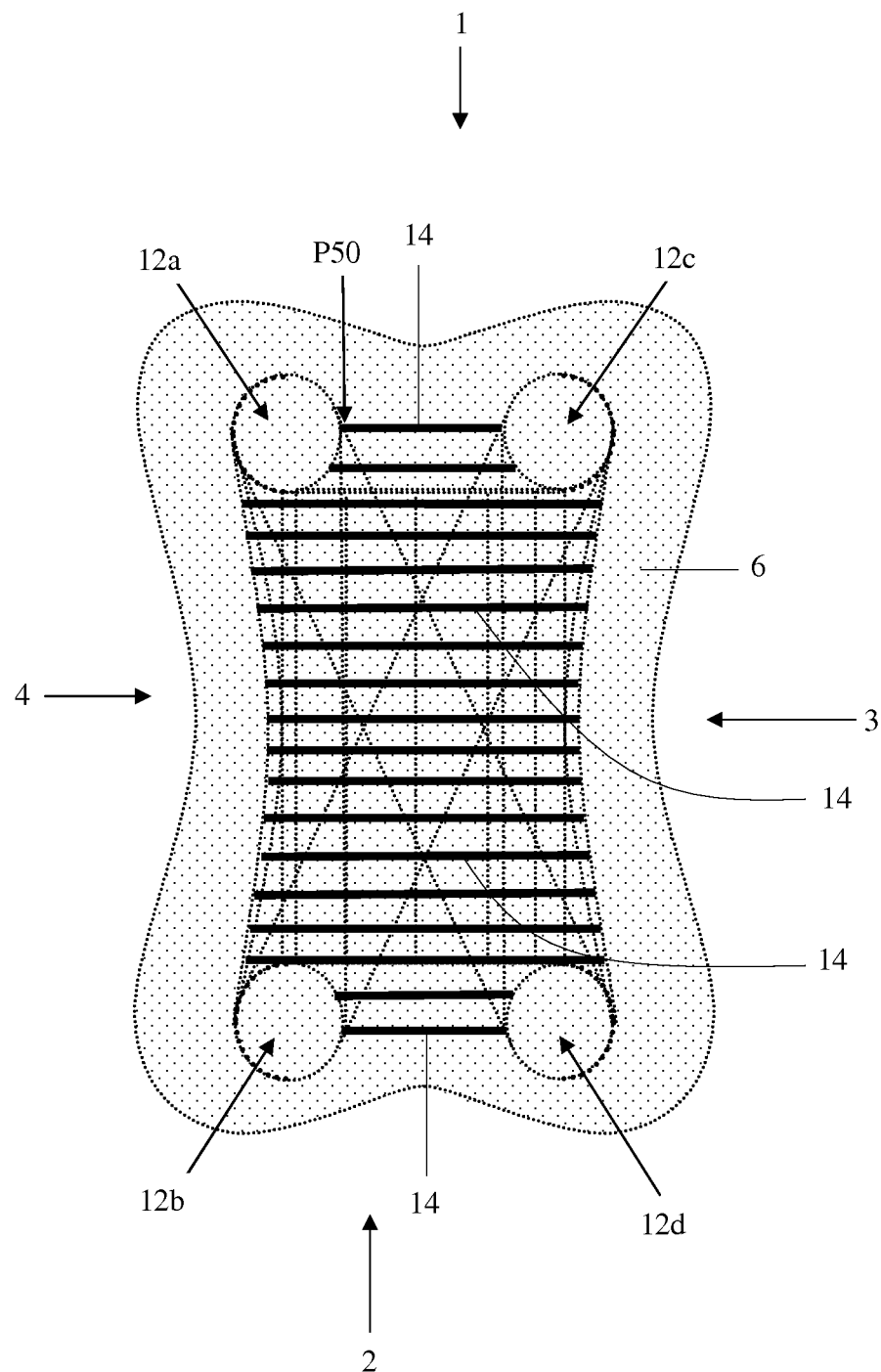
FIG. 14 is a top plan view of the backing material, aperture support filaments, longitudinal reinforcement filaments and load bearing filaments of FIG. 13 (shown in phantom) with horizontal reinforcement filaments embroidered thereon according to the present invention.

As illustrated in FIG. 14, embroidery of horizontal reinforcement filaments 14 into the backing material 6 commences upon completion of the embroidery of the load bearing filaments 10. The horizontal reinforcement filaments 14 support the structural integrity of the finished implant while additionally preserving the desired filament 10, 18, 22 orientation within the plate 8 matrix.

By way of example only, embroidery of the horizontal reinforcement filaments 14 may begin at a point P50 on aperture 12a closest to the longitudinal midline of the backing material. Embroidery of the filament 14 begins by engaging the aperture 12a border and then proceeding generally parallel to the backing material's first side 1 until arriving at and engaging aperture 12c. Once the predetermined number of embroidery passes has occurred over the first selected path, the embroidery apparatus shifts a predetermined distance toward side 2 and resumes embroidery by engaging a portion of aperture 12c, then proceeding to embroider generally linearly across the backing material 6 and potentially engaging any previously laid filaments 10, 18, 22 in the path until engaging the aperture border 12a. Embroidery of the horizontal reinforcement filaments 14 continues in the above manner until the embroidery apparatus has shifted to a point where apertures 12a, 12c are no longer present within the intended path of the subsequent embroidery pass. Subsequent passes then proceed between the outermost longitudinal reinforcement filaments 22 which define the lateral extent of the completed implant 8 and comprise the third 3 and fourth 4 plate sides. As described above, filament 14 embroidery continues with the embroidery apparatus shifting toward side 2 after stitching a predetermined number of filament 14 passes along the previously embroidered path, to again lay down a predetermined number of filament 14 passes before again shifting a predetermined distance toward side 2. Embroidery in the instantly above manner continues until the apertures 12b, 12d will fall within the subsequent intended embroidery pass of the filament 14. The subsequent filament 14 pass begins by example only, by engaging the proximate aperture 12b border, and proceeding linearly to engage the aperture 12d border. Following the same pattern of embroidery and apparatus shifting exemplified above, embroidery of the filament(s) continues until reaching a predetermined distance which conforms to a desired pattern of the manufacturer. Although presented in the above manner, embroidery of the horizontal reinforcement filaments 14 may be completed in any variety of steps which would result in an implant 8 comprising an array of support filaments 14 which extend generally parallel to said first and second sides and potentially between apertures 12a, 12b, 12c, 12d.

Figure 15:
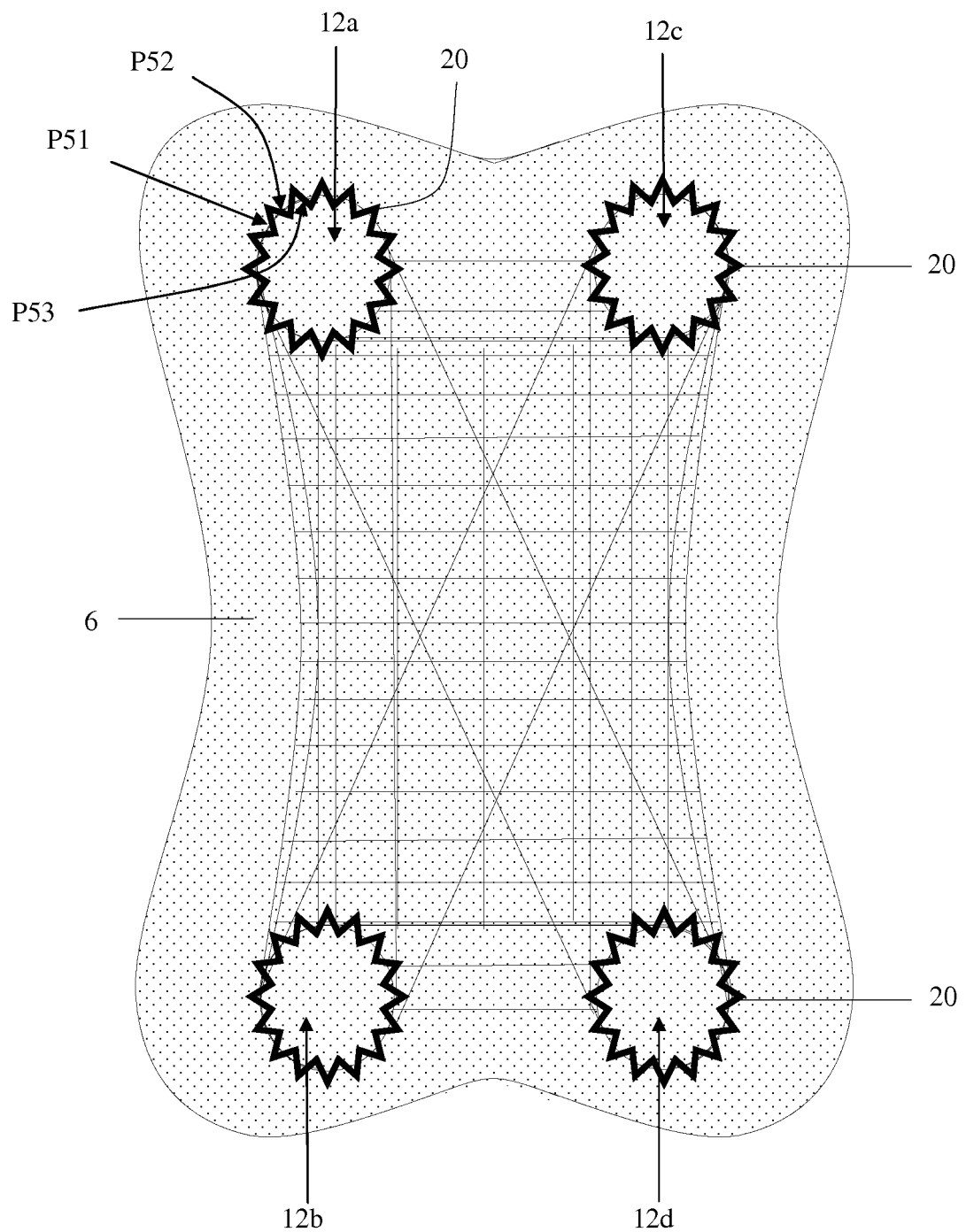
FIG. 15 is a top plan view of the backing material, aperture support filaments, longitudinal reinforcement filaments, load bearing filaments and horizontal reinforcement filaments of FIG. 14 (shown in phantom) with aperture reinforcement filaments embroidered thereon according to the present invention.

As illustrated in FIG. 15, the plate 8 is finally completed through embroidery of aperture reinforcement filaments 20 over the lengths of filaments 10, 22 which outline each of the fixation apertures 12a, 12b, 12c, 12d. The aperture reinforcement filaments 20 provide structural stability to and preserve preferred fixation aperture 12a, 12b, 12c, 12d orientation within the plate 8 matrix. Embroidery of aperture reinforcement filaments 20 of the present embodiment proceeds similar to that of the previous embodiment described above, leaving repetition of the process unnecessary.

By example only embroidery of the aperture reinforcement filament 20 of the present embodiment begins at a point P51 on the aperture 12a border filament by joining said filament 20 to said aperture border filament. Embroidery then continues along a predetermined pathway until the aperture 12a border filament is preferentially reinforced. For example only, embroidery of the filament 20 of the present embodiment proceeds from the embroidery origination point P51 by initiating an embroidery run away from the aperture 12a border filament for a predetermined distance along a line generally not perpendicular to the aperture's tangent at point P51 and potentially engaging any filament 10, 14, 18, 22 in its path. After reaching the predetermined distance away from the aperture 12a border filament, the embroidery run then returns along a path to engage the aperture 12a border filament at a point P52 clockwise from the origination point P51 and continues for a predetermined distance toward the aperture's 12a midpoint. Upon reaching a predetermined distance, the embroidery run returns to and engages the border 12a filament at a point P53 clockwise from the previous border filament engagement point P52. Repetition of the above process, stitching a run away from the aperture 12 border filament for a predetermined distance at a first angle, then returning at a second angle to engage the aperture 12a border filament, while progressing in a clockwise direction ultimately results in a star like pattern which may engage a plurality of filaments 10, 14, 18, 22 to ultimately provide the preferred performance characteristics demanded by a given implant scenario. Upon completing embroidery of the aperture reinforcement filament 20 for aperture 12a, embroidery of the remaining apertures 12b, 12c, 12d may be completed as described instantly above in any order including but not limited to 12b, 12c and then finally 12d. Although illustrated as a plurality of triangular embroidery paths extending from the aperture border, it can be appreciated that any number of passes of aperture support filaments 20 may be embroidered into the backing material 6 in any geometrical shape suitable for securing and preserving aperture 12a, 12b, 12c, 12d positioning and shape within the plate 8 matrix including but not limited to square, oval, circular, rectilinear, rhomboid and like shapes suitable for preferentially engaging surrounding filaments within the plate 8.

Figure 16:
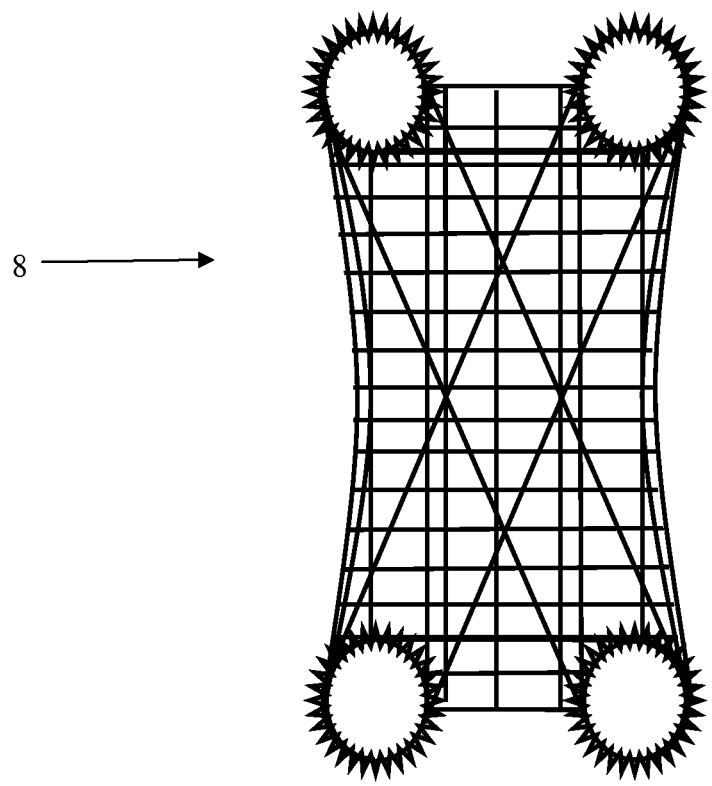
FIG. 16 is a top plan view of the textile-based plate implant of FIG. 15 with the backing material removed according to the present invention.
Figure 17:
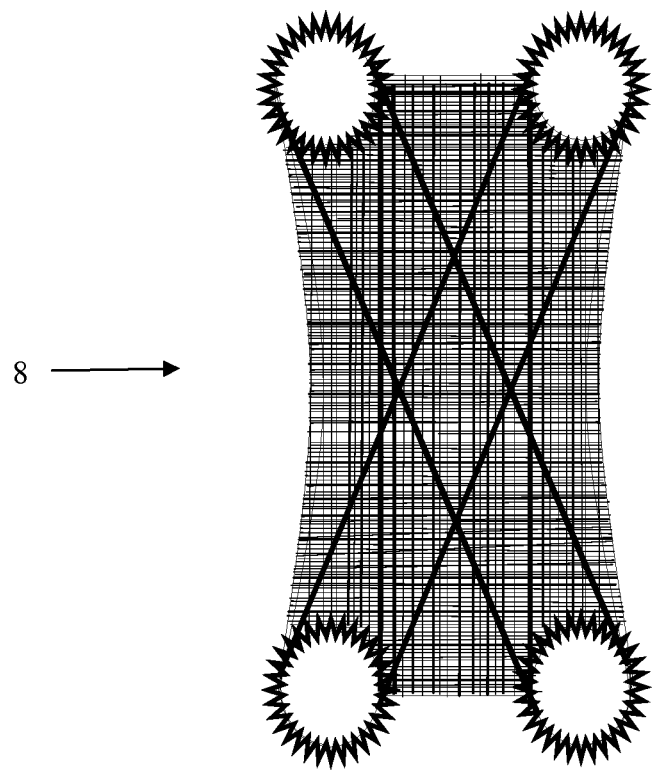
FIG. 17 is a top plan view of a textile-based implant of the type shown in FIG. 15 with an alternative filament density according to the present invention.

Upon completing inclusion of the preferred number of filaments 10, 14, 18, 20, 22 over the desired number of filament pathways, the backing material 6 is removed from the completed device, for example by dissolving the backing material 6 resulting in the finished implant 8 shown in FIG. 16. As illustrated in FIG. 17, alternative embodiments of the present invention may generally comprise an interconnected latticework of filaments provided through similar constructions methods resulting in a desired density as demanded by the given intended implantation site. The general appearance of the plate 8 may be altered by including more or less filler material.

Figure 18:
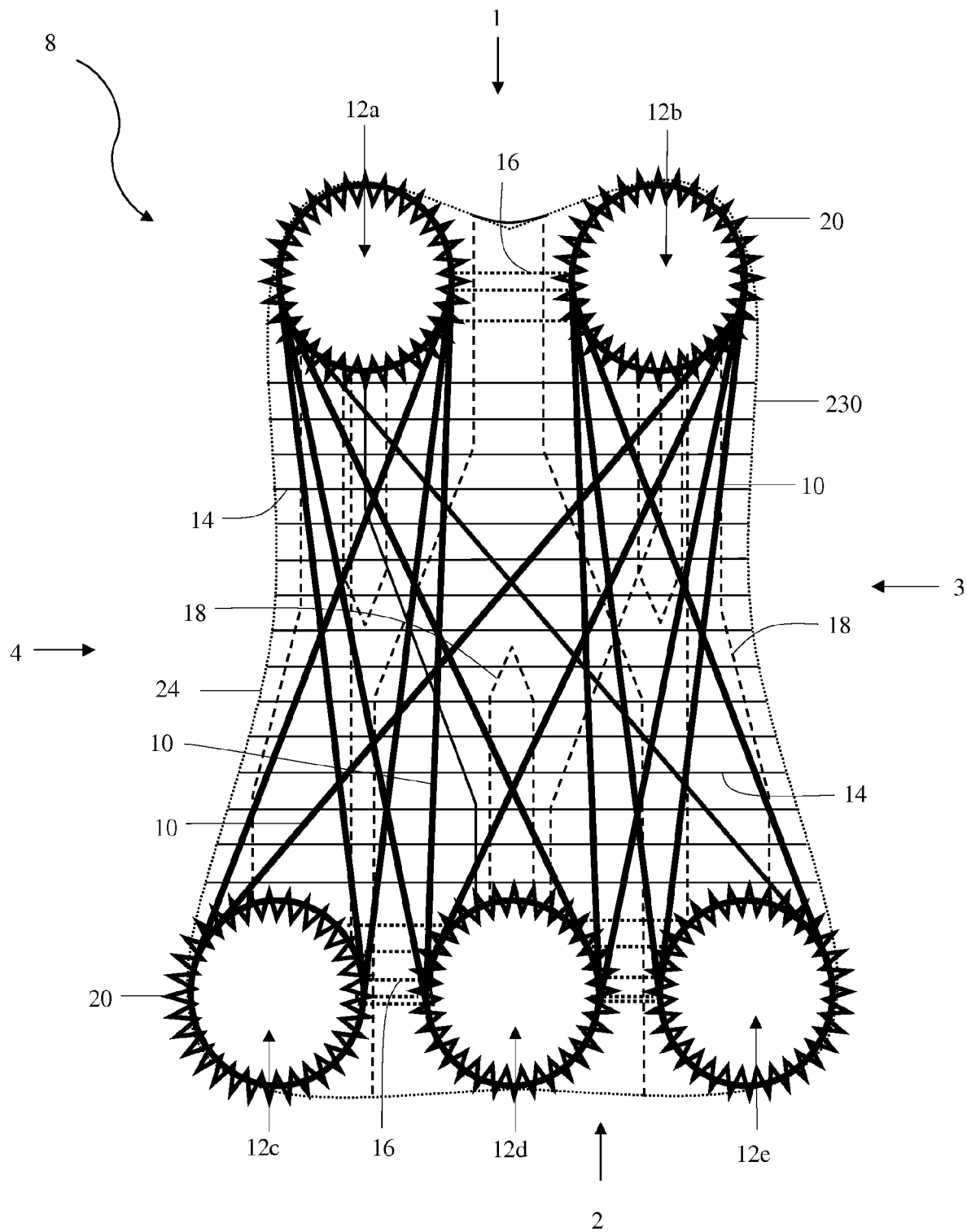
FIG. 18 is a top plan view of textile-based implant according to an alternative embodiment of the present invention having five screw apertures.

FIG. 18 illustrates a third embodiment of the present invention comprising a generally planar textile based plate 8 with four sides 1-4 dimensioned to preferentially align five fixation apertures 12a, 12b, 12c, 12d, 12e with the intended receiving tissues 5, 7 (FIG. 19) for insertion within the lumbar, thoracic and cervical regions of the spine. In the interest of clarity, each of the below elements are illustrated within FIG. 18 with a line quality common to that element type. Therefore, the use of dotted lines in this and other illustrations within the present application is not intended to denote various views generally attributed to the use of such lines. The present device comprises a latticework of filaments including load bearing filaments 10, horizontal reinforcement filaments 14, inter aperture support filaments 16, longitudinal reinforcement filaments 18, aperture reinforcement filaments 20 and a border filament 24 which together define the dimensions of the apertures 12a, 12b, 12c, 12d, 12e and the plate 8 itself.

Figure 19:
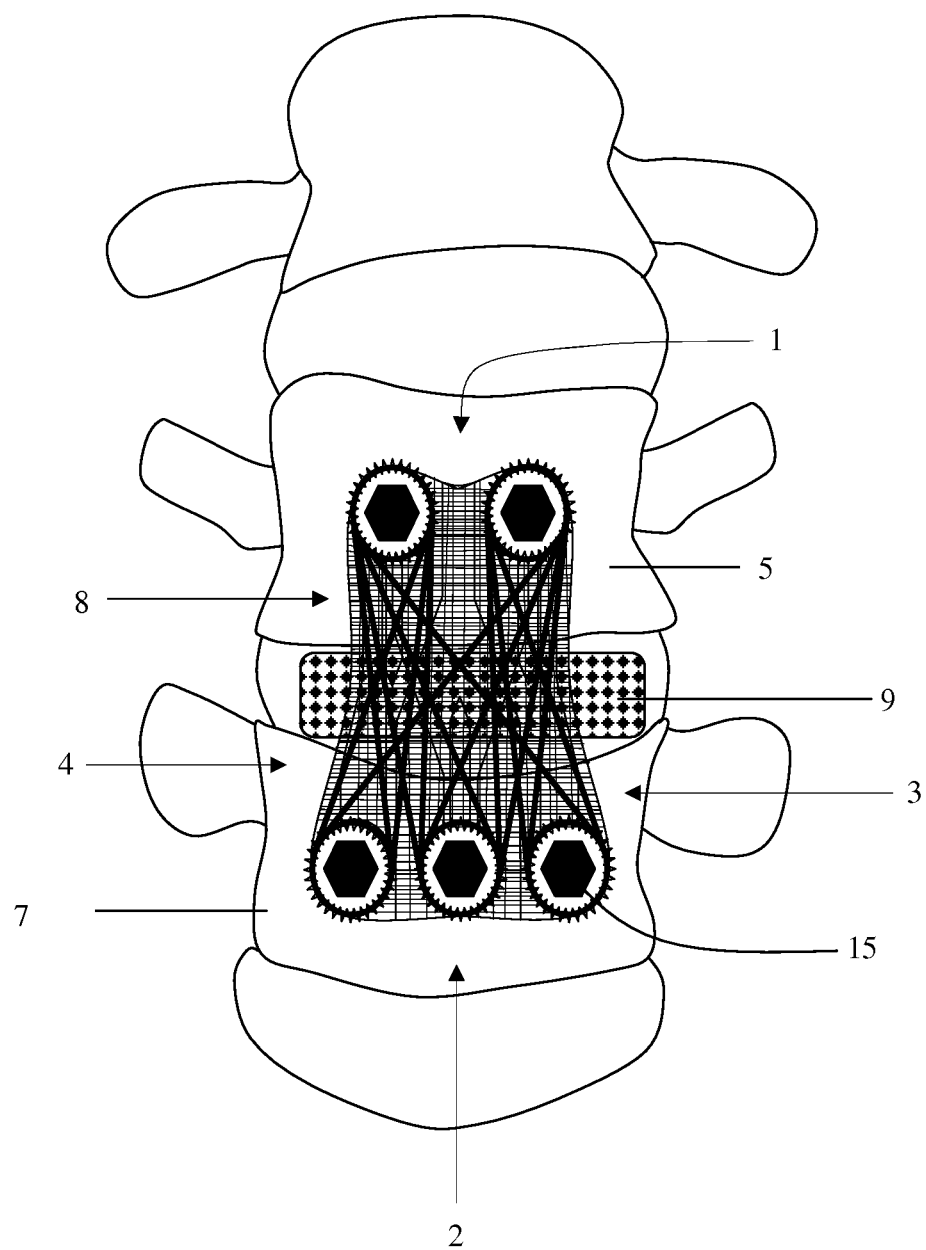
FIG. 19 is an anterior view of a human spine with the textile-based plate implant of FIG. 18 implanted onto the anterior faces of adjacent vertebral bodies and restricting a fusion implant within a disc space according to the present invention.

FIG. 19 illustrates, for example only, the present embodiment of the current invention after implantation onto anterior aspects of adjacent vertebral bodies 5, 7 and over an affected disc space. In the current example, the plate 8 restricts a therapeutic appliance 9 inserted within a disc space through an evacuated anteriorly oriented surgical corridor intruding within disc space. For example only, implantation of the plate 8 proceeds by aligning the first plate side 1 with an anterior surface of the superior vertebral body 5 adjacent to the disc space opening through which the previously placed therapeutic appliance 9 was inserted and resides, and orienting the remainder of the device to overlay the targeted disc space. Once preferentially positioned, fixation devices 15 including but not limited to screws, wires, sutures, rivets, nails and the like are inserted into fixation apertures 12a, 12b to selectively attach said first side 1 to the receiving tissue 5. Subsequent to fixation of the first side 1, implantation of the plate is completed by preferentially aligning the second plate side 2 with the anterior surface of the inferior vertebral body 7 adjacent to the disc space opening through which the therapeutic appliance 9 was inserted and resides. Once aligned, fixation devices 15 are selectively inserted through the apertures 12c, 12d, 12e and into the receiving tissue 7. Although illustrated as attached to an anterior aspect of adjacent vertebral bodies, it can be appreciated that the present embodiment of the current invention may be affixed to any number of desired tissues to effect a variety of therapeutic outcomes including but not limited to generally lateral, anterior and posterior vertebral surfaces. As can be appreciated, the sequence of fixation device 15 insertion through the apertures 12a, 12b, 12c, 12d, 12e may proceed in any desired sequence, with the apertures 12a, 12b, 12c, 12d, 12e aligned with any preferred receiving tissue with said alternative implantation methods falling within the scope of the present invention. Furthermore, the implant 8 may or may not be used in conjunction with complimentary therapeutic devices.

FIG. 20-26 illustrate sequentially one method of embroidery employed to construct the third exemplary embodiment of the present invention for use in the lumbar, thoracic or cervical region of the spine. To denote the sequence of embroidery leading to the completed implant, each of FIG. 20-25 illustrate the inclusion of an additional filament type within the backing material 6. Therefore, in the interest of clarity, the newly included filament in a given figure is denoted by an emboldened line, while filaments introduced in earlier figures of the present embodiment are denoted by light, dotted or dashed lines.

Figure 20:
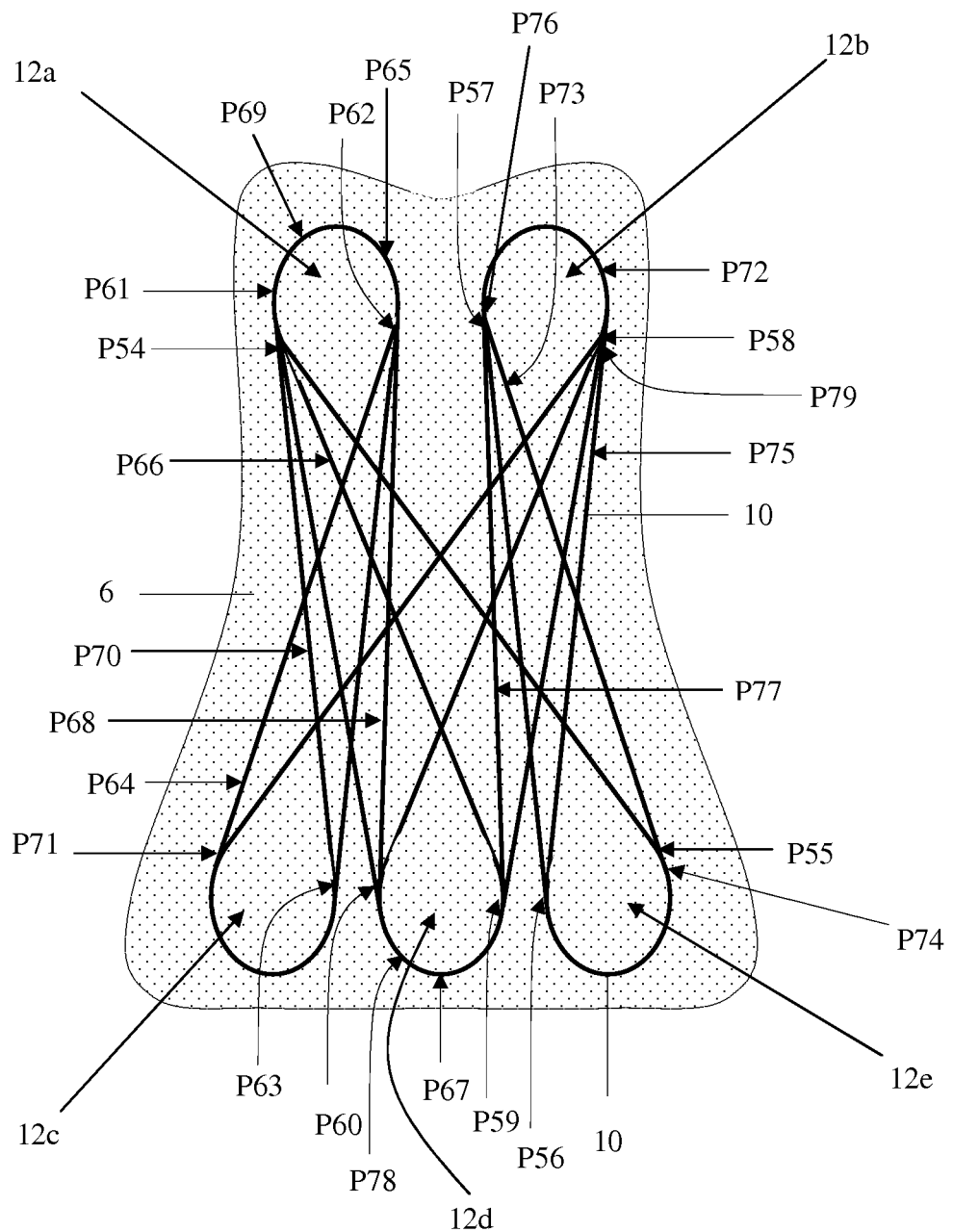
FIG. 20 is a top plan view of backing material with a load bearing filament embroidered thereon, forming part of the implant of FIG. 18 according to the present invention.

Referring to FIG. 20, the first step in manufacturing the current embodiment of the present invention is embroidery of the load bearing filament 10 onto the backing sheet 6. The load bearing filaments 10 of the present embodiment provide the primary source of load bearing capacity of the plate 8. Although embroidery of the load bearing filament 10 may be completed through embroidery of a set of individual load bearing filaments, as illustrated in the present example, a single filament 10 may be embroidered along a predetermined path which may include any number of fixation apertures 12a, 12b, 12c, 12d, 12e to comprise the preferred filament 10 configuration. For example only, embroidery of the filament 10 of the present embodiment proceeds following a predetermined path denoted in the present illustration as an ascending sequence of points P54-P79. Filament 10 embroidery into the backing material 6 of the present embodiment originates at point P54 of the backing material 6 proximate to intended aperture 12a, and continues diagonally across the backing material and through points P55 and P56 thus forming an outer border portion of intended aperture 12e. Embroidery of the filament continues generally parallel to the plate's longitudinal midline across the backing material, then through points P57 and P58 to form an outer border portion of intended aperture 12b. From P58 embroidery continues across the backing material 6 through points P59 and P60 thus forming the outer border portion of intended aperture 12d. Embroidery then proceeds across the material 6, passing over points P61 and P62 thus forming the outer portion of intended aperture 12a. Embroidery of the filament 10 then continues across the material 6 through points P63 and P64 thus forming an outer border portion of the intended aperture 12c. Embroidery of the filament 10 proceeds across the material 6 through points P65 and P66 to augment the outer border portion of intended aperture 12a. From point P66, the embroidery continues across the material 6 through points P67 and P68 to augment an outer border portion of intended aperture 12d. Continuing from point P68, filament embroidery passes through points P69 and P70 to augment an outer border portion of intended aperture 12a. Subsequently, embroidery through point P71 and then diagonally across the plate and through P72 results in augmentation of an outer border portion of intended aperture 12c. Embroidery of the filament 10 continues from point P72 through points P73 and P74 to form an outer portion of intended aperture 12b. From point P74, embroidery continues by looping around the outer portion of intended aperture 12e, then across the plate 8 and through points P75 and P76 to loop around the outer portion of intended aperture 12b. From point P76 embroidery of the filament 10 continues across the material 6, through point P77, then loops around the outer portion of intended aperture 12d through point P78 and finally completes the filament run at point P79 proximate to intended aperture 12b.

Figure 21:
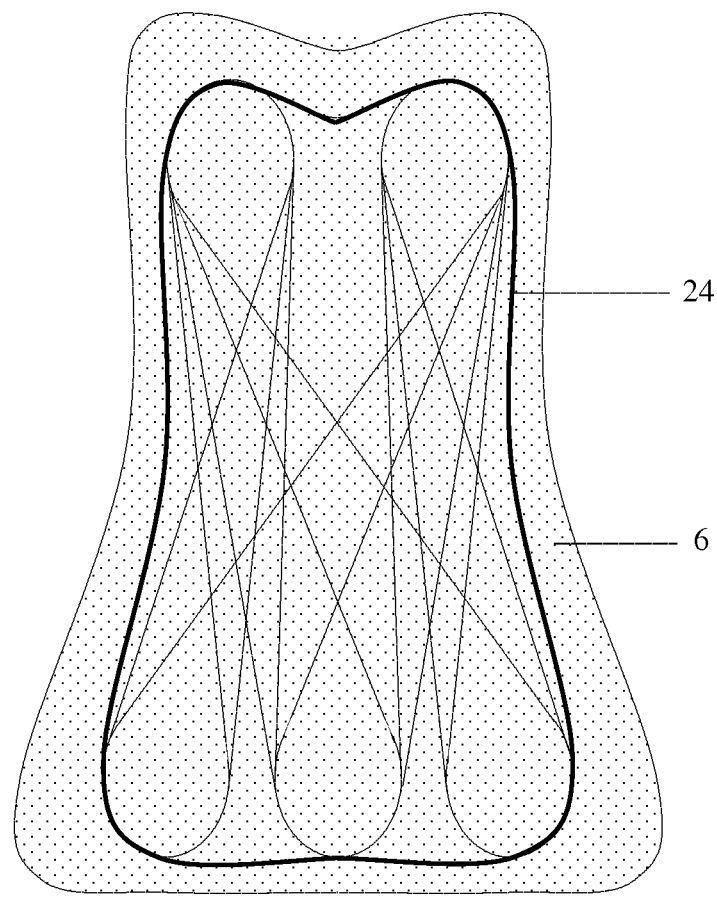
FIG. 21 is a top plan view of the backing material and load bearing filaments of FIG. 20 (shown in phantom) with border filaments embroidered thereon according to the present invention.

FIG. 21 illustrates the inclusion of a border filament 24 into the backing material as the next step in the manufacturing process of the present embodiment of the present invention. The border filament 24 is embroidered into the backing material 6 to provide structural support to and completely enclose the load bearing filaments 10 and subsequent filaments embroidered into the backing material 6 which will comprise the completed implant 8. Therefore the border filament is embroidered into the backing material 6 in a predetermined closed end configuration which will determine the intended planar dimensions of the implant, and generally conform to the outermost embroidered load bearing filaments 10. The path delineated by the first filament 24 run which outlines the implant 8, may then be embroidered over any number of times as desired by the manufacturer in order to meet the performance characteristics required by a given implant 8. Moreover, it can be appreciated that multiple border filament 24 runs may be made adjacent to the first border filament 24 run in order to provide alternative levels of stability to the device as required by the intended use of the implant 8.

Figure 22:
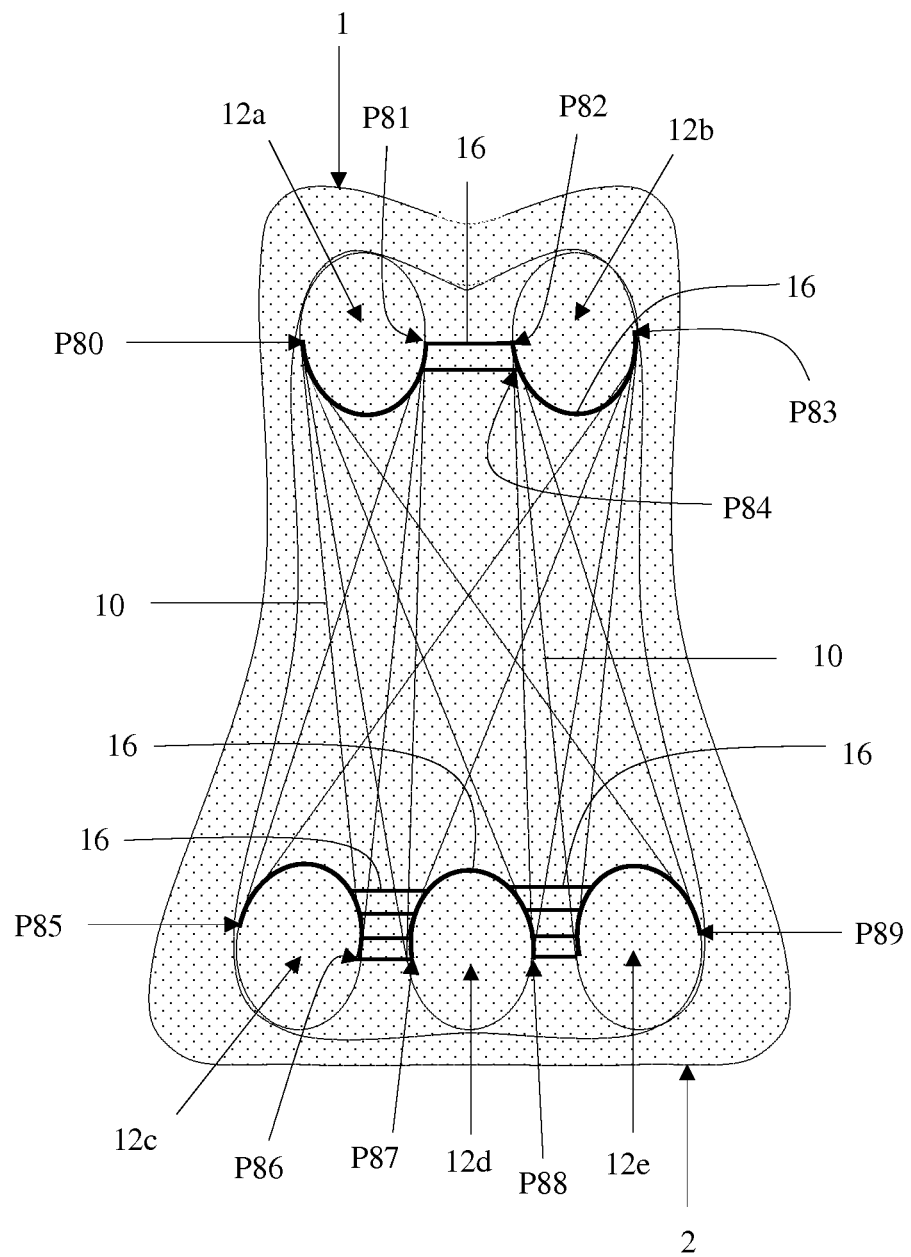
FIG. 22 is a top plan view of the backing material, load bearing filaments and border filaments of FIG. 21 (shown in phantom) with inter-aperture support filaments embroidered thereon according to the present invention.

FIG. 22 shows the inclusion of inter-aperture support filaments 16 embroidered within the backing material 6 as the next step in the process of manufacturing plate 8. The inter-aperture support filaments 16 generally complete the outline of the apertures 12a, 12b, 12c, 12d, 12e formed by the load bearing filament(s) 10, and support the integrity of the apertures within the plate 8 matrix. Generally, embroidery of the filaments 16 begins, by example only, by engaging a filament 16 to a portion of a load bearing filament 10 forming aperture border 12a at point P80. Embroidery of the filament 16 into the backing material 6 then proceeds along a predetermined path to trace the remaining borderless aperture 12a region, thus completing the aperture 12a formation by engaging a load bearing filament at point P81. The embroidery apparatus then proceeds to embroider the filament 16 on a generally linear path across the backing material 6 parallel to the first plate side 1 and eventually engaging a load bearing filament 10 comprising a portion of aperture border 12b at point P82. From this point P82, embroidery proceeds to complete aperture border 12b until engaging a load bearing filament 10 at point P83 to complete the aperture 12b border.

Upon completion of embroidery of the first filament 16 path, the embroidery apparatus shifts a predetermined distance toward the midpoint of the plate 8 and aligns with and engages a portion of the aperture 12b border at point P84. From this point P84, embroidery proceeds generally linearly across the backing material 6 parallel to said first plate side 1 to engage aperture 12a. Filament 16 embroidery continues in the above manner until a predetermined number of passes has been completed along a predetermined number of embroidery paths between the apertures 12a, 12b.

After embroidery of the inter aperture support filaments 16 between apertures 12a, 12b is completed, the embroidery apparatus shifts toward the plate's second side 2 to commence filament 16 embroidery between apertures 12c, 12d, 12e. Generally, embroidery of the filaments 16 continues, by example only, by engaging a portion of a load bearing filament 10 forming aperture border 12c at point P85. Embroidery of the filament 16 into the backing material 6 then proceeds along a predetermined path to outline the remaining undefined aperture 12c border portion, thus completing said aperture 12c formation by engaging a load bearing filament 10 at point P86. From point P86 embroidery proceeds generally parallel to said second plate side 2 until contacting and engaging a load bearing filament comprising a portion of the aperture 12d border at point P87. After engaging the load bearing filament 10, the embroidery apparatus proceeds to embroider the filament 16 into the backing material 6 along a predetermined path to complete the remaining undefined aperture 12d border via engagement of a filament 10 at point P88. From point P88, embroidery the of filament 16 continues along a predetermined path generally linearly and parallel to said second plate side 2 until reaching and engaging a load bearing filament 10 comprising a portion of aperture 12e. Upon engaging the filament 10, embroidery of the inter aperture support filament 16 continues along a predetermined path to complete the undefined portion of the aperture border 12e, until ultimately reaching and engaging the load bearing filament 10 at point P89.

After completing the above described first filament 16 pass, the embroidery apparatus shifts toward the midline of the plate to embroider a predetermined number of filaments 16 over a predetermined number of filament 16 paths parallel to said second plate side and between aperture 12c, 12d, 12e borders. For example only, after shifting toward the plate 8 midline, the embroidery apparatus aligns with the aperture 12c border at a point more proximate to the longitudinal plate midline, and proceeds to embroider along a predetermined path until reaching and engaging aperture border 12d. The embroidery apparatus then shifts a predetermined distance toward the plate 8 midpoint, aligns with and engages the aperture 12d border, and embroiders a filament 16 run until reaching and engaging the aperture 12c border. Embroidery of the filaments 16 continues in the above described manner until a predetermined number of filament 16 passes are embroidered between the aperture pair 12c-12d. Once a preferred number of filaments 16 are laid over a predetermined number of filament paths between the aperture pair 12c-12d, the embroidery apparatus shifts to align with a point on aperture 12d more proximate to the plate's third side 3 to commence embroidery of filaments 16 between aperture pair 12d-12e.

Completion of embroidery of the inter aperture support filaments 16 is achieved through repetition of the above mentioned method describing embroidery of the filament 16 between aperture pair 12c-12d between the remaining aperture pair 12c-12d. Although the plate 8 as illustrated above includes a definite number and configuration of filaments 16, it can be appreciated by one skilled in the art will recognize that plates 8 comprising any number of suitable filament 16 runs over any number of desired filament 16 pathways will fall within the scope of the present invention. Furthermore, although embroidery of the inter aperture support filament 16 is described in the above sequential method, any number of filament embroidery path sequences may be utilized to achieve desired filament orientation and filament 16 density within the plate 8 matrix.

Figure 23:
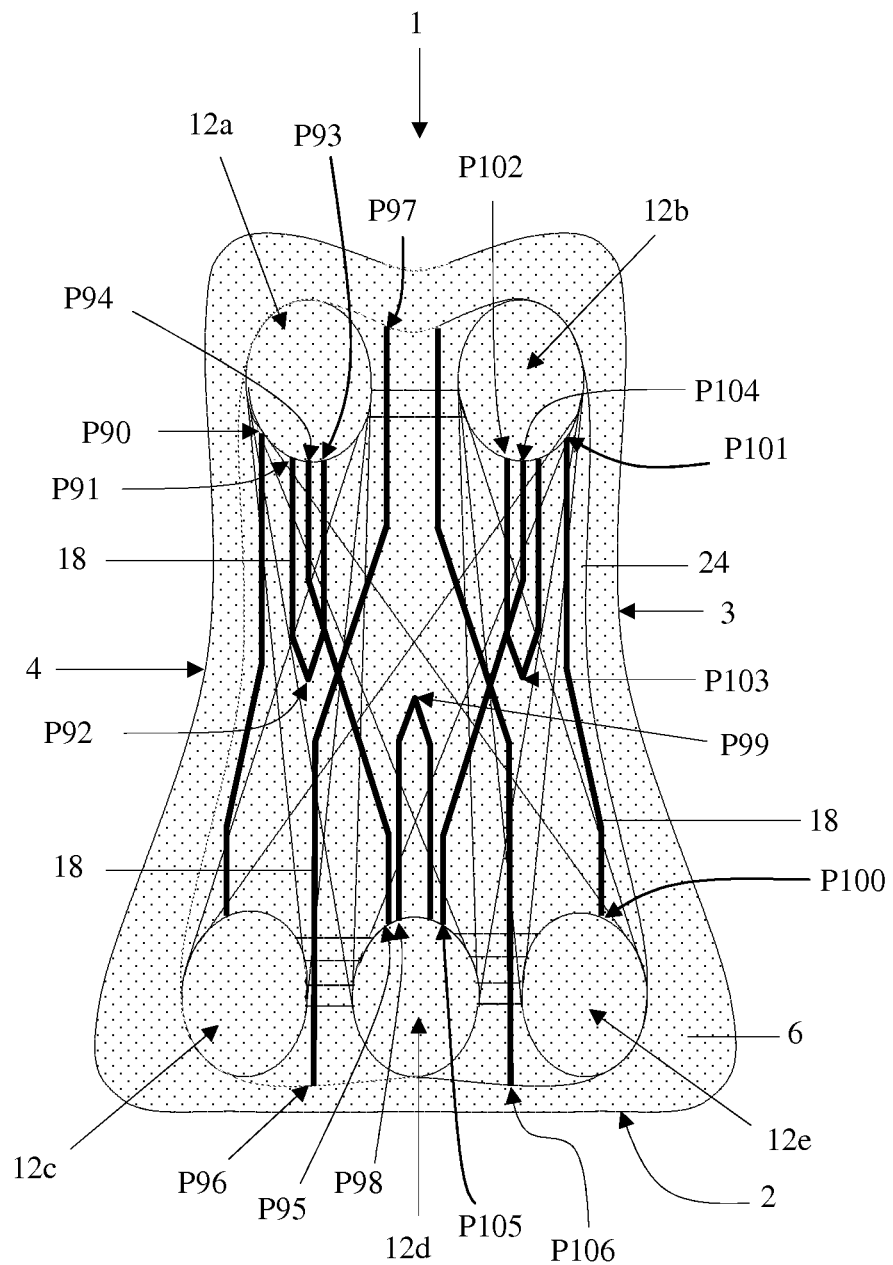
FIG. 23 is a top plan view of the backing material, load bearing filaments, border filaments and inter-aperture support filaments of FIG. 22 (shown in phantom) with longitudinal reinforcement filaments embroidered thereon according to the present invention.

As shown in FIG. 23, construction of the present embodiment of the plate 8 continues with the embroidery of longitudinal reinforcement filaments 18 onto the backing material 6. The longitudinal reinforcement filaments 18 provide structural support for the aperture 12a, 12b, 12c, 12d, 12e borders while concurrently providing support to the load bearing filaments 10.

Generally the longitudinal support filaments 18 of the present embodiment are embroidered over a predetermined number of pathways aligned generally parallel to the longitudinal midline of the plate and may engage previously embroidered filaments 10, 16, 24 intersecting the intended filament 18 path.

For example only embroidery of the filaments 18 commence at a point P90 proximate to the plate's fourth side 4 by engaging a filament 18 origin to the aperture 12a border. Filament 18 embroidery then proceeds generally linearly and parallel to the plate's 8 longitudinal midline until reaching and engaging the aperture border 12c. After completing the preceding embroidery run, the embroidery apparatus then shifts toward the plate's third side 3 aligning the stitching element with a point P91 on the aperture 12a border. A filament 18 is then stitched to engage the aperture 12a border, and subsequently embroidered into the backing material 6 over a predetermined path until reaching a point P92 within the plate 8 matrix. Upon reaching the point P92, embroidery of the filament 18 follows a predetermined path returning to engage the aperture 12a border at some point P93 more proximate to the plate's third side 3 than the instantly described run's origin at point P91.

Upon completion of embroidery of the preceding filament 18, the embroidery apparatus shifts a predetermined distance toward the plate's fourth side 4 and aligns with a point P94 on the aperture border 12a. Embroidery proceeds generally linearly from the point P94, across the plate 8 matrix toward and ultimately engaging the aperture 12d border at a point P95 between the plate's longitudinal midline and fourth side 4. After completing the above described embroidery pass, the embroidery apparatus then shifts a predetermined distance toward the plate's fourth side 4 and aligns with the border filament 24 at a point P96 between the apertures 12c, 12d in preparation of the next embroidery run.

Embroidery of another filament 18 into the backing material 6 then proceeds by stitching the filament 18 to engage the border filament 24 at point P96 and commencing an embroidery run along a predetermined path generally parallel to the longitudinal midline of the plate 8 and extending to and ultimately engaging the border filament 24 at a point P97 between the apertures 12a, 12b. Upon completion of embroidery of the instantly above described filament 18 pathway, the embroidery apparatus shifts to a point P98 on the aperture 12d border between the plate's longitudinal midline and fourth side 4 to initiate another embroidery run.

Embroidery of the subsequent filament 18 pathway begins at point P98 by engaging the filament origin with the aperture 12d border and then progressing to embroider generally linearly toward the midpoint of plate 8 until reaching a predetermined point P99. Upon reaching the point P99, embroidery of the filament 18 follows a predetermined path returning to engage the aperture 12d border at some point between the longitudinal midline and third side 3 of plate. Upon completion of the instantly above described embroidery run, the embroidery apparatus shifts to align with a point P100 on the aperture 12e border to begin another embroidery run over a predetermined pathway.

Embroidery of the subsequent longitudinal reinforcement filament 18 begins by engaging a filament 18 origin with the aperture 12e border proximate to the plate's third side 3 at point P100. Filament 18 embroidery then proceeds generally linearly and parallel to the plate's 8 longitudinal midline until reaching and engaging the aperture border 12b at point P101 proximate to the plate's third side 3. After completing the preceding embroidery run, the embroidery apparatus then shifts toward the plate's longitudinal midline, and aligns the stitching element with a point P102 on the aperture 12b border. A filament 18 origin is then stitched to engage the aperture 12b border at point P102, and subsequently the filament 18 is embroidered into the backing material 6 over a predetermined path until reaching a point P103 within the plate 8 matrix. Upon reaching the point P103, embroidery of the filament 18 follows a predetermined path returning to engage the aperture 12b border at some point more proximate to the plate's third side 3 than the instantly described run's origin at point P103.

Upon completion of embroidery of the preceding filament 18, the embroidery apparatus shifts a predetermined distance toward the plate's fourth side 4 and aligns with a point P104 on the aperture border 12b. Embroidery proceeds from point P104 generally linearly across the plate 8 matrix toward and ultimately engaging the aperture 12d border at a point P105 between the plate's longitudinal midline and third side 3. After completing the above described embroidery pass, the embroidery apparatus then shifts a predetermined distance toward the plate's third side 3 and aligns with the border filament 24 at a point P106 between the apertures 12c, 12d in preparation of the next embroidery run.

Embroidery from point P106 of the filament 18 into the backing material 6 then proceeds by stitching the filament 18 origin to engage the border filament 24 at point P106 and commencing an embroidery run along a predetermined path generally parallel to the longitudinal midline of the plate 8 and extending to and ultimately engaging the border filament 24 at a point between the apertures 12a, 12b.

Although embroidery of the longitudinal reinforcement filaments 18 are described above as depositing a single filament 18 over each intended filament 18 pathway, it can be appreciated by one skilled in the art that a device containing any number of filament 18 passes provided for any number of predetermined filament 18 embroidery paths will result in a device falling within the scope of the present invention.

Figure 24:
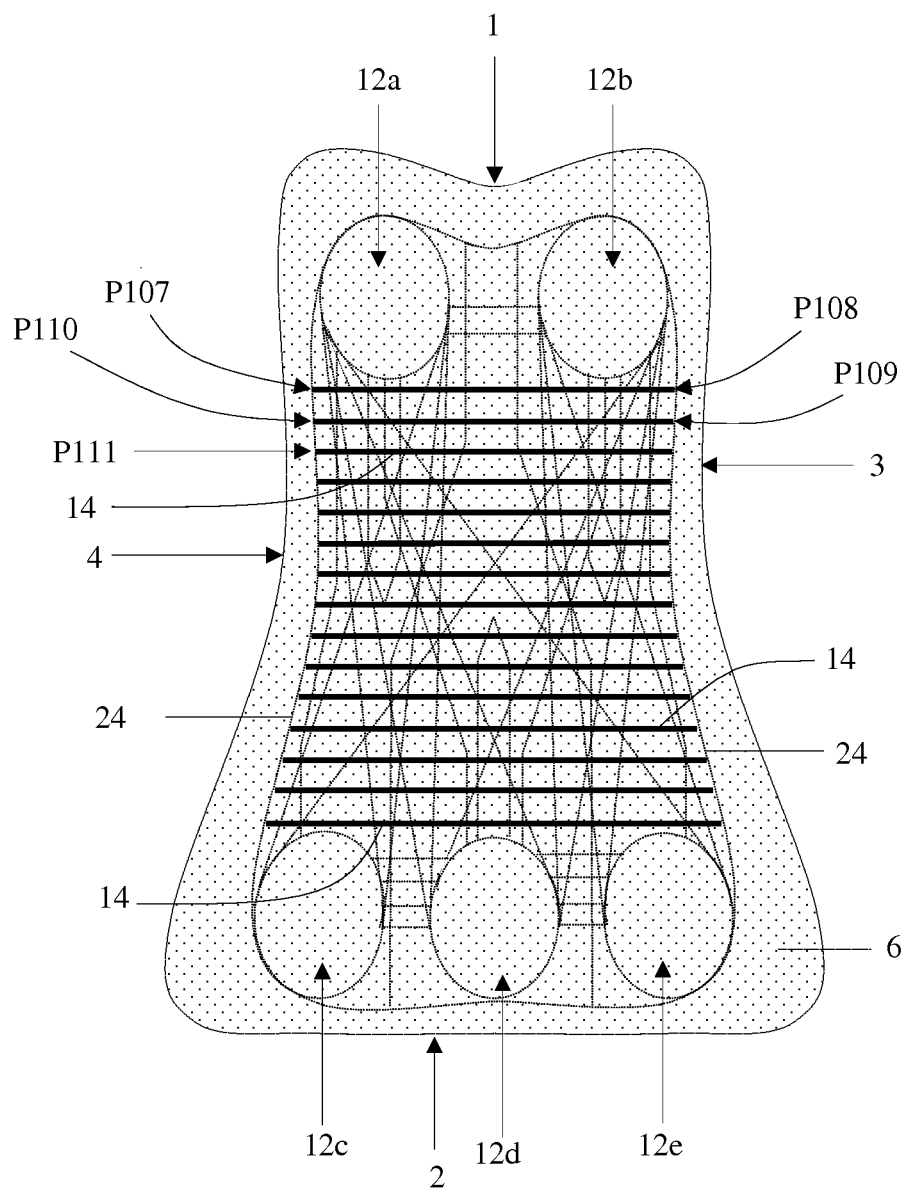
FIG. 24 is a top plan view of the backing material, load bearing filaments, border filaments, inter-aperture support filaments and longitudinal reinforcement filaments of FIG. 23 (shown in phantom) with horizontal reinforcement filaments embroidered thereon according to the present invention.

FIG. 24 illustrates the embroidery of horizontal reinforcement filaments 14 into the backing material as the next step in the construction of the implant 8 of the present embodiment. The horizontal reinforcement filaments 14 generally support preferred filament 10, 16, 18, 24 orientations within the plate 8 matrix while concomitantly providing load bearing support to the completed implant 8. Regularly the horizontal reinforcement filaments 14 of the present embodiment are embroidered into the backing material 6 region between the aperture pair 12a-12b and aperture set 12c, 12d, 12e, and along generally linear pathways parallel to the second plate side 2. For example only, embroidery of the horizontal reinforcement filaments 14 begins with the embroidery apparatus aligning with a point P107 along the border filament 24 proximate to aperture 12a, and stitching the filament 14 to engage said filament 24. After engagement of the filament 24, embroidery of the filament proceeds across the backing material 6 generally parallel to the plate's second side 2 until reaching and engaging the border filament 24 proximate to the plate's third side 3 at point P108. After laying a predetermined number of filament passes over the embroidery path described instantly above, the embroidery apparatus shifts a predetermined distance toward the plate's second side 2 to align with the border filament 24 at a point P109 for example only, proximate to the plate's third side 3. Once properly aligned, the embroidery apparatus joins a filament 14 to the border filament 24 at point P109 and proceeds to embroider the filament 14 into the backing material 6 along a predetermined path parallel to the plate's second side 2 until reaching and joining the filament 14 with the border filament 24 at point P110. After embroidering a predetermined number of embroidery passes over the instantly above described pathway, the embroidery apparatus shifts a predetermined distance toward said second plate side 2 and aligns with a point P111 along the filament border 24 proximate to said fourth plate side 4.

Embroidery of a predetermined number of filament 14 embroidery passes over a predetermined number of intended filament pathways continues in the above described method until the preferred number of filaments 14 are embroidered over a preferred number of pathways within the plate 8 as demanded by a given implantation scenario. Furthermore, as embroidery of the filament 14 proceeds across the backing material 6, any number of filaments 14 may be stitched to engage filaments 10, 18, 24 at a variety of loci so as to provide the finished implant 8 with preferential performance characteristics.

Figure 25:
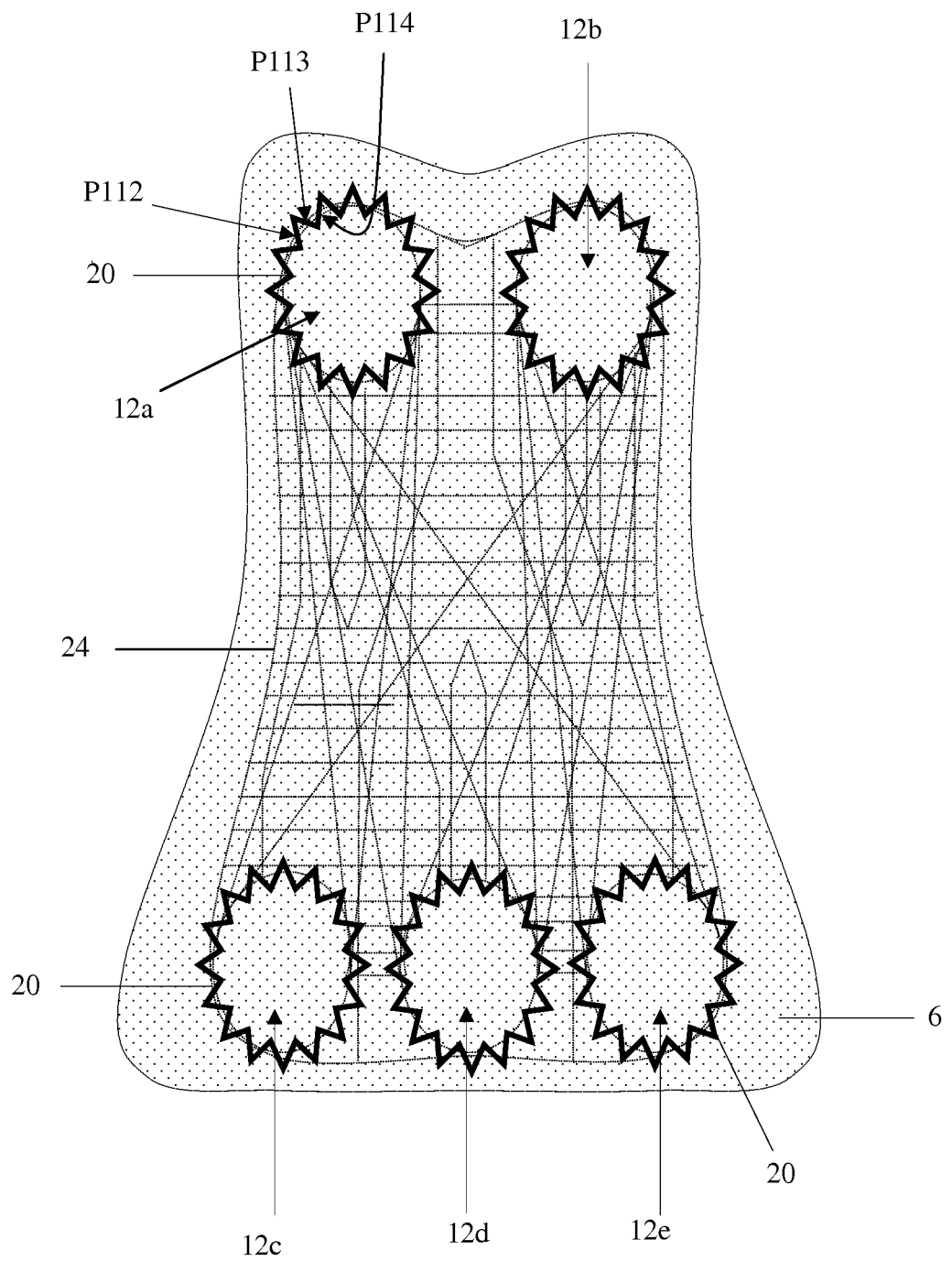
FIG. 25 is a top plan view of the backing material, load bearing filaments, border filaments, inter-aperture support filaments, longitudinal reinforcement filaments and horizontal reinforcement filaments of FIG. 24 (shown in phantom) with aperture reinforcement filaments embroidered thereon according to the present invention.

As shown in FIG. 25, the final step in the construction of the present plate 8 embodiment is completed through embroidery of aperture reinforcement filaments 20 over the lengths of filaments 10, 16, 24 (hereinafter collectively called the aperture border filament) which outline each of the fixation apertures 12a, 12b, 12c, 12d 12e. The aperture reinforcement filaments 20 provide structural integrity to each aperture 12a, 12b, 12c, 12d, 12e border while concomitantly transferring loads experience by the load bearing filaments 10 to the fixation device 15 inserted within each aperture 12a, 12b, 12c, 12d, 12e. By example only embroidery of the aperture reinforcement filament 20 of the present embodiment begins at a point P112 on the aperture 12a border filament by joining said filament 20 to said aperture border filament. Embroidery then continues along a predetermined pathway until the aperture 12a border filament is preferentially reinforced. For example only, embroidery of the filament 20 of the present embodiment proceeds from the embroidery origination point P112 by initiating an embroidery run away from the aperture 12a border filament for a predetermined distance along a line generally not perpendicular to the aperture's tangent at point P112 while engaging any filament 10, 14, 16, 18, 24 in its path. The embroidery run then returns along a path to engage the aperture 12a border filament at a point P113 clockwise from the origination point P112 and continues for a predetermined distance toward the aperture's 12a midpoint. Upon reaching a predetermined distance, the embroidery run proceeds to return to and engage the border 12a filament at a point P114 clockwise from the previous engagement point P113. Repetition of the above process, stitching a run away from the aperture 12 border filament for a predetermined distance at a first angle, then returning at a second angle to engage the aperture 12a border filament, while progressing in a clockwise direction ultimately results in a star like pattern which may engage a plurality of filaments 10, 14, 16, 18, 24 to provide the preferred performance characteristics of a given implant scenario. Upon completing embroidery of the aperture reinforcement filament 20 for aperture 12a, embroidery of the remaining apertures 12b, 12c, 12d, 12e may be completed as described instantly above in any order including but not limited 12b, 12c, 12d then finally 12e. Although illustrated as a plurality of triangular extensions from the aperture border, it can be appreciated that any number of passes of aperture support filaments 20 may be embroidered into the backing material 6 in any geometrical shape suitable for securing and preserving aperture 12a, 12b, 12c, 12d, 12e positioning and shape within the plate 8 matrix including but not limited to square, oval, circular, rectilinear, rhomboid and like shapes suitable for preferentially engaging surrounding filaments within the plate 8.

Figure 26:
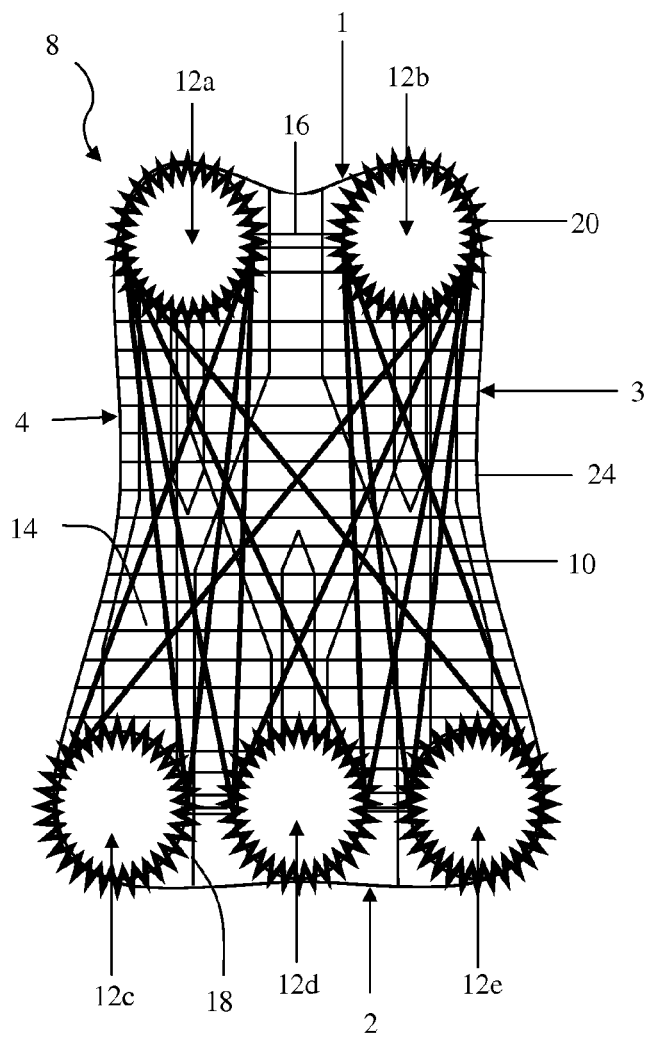
FIG. 26 is top plan view of the textile-based plate implant of FIG. 25 with the backing material removed according to the present invention.
Figure 27:
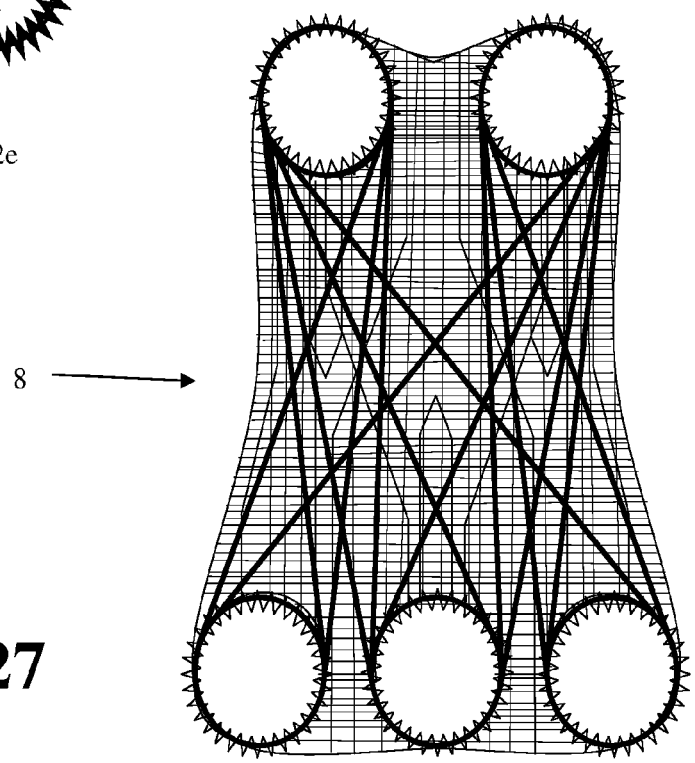
FIG. 27 is a top plan view of a textile-based plate implant of the type shown in FIG. 25 having an alternative filament density according to the present invention.

Upon completing inclusion of the preferred number of filaments 10, 14, 18, 20, 24 over the desired number of filament pathways, the backing material 6 is removed from the completed device, for example by dissolving the backing material 6 resulting in the finished implant 8 shown in FIG. 26. As illustrated in FIG. 27, alternative embodiments of the present invention may generally comprise an interconnected latticework of filaments provided through similar constructions methods resulting in a desired density as demanded by the given intended implantation site. The general appearance of the plate 8 may be altered by including more or less filler material.

Figure 28:
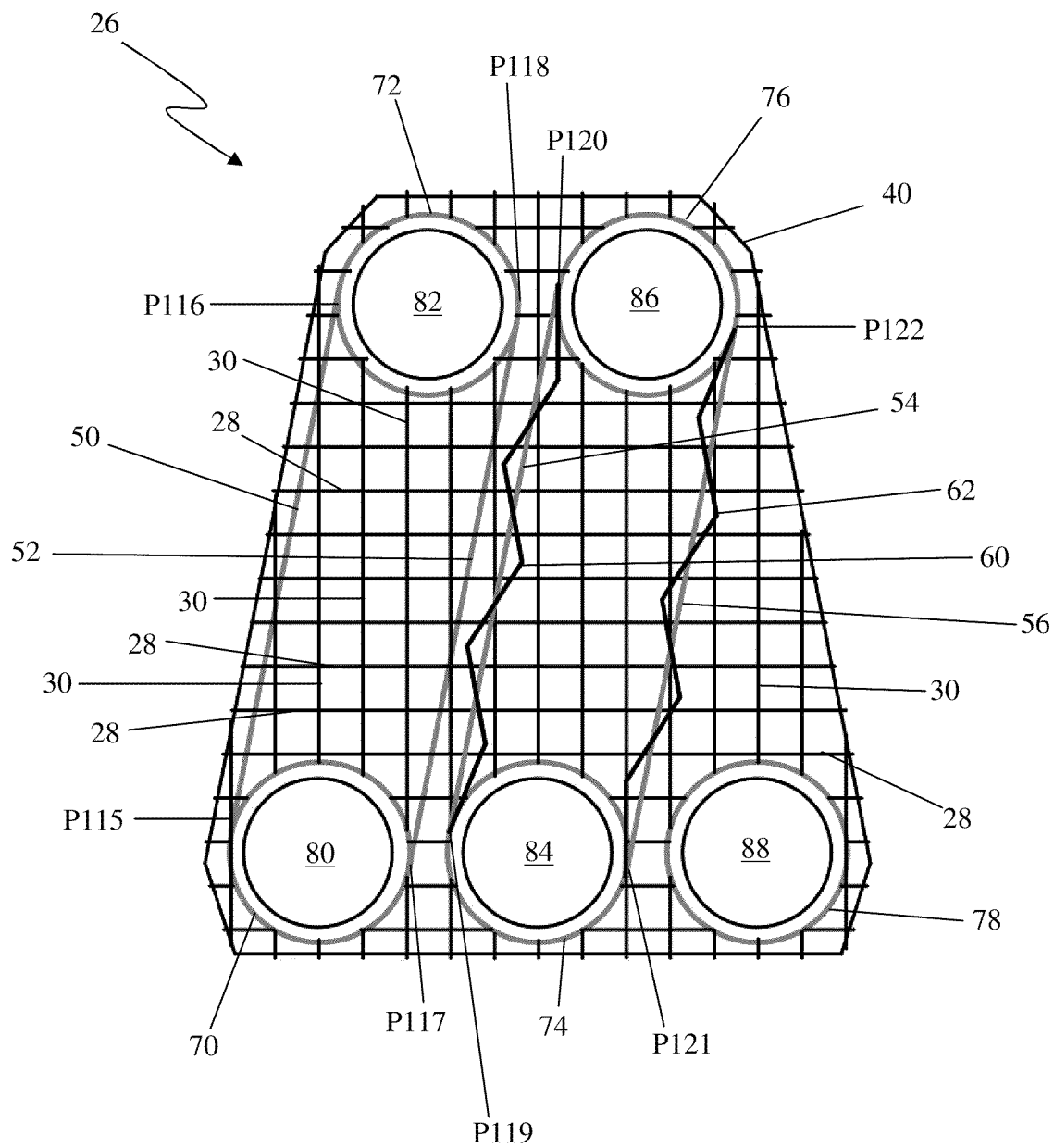
FIG. 28 is a top plan view of an embroidered structure having both straight load bearing filaments and zigzag load bearing filaments used to create a bi-modic tension feature, according to one embodiment of the present invention.
Figure 29:
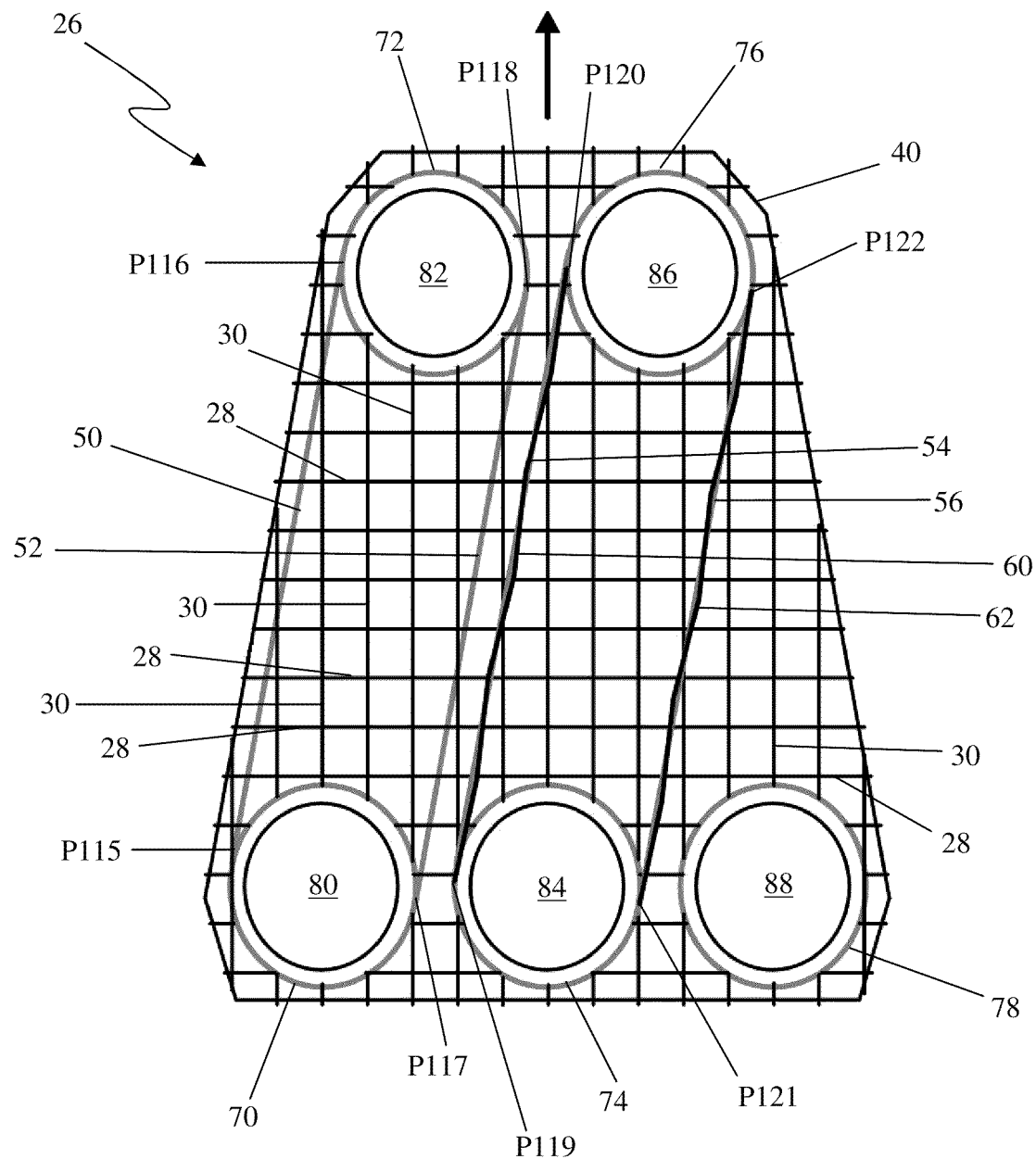
FIG. 29 is a top plan view of the embroidered structure of FIG. 28, showing how the zigzag load bearing filaments straighten after the embroidered structure has been stretched.

FIGS. 28 & 29 illustrate a multi-modic embroidered plate 26 manufactured according to one embodiment of the present invention. Embroidered plate 26 may be used in a variety of surgical applications, including but not limited to spine surgery. By way of example only, embroidered plate 26 may be used as a textile plate to add stabilization to an artificial disc implanted in an intervertebral disc space (not shown). Acting as a textile plate, embroidered plate 26 stabilizes the intervertebral level around an implanted artificial disc. Embroidered plate 26 may be manufactured via an embroidery process similar to that shown and described in commonly owned and co-pending U.S. patent application Ser. No. 11/968,157 entitled "Using Zigzags to Create Three-Dimensional Embroidered Structures" filed Dec. 31, 2007, the complete disclosure of which is hereby incorporated by reference into this disclosure as if set forth fully herein.

The embodiment of FIGS. 28 & 29 includes a base set of thread fibers arranged in a straight grid pattern. More specifically, FIGS. 28 & 29 depict a generally trapezoidal area of biaxial embroidered construction formed with straight thread pairs 28 and enclosed by straight enclosing thread pairs 30 to form the embroidered structure 26. The generally trapezoidal area is bounded by a rigid embroidered border 40 within which the thread pairs 28 and enclosing thread pairs 30 are orthogonal to each other on paths defined by the shortest distance between the endpoints of each thread pair 28 or enclosing thread pair 30. Embroidered plate 26 also includes straight load bearing filaments 50-56, zigzag load bearing filaments 60-62, aperture reinforcement filaments 70-78, and apertures 80-88 dimensioned to receive screws or other affixation elements. Aperture reinforcement filaments 70-78 are generally circular in shape, outlining each fixation apertures 80-88, respectively. Aperture reinforcement filaments 70-78 provide structural integrity to each aperture 80-88, while transferring loads experienced by the load bearing filaments 50-56, 60-62 to the fixation device (not shown) inserted within each aperture 80-88.

Straight load bearing filaments 50-56 and zigzag load bearing filaments 60-62 both provide load bearing strength to the embroidered structure 26 and preferentially limit extension across the affected joint or intervertebral disc space. By way of example only, straight load bearing filaments 50-56 are positioned such that two straight thread paths pass diagonally from aperture 80 to aperture 382 and two straight thread paths pass diagonally from aperture 84 to aperture 86. More specifically, one straight load bearing filament 50 engages on the lateral side of the aperture reinforcement filament 70 at point P115 and passes on a straight diagonal thread path to connect to the lateral side of the aperture reinforcement filament 72 at point P116. A second straight load bearing filament 52 engages on the medial side of the aperture reinforcement filament 70 at point P117 and passes on a straight diagonal thread path to connect to the medial side of the aperture reinforcement filament 72 at point P118. A third straight load bearing filament 54 engages on the medial side of the aperture reinforcement filament 74 at point P119 and passes on a straight diagonal thread path to connect to the medial side of the aperture reinforcement filament 76 at point P120. A fourth straight load bearing filament 56 engages on the lateral side of the aperture reinforcement filament 74 at point P121 and passes on a straight diagonal thread path to connect to the lateral side of the aperture reinforcement filament 76 at point P122.

By way of example only, zigzag load bearing filaments 60-62 are superimposed on top of straight load bearing filaments 54-56 and are positioned such that two thread paths pass diagonally from aperture 84 to aperture 86. More specifically, one zigzag load bearing filament 60 engages on the medial side of the aperture reinforcement filament 74 at point P119 and passes on a zigzagged diagonal thread path to connect to the medial side of the aperture reinforcement filament 76 at point P120; and a second zigzag load bearing filament 62 engages on the lateral side of the aperture reinforcement filament 74 at point P121 and passes on a zigzagged diagonal thread path to connect to the lateral side of the aperture reinforcement filament 76 at point P122.

Straight load bearing filaments 50-56 create an initial limit to the extension of the embroidered structure 26 under a load. The embroidered structure 26 with straight load bearing filaments 50-56 keep the intervertebral disc space stable while tissue ingrowth takes place throughout part or all of the embroidered structure 26 (as desired). Over time with repeated loading of the embroidered structure 26, the straight load bearing filaments 50-56 may stretch out. At this point, the zigzag load bearing filaments 60-62 may then act as a second limit on the extension of the embroidered structure 26. Zigzag load bearing filaments 60-62 may be comprised of a stronger set of threads than straight load bearing filaments 50-56. Zigzag load bearing filaments 60-62 have the capacity to further limit the extension of the embroidered structure 26 after the initial extension limit of the straight load bearing filaments 50-56.

As shown in FIG. 28, when the embroidered structure 26 is in its initial relaxed state, the zigzag load bearing filaments 60-62 have slack due to the zigzagged thread path. When the embroidered structure 26 is stretched under a repeated load, the zigzag load bearing filaments 60-62 straighten, as shown in FIG. 29. In this way, zigzag load bearing filaments 60-62 are permanently fixated, thereby limiting the overall extension of the embroidered structure 26. The two sets of load bearing filaments (i.e. straight load bearing filaments 50-56 and zigzag load bearing filaments 60-62) together create a bi-modic tension feature in the embroidered structure 26 to limit stretch/extension across the affected joint or intervertebral disc space and give the embroidered structure 26 residual stretch/variable extension over time. The overall residual stretch property of the embroidered structure 26 is produced when the zigzag load bearing filaments 60-62 straighten out after the straight load bearing filaments 50-56 have reached their full extension.

It will be appreciated that the number, placement, and positioning of the straight load bearing filaments 50-56 and zigzag load bearing filaments 60-62 within the embroidered structure 26 are set forth by way of example only, and may be varied without departing from the scope of the present invention. Although shown as having a generally trapezoidal shape, embroidered structure 26 may take on any suitable shape including but not limited to rectangular, circular, oval, square, or polygonal. It is also contemplated that the number, shape, and placement of apertures 80-88 and aperture reinforcement filaments 70-78 are set forth by way of example only, and may be varied without departing from the scope of the present invention. In all cases, the bi-modic tension feature of the embroidered structure 26 provides two limits on stretch/extension across an affected joint or intervertebral disc space.

It will be understood that although shown and described as a bi-modic tension feature with two limits on stretch/extension, any number of limits on stretch/extension may be created on an embroidered structure 26 (e.g. tri-modic tension feature, quad-modic tension feature, etc.) via any number of different sets of zigzag load bearing filaments 60-62 and/or straight load bearing filaments 50-56. By having multiple sets of different zigzag (or straight) load bearing filaments with varying patterns, a more complex stretch pattern, such as a step-like feature, may be achieved on the embroidered structure 26. In this way, as each set of zigzag load bearing filaments reaches its full extension limit, another set of zigzag load bearing filaments will then straighten out and impart another limit on the overall stretch/extension of the embroidered structure 26.

Although shown and described in FIGS. 28 & 29, as creating a bi-modic tension feature in an embroidered structure 26 through the use of a combination of straight and zigzag load bearing filaments 50-56 and 60-62, a variety of techniques may be used to achieve the effect of a multi-modic tension feature. By way of example only, as shown in FIGS. 30-35, thread paths 112 of long stitches 114 and thread paths 116 of short stitches 118 may be used to create the effect of a multi-modic tension feature in an embroidered structure 110, according to a second embodiment of the present invention.

Figure 30:
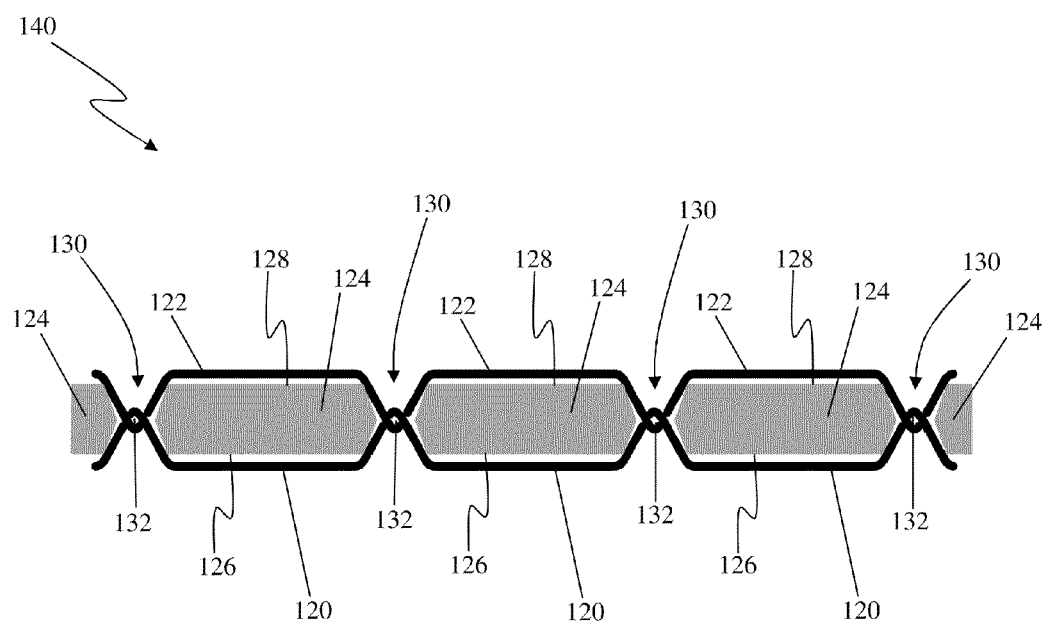
FIG. 30 is a side cross-sectional view of a backing thread and a corresponding stitching thread stitched together on a dissolvable substrate, forming a thread pair with lock stitches, according to another embodiment of the present invention.

FIG. 30 illustrates a backing thread 120 and a stitching thread 122 stitched together on a dissolvable substrate 124. The threads 120, 122 may be formed from any suitable material for creating an embroidered structure, including but not limited to polyester, polypropylene, polyethylene, ultra high molecular weight polyethylene (UHMWPe), carbon fiber, glass, glass fiber, polyaramide, metal, copolymers, polyketones, polyetheretherketone (PEEK), PEEK fiber, polyetherketoneketone (PEKK), polylactic acid, polyglycolic acid, biodegradable fibers, silk, cellulosic and polycaprolactone, including mixtures of one or more of these materials including fibers made therefrom. The dissolvable substrate 124 may be formed from acetate or any other material suitable for use as a dissolvable embroidery substrate. Dissolvable substrate materials are chosen such that the dissolution process or processes used to remove the dissolvable substrate 124 will have minimal effects on the physical properties of the materials of the embroidered structure which are designed to remain after dissolution.

For each backing thread 120 on the backing surface 126 of the dissolvable substrate 124, there is a corresponding stitching thread 122 on the stitching surface 128 of the dissolvable substrate 124. The stitching thread 122 from the stitching surface 128 is passed through openings 130 created in the substrate 124 by the passing of each individual stitching thread 122 to the backing surface 126. Each stitching thread 122 is then looped over its corresponding backing thread 120, forming a lock stitch 132. Once each stitching thread 122 has formed a lock stitch 132 with its corresponding backing thread 120, the stitching thread 122 is passed from the backing surface 126 to the stitching surface 128 through the openings 130 in the substrate 124 created by the passing of the stitching thread 122 to the backing surface 126. The lock stitches 132 prevent the stitching thread 122 from completely pulling back out of the openings 130 created in the substrate 124. The stitching thread 122 is then moved to a new stitching site and the process repeats until each backing thread 120 is joined by lock stitches 132 to its corresponding stitching thread 122, creating a thread pair 140 of some desired length.

Figure 31:
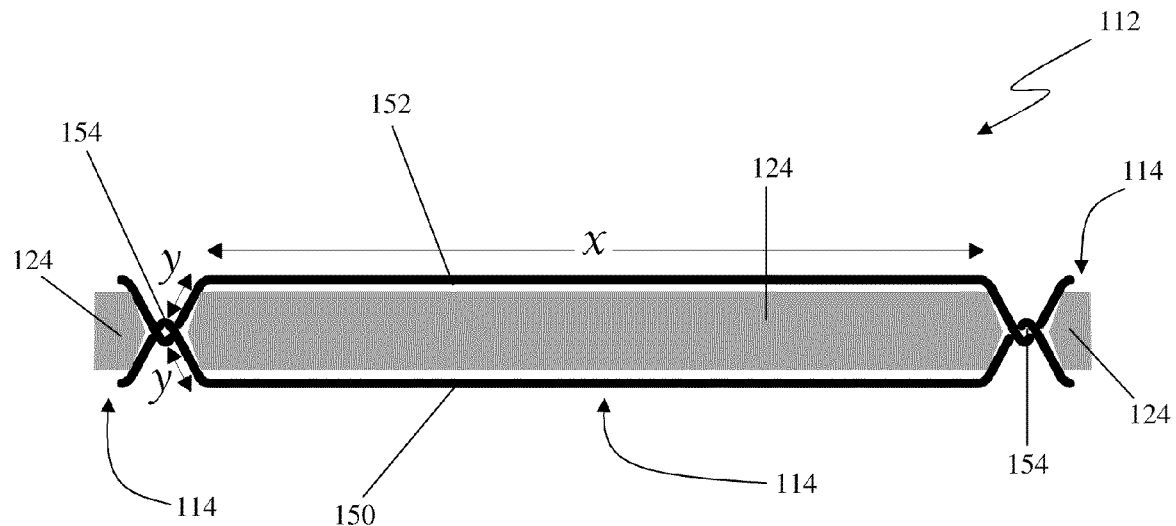
FIG. 31 is a side cross-sectional view of a thread pair having a long stitching path to create long stitches.
Figure 32:
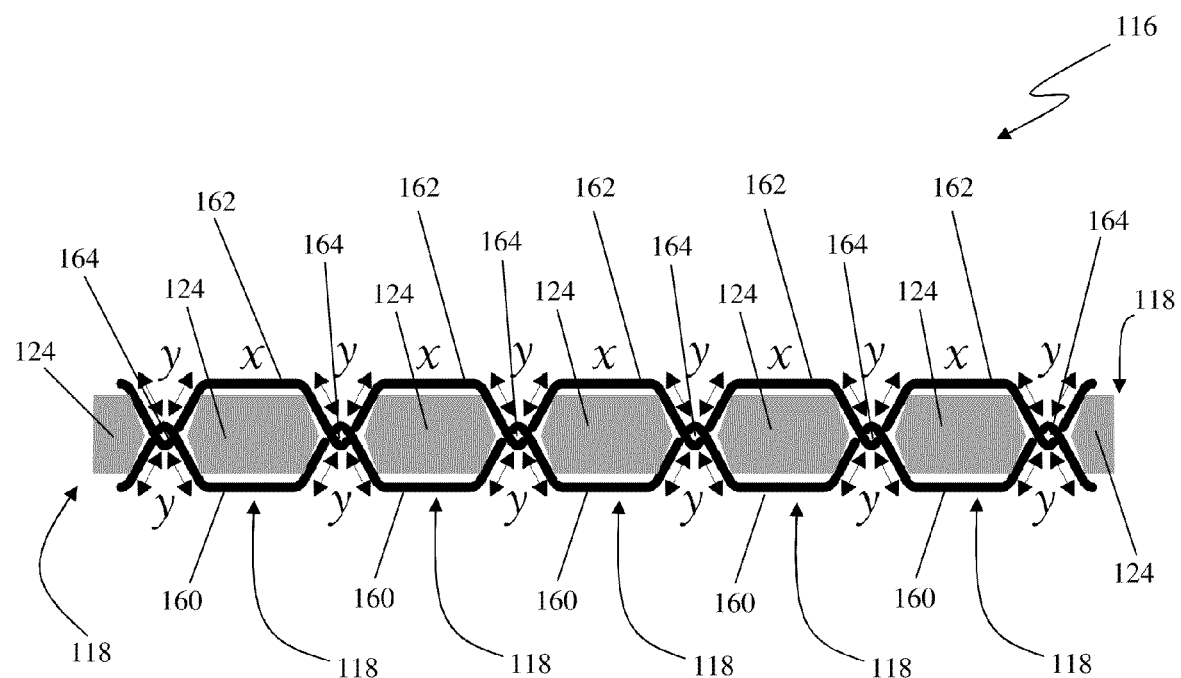
FIG. 32 is a side cross-sectional view of a thread pair having a short stitching path to create short stitches.

By way of example only, FIG. 31 illustrates a thread pair 112 having a long stitching path 114, and FIG. 32 illustrates a thread pair 116 having a short stitching path 118. More specifically, the length of the x-components of the backing and stitching threads 150, 152 between each lock stitch 154 in FIG. 31, is longer than the length of the x-components of the backing and stitching threads 160, 162 between each lock stitch 164 in FIG. 32. By extending the length of the x-component between lock stitches 154 in the thread pair of FIG. 31, long stitches 114 are created. By shortening the length of the x-component between lock stitches 164 in the thread pair of FIG. 32, short stitches 118 are created.

Furthermore, thread pair 112 with long stitches 114 has less residual stretch compared to thread pair 116 with short stitches 118. When the substrate 124 is removed through dissolution, the thread pairs 112, 116 have slack or extra thread length due to the y-components of the backing and stitching threads 150-152, 160-162 near the lock stitches 154, 164. In this way, when the thread pairs 112, 116 are stretched out, the extra length due to the y-components of the threads 150-152, 160-162 add to the overall length of the x-components of the thread pairs 112, 116.

By way of example only, thread pair 112 with long stitches 114 has long x-components and minimal y-components in between each lock stitch 154. As follows, when the thread path 112 with long stitches 114 stretches out, the minimal y-components in between each of the long stitches 114 minimally add to the overall length of the x-component of the long-stitched thread pair 112. In this way, a long-stitched thread path 112 has minimal residual stretch.

By way of example only, thread pair 116 with short stitches 118 has short x-components and maximal y-components in between each lock stitch 164. As follows, when the thread path 116 with short stitches 118 stretches out, the maximal y-components in between each of the short stitches 114 greatly add to the overall length of the x-component of the short-stitched thread pair 116. In this way, a short-stitched thread path 116 has maximal residual stretch.

This property of adding extra thread length and creating residual stretch may be advantageously employed to give variable extension to any thread pair 140, 112, 116 and embroidered structure 10, 110. For example, long-stitched thread paths 112 with minimal residual stretch may be used in an embroidered structure 110 to create an initial limit to the extension of the embroidered structure 110 under a load. Over time with repeated loading of the embroidered structure 110, the long-stitched thread paths 112 may stretch out. At this point, short-stitched thread paths 116 with maximal residual stretch may then act as a second limit on the extension of the embroidered structure 110. The two sets of thread paths (i.e. long-stitched thread paths 112 and short-stitched thread paths 116) together create the bi-modic tension feature in the embroidered structure 110 to limit stretch/extension across an affected joint and give the embroidered structure 110 residual stretch/variable extension over time.

Figure 33:
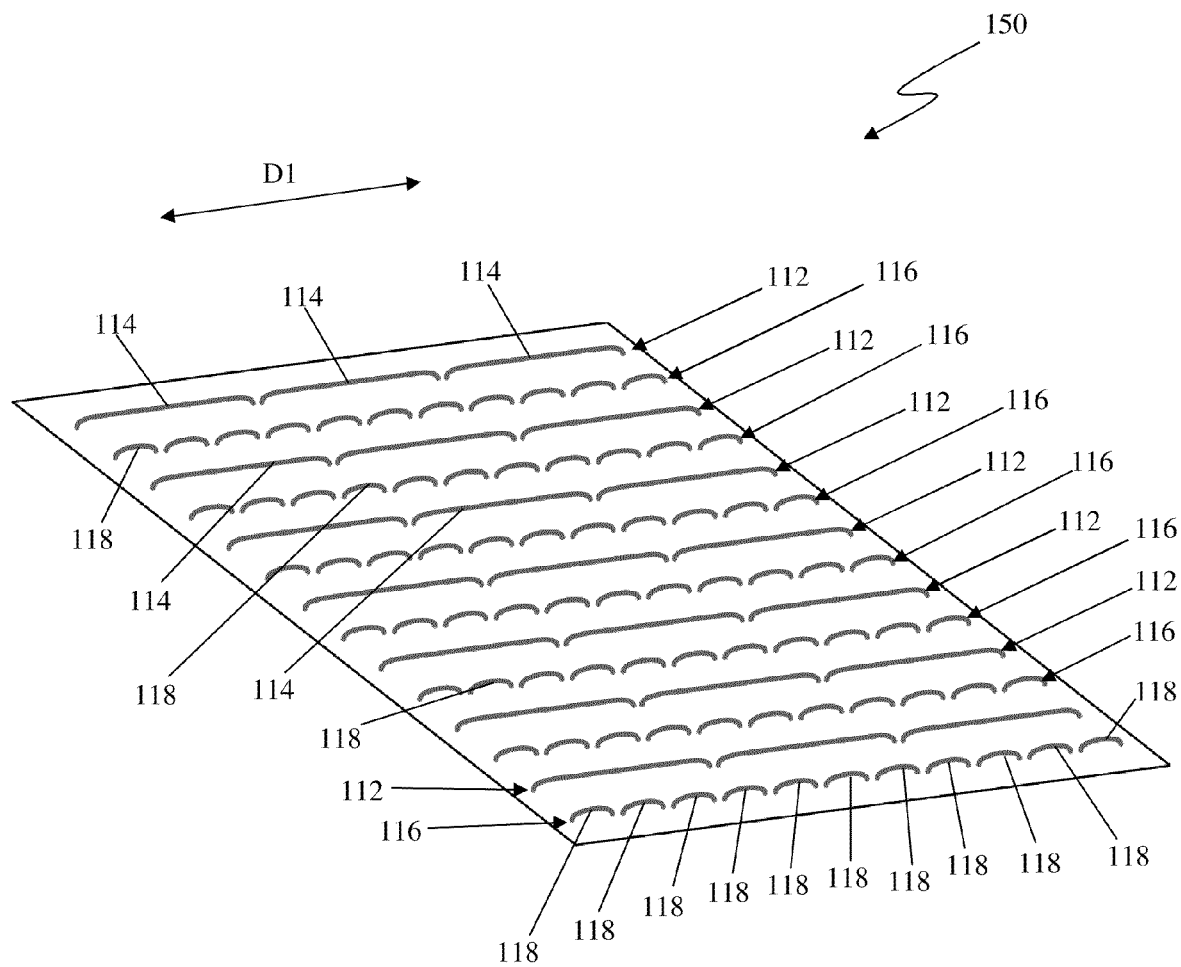
FIG. 33 is a perspective view of an embroidered base layer comprised of alternating long-stitched thread paths and short-stitched thread paths aligned in one direction.

By way of example only, FIG. 33 illustrates an embroidered layer 150 comprised of alternating long-stitched thread paths 112 and short stitched thread paths 116. The long-stitched thread paths 112 provide the embroidered layer 150 with minimal residual stretch, while the short-stitched thread paths 116 provide the embroidered layer 150 with maximal residual stretch. Together, the long-stitched thread paths 112 and short-stitched thread paths 116 provide the embroidered layer 150 with two limits on stretch/extension.

Thread paths 112 with long stitches 114 create a first limit to the extension of the embroidered layer 150 under a load. The long-stitched thread paths 112 may provide initial stability and limit the extension of the embroidered layer 150 through the inherent minimal residual stretch property of thread paths 112 with long stitches 114. Over time with repeated loading of the embroidered layer 150, the long-stitched thread paths 112 may stretch out. At this point, the thread paths 116 with short stitches 118 may then act as a second limit on the extension of the embroidered layer 150. Due to the inherent maximal residual stretch property of thread paths 116 with short stitches 118, short-stitched thread paths 116 have the capacity to further limit the extension of the embroidered layer 150, after the initial extension limit of the long-stitched thread paths 112. The alternating long-stitched thread paths 112 and short-stitched thread paths 114 together create a bi-modic tension feature in the embroidered layer 150 to limit stretch/extension and impart residual stretch/variable extension over time. The overall residual stretch property of the embroidered structure 110 is produced when the short-stitched thread paths 116 straighten out after the long-stitched thread paths 112 have reached their full extension.

Figure 34:
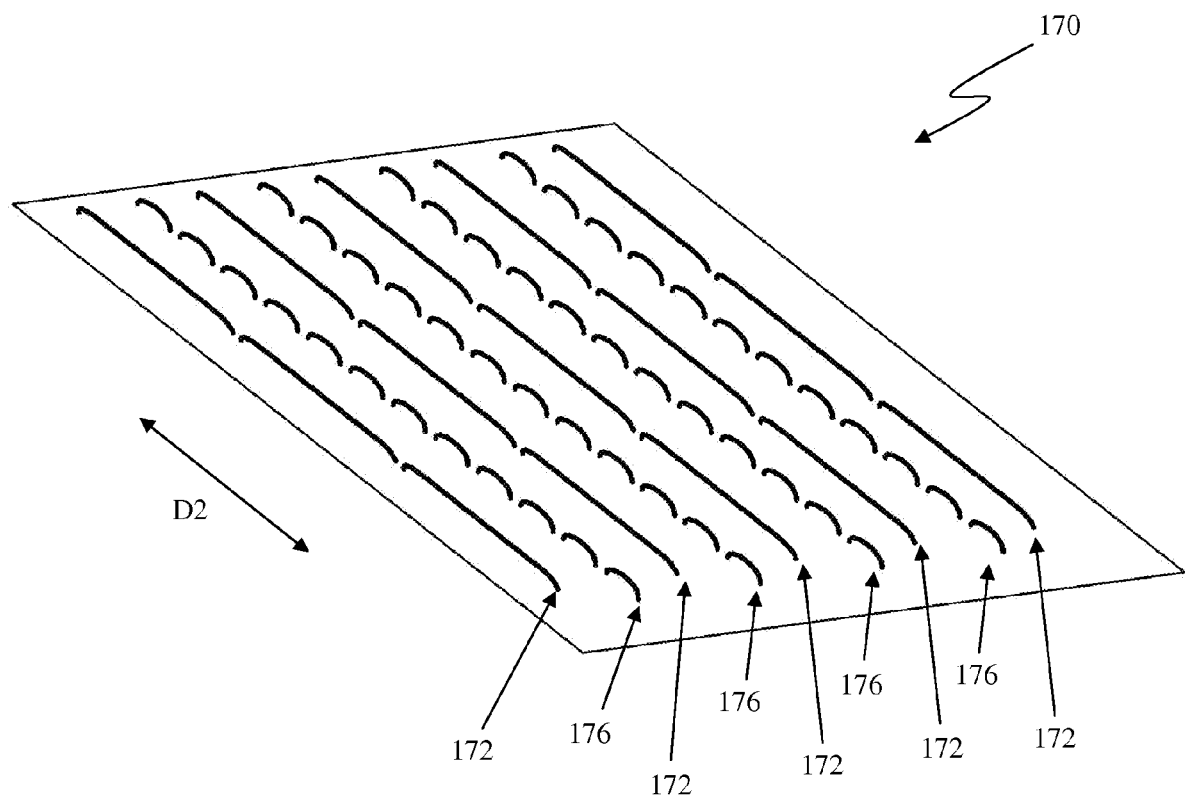
FIG. 34 is a perspective view of an embroidered enclosing layer comprised of alternating long-stitched thread paths and short-stitched thread paths aligned in a direction orthogonal to the thread paths of the embroidered layer of FIG. 33.
Figure 35:
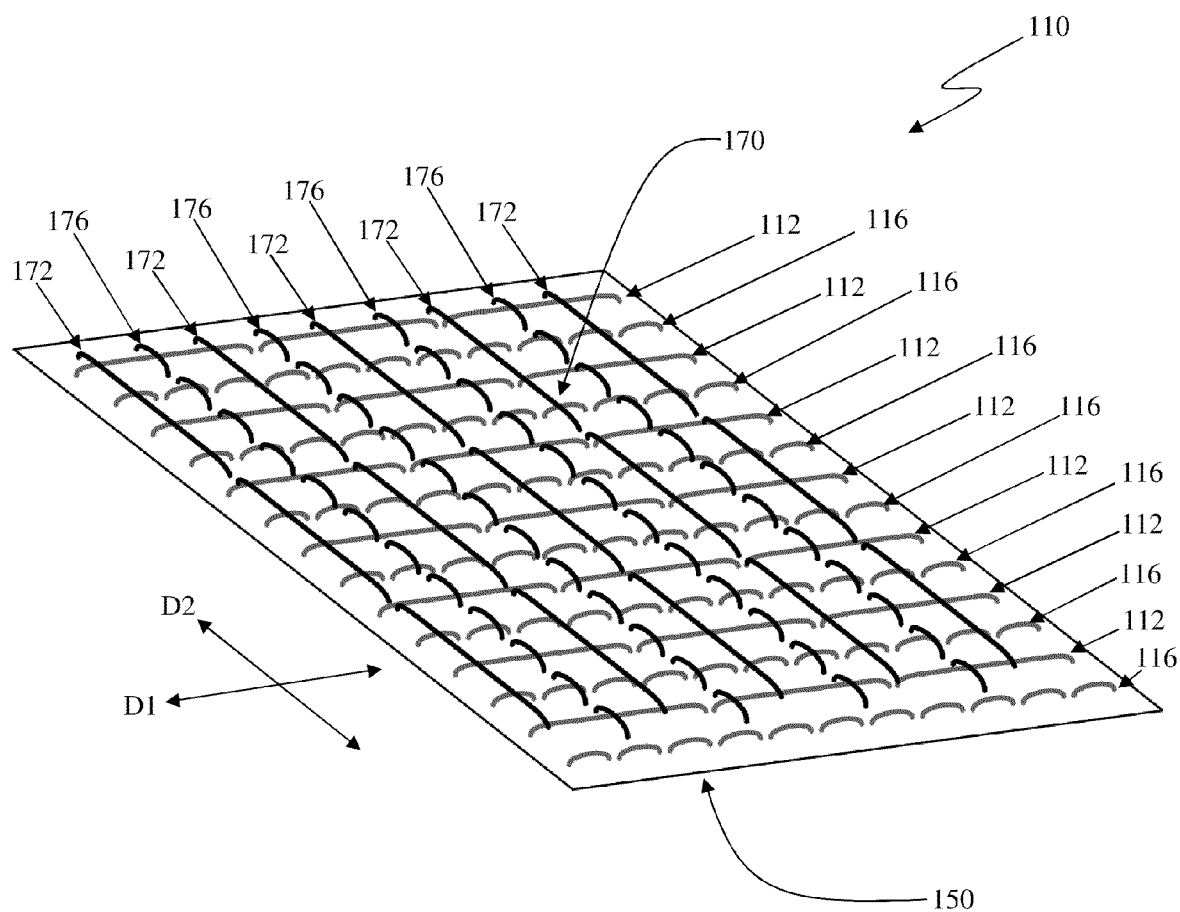
FIG. 35 is a perspective view of an embroidered structure comprised of the enclosing layer of FIG. 34 superimposed over the base layer of FIG. 33.

By way of example only, an embroidered structure 110 may be comprised of a base layer 150 and an enclosing layer 170. As shown in FIG. 33, base layer 150 may be comprised of alternating long-stitched thread pairs 112 and short-stitched thread pairs 116 aligned in a first direction D1. As shown in FIG. 34, enclosing layer 170 may be comprised of long-stitched thread pairs 172 and short-stitched thread pairs 176, aligned in a second direction D2. As shown in FIG. 35, embroidered structure 110 is created by superimposing (or overstitching) one layer 170 of alternating long-stitched and short-stitched thread pairs 172, 176 over another layer 150 of alternating long-stitched and short-stitched thread pairs 112, 116. The thread pairs 172, 176 of enclosing layer 170 are orthogonal to the thread pairs 112, 116 of base layer 150.

Due to the long-stitched thread pairs 112, 172 and the short-stitched thread pairs 116, 176 of layers 150, 170, embroidered structure 110 includes a bi-modic tension feature to limit stretch/extension in two directions D1, D2. By way of example only, embroidered structure 110 may be used in multiple layers to build a solid textile core of an intervertebral disc implant (not shown). When used to build a textile core, a stack of layers comprised of embroidered structure 110 may advantageously impart an enhanced directional stability throughout the entire core because embroidered structure 110 has two limits on stretch/extension in two directions D1, D2.

It will be appreciated that the alternating pattern of long-stitched thread pairs 112, 172 and short-stitched thread pairs 116, 176 in layers 150, 170 is set forth by way of example only, and that the stitch pattern and layout of thread pairs 112, 116, 172, 176 in embroidered structure 110 may change without departing from the scope of the present invention. The number of layers 150, 170 used to create the embroidered structure 110 is also set forth by way of example only and may be increased or decreased. Although described herein as achieving a bi-modic tension feature through different stitch lengths, a variety of techniques may be used to create a bi-modic tension feature, including but not limited to the use of a thicker backing fabric or substrate 124. The bi-modic tension feature is not limited to spinal surgery or the applications disclosed herein, but may be used in a variety of applications.

It will be understood that although shown and described herein as a bi-modic tension feature with two limits on stretch/extension, any number of limits on stretch/extension may be created on an embroidered structure 110 (e.g. tri-modic tension feature, quad-modic tension feature, etc.) via any number of sets of thread paths with varying stitch lengths. By having multiple sets of different thread paths with varying stitch lengths, a more complex stretch pattern (such as a step-like feature) may be achieved on the embroidered structure 110. In this way, as each set of thread paths with a predetermined stitch length reaches its full extension limit, another set of thread paths with a different predetermined stitch length will then straighten out, imparting another limit on the overall stretch/extension of the embroidered structure 110. In addition, a combination of the various techniques used to create the bi-modic tension feature (e.g. zigzag load bearing filaments and thread paths with varying stitch lengths)

may be utilized on the same embroidered structure 110 to impart a complex stretch pattern.

Figure 36:
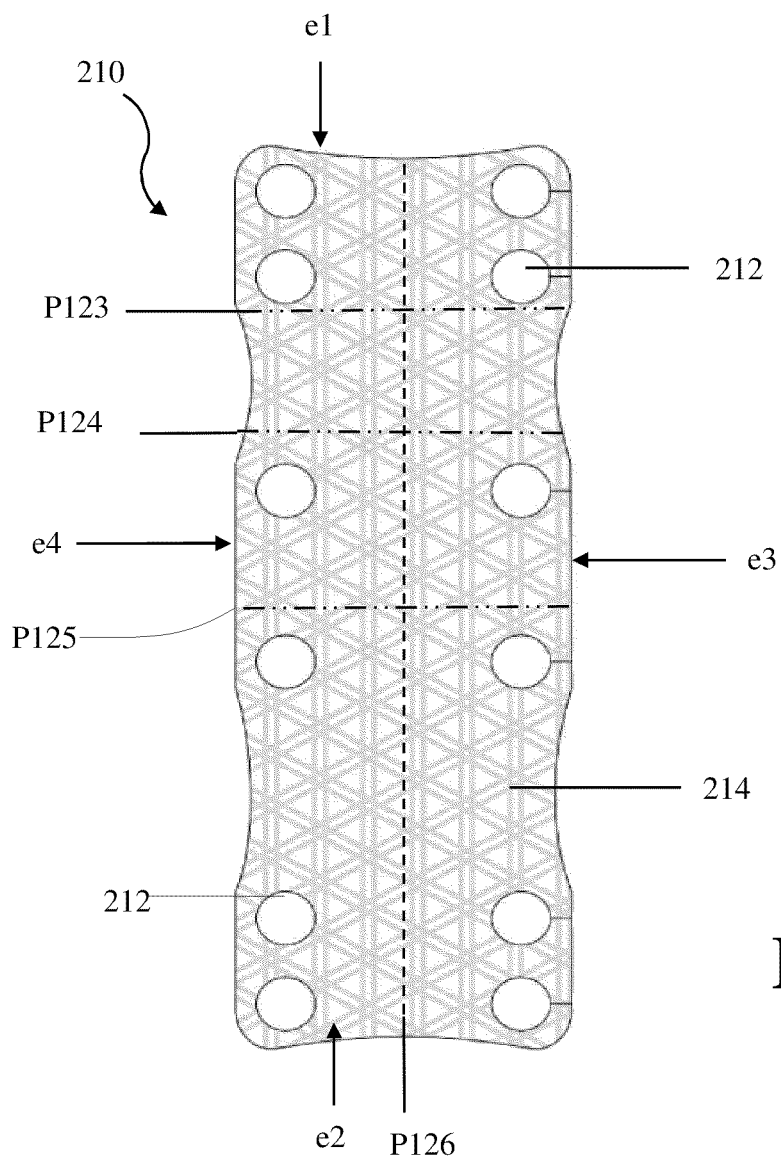
FIG. 36 is a perspective view of one example of a customizable plate according to one embodiment of the present invention.
Figure 37:
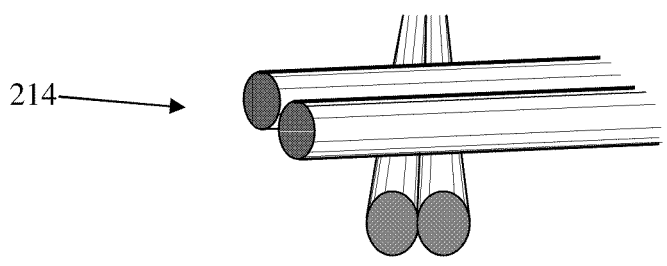
FIG. 37 is a perspective view of the filaments comprising the customizable plate of FIG. 36.

FIGS. 36 and 37 illustrate an example of a customizable textile-based plate 210 according to one embodiment of the present invention. The customizable textile-based plate 210 described herein is dimensioned for implantation into anterior, posterior and lateral aspects of the cervical, lumbar and thoracic regions of the spine. In the present example the generally planar plate 210 comprises a textile-based fabric 214 configured rectilinearly with first e1 and a second sides e2 both shorter than third e3 and fourth sides e4. The plate 210 includes six anchor receiving apertures 212 aligned with the third side e3 and six anchor receiving apertures 212 aligned with the fourth side e4.

As shown in FIGS. 36 and 37, the plate 210 comprises textile filaments 214 extending through and comprising the plate 210 matrix. Orientation of the textile filaments 214 in this manner provides optimal load sharing characteristics across the entire plate 210 matrix while concurrently affording the ability to confine targeted implants within their intended positions. Filament 214 composition, shape, diameter and number within the plate 210 determine plate flexibility. Provision of a plate 210 comprising a multitude of filaments 214 also provides a clinician with the ability to excise portions of the plate without compromising the load bearing and restrictive utility of the resulting customized plate 210.

Properly positioned, the plate 210 may affix adjacent tissues through the application of anchoring elements inserted through the anchor receiving apertures 212 and into receiving tissue(s). The anchor receiving apertures 212 may be of any shape and size which might advantageously allow for preferential seating of anchorage elements including but not limited to ovoid, rectangular, rhomboid or other like shapes. Although the present embodiment illustrates a plate 210 configured with twelve anchor receiving apertures 212, it can be appreciated that any number of anchor receiving apertures 212 may be included within the plate 210 matrix in any number of configurations which might align with intended appliances or target tissues.

In order to attain preferential plate 210 implantation, it may become necessary to adjust plate 210 configuration and\or size. Plate 210 customization may be achieved through excision of and/or cutting through a plate 210 section. As illustrated in FIG. 36 for example only, inclusion of multiple anchor receiving apertures 212 throughout the plate affords technicians the ability to excise plate 210 sections which include apertures, either pre or intra-operatively, while retaining a sufficient number of anchor receiving apertures 212 to preferentially secure the plate 210 in a targeted position. More specifically, as exhibited in FIG. 36, portions of the plate 210 may be excised by cutting across the plate 210 matrix at points including but not limited to P123-P126 ultimately yielding a preferentially sized plate 210 configured with anchor receiving apertures 212 advantageously aligned with the receiving tissue(s).

Figure 40:
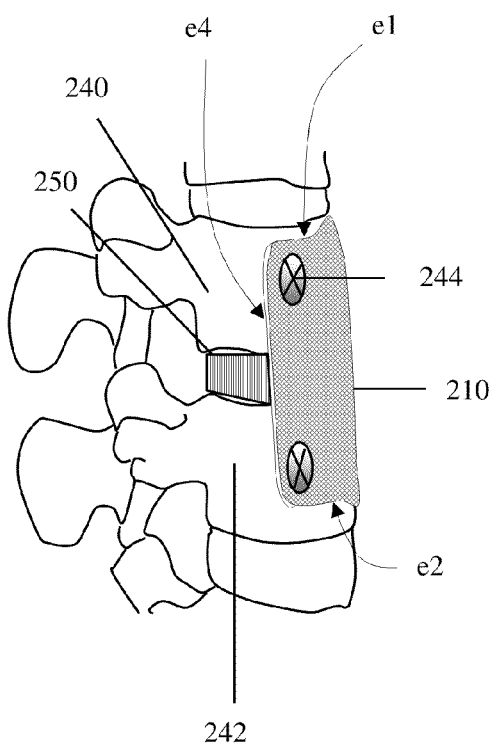
FIG. 40 is a lateral view of adjacent vertebrae with a customizable plate of FIG. 39 attached thereto and used in conjunction with a prosthetic vertebral disc.

As indicated in FIG. 36, the present embodiment includes contoured long and short sides e1-e4. Each side e1, e2, e3, e4 may be contoured to conform to specific tissue structures or therapeutic appliances to afford optimal positioning of the device within the intended interstitial attachment site. In the present example, the short sides e1, e2 are curvilinearly configured to encourage full engagement of the plate 210 to a cylindrically shaped surface such as a vertebral body 240, 242 (FIG. 40). Although shown in the present embodiment as a rectilinear form with curvilinear segments, it can be appreciated that segments of plate sides each may each comprise any suitable shape including but not limited to ovoid, square, rhomboid the like which might facilitate preferential plate 210 insertion and fixation.

Fixation of the plate 210 to receiving tissues may be achieved by inserting anchoring elements 244 (FIGS. 39-42) through the fixation apertures 212 and into the targeted receiving tissue(s) 240, 242 (FIGS. 39-42). Any suitable anchoring device 244 capable of maintaining plate 210 positioning and transferring plate 210 loads including but not limited to screws, nails, adhesives, sutures, wire, crimps and the like may be used to preferentially affix the plate 210. Furthermore, the anchoring elements may comprise any material suitable to achieve fixation while promoting load transference into receiving tissues 240, 242 including but not limited to bone, bio-resorbing material, metal, plastic, PEEK, PEKK, bone cement, synthetic composites and the like. Once properly attached, the plate 210 of the current embodiment limits extension of the spanned joint while selectively retaining flexional and torsional mobility of the same as dictated by the above mentioned filament 214 and plate 210 configurations.

Figure 38:
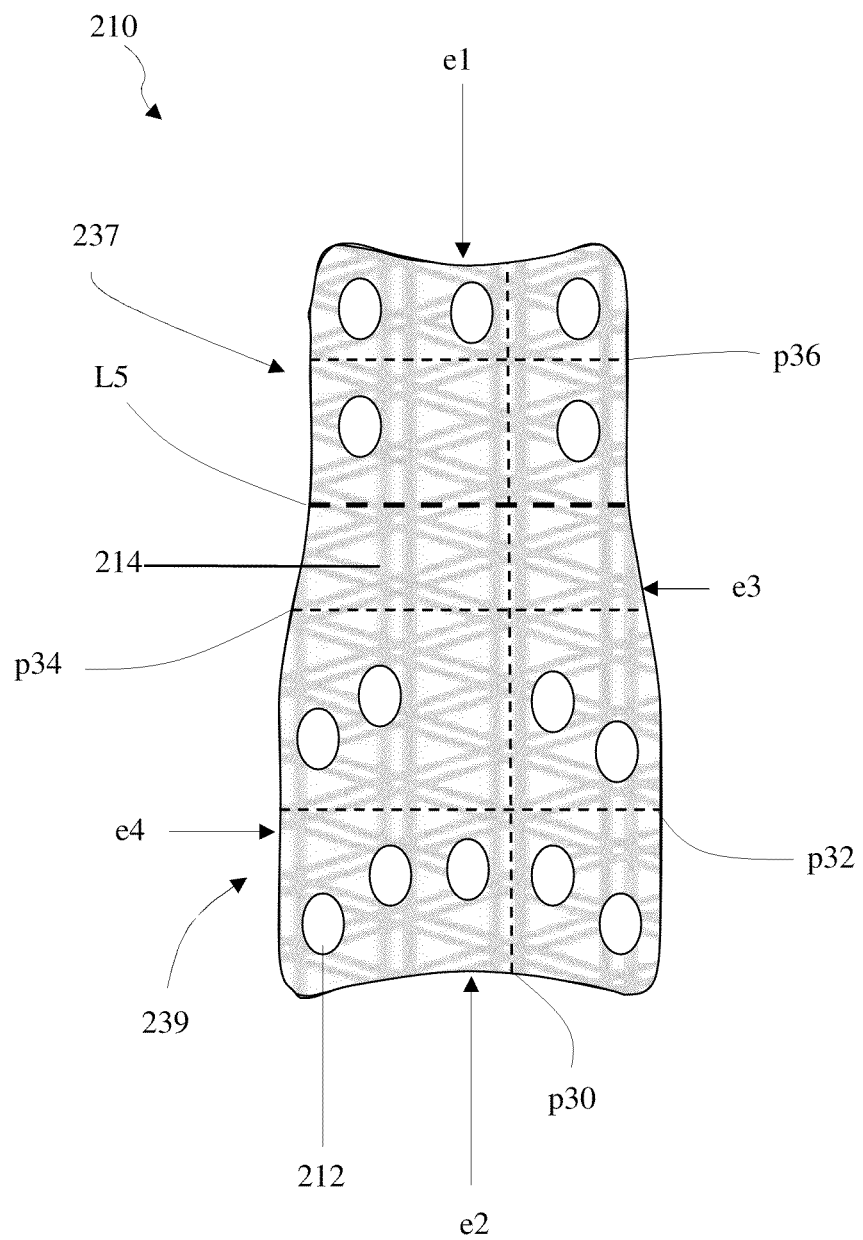
FIG. 38 is a perspective side view of another example of a customizable plate according to one embodiment of the present invention.

FIG. 38 illustrates a second example of a customizable textile-based plate of the present invention configured for implantation into anterior, posterior and lateral aspects of the cervical, lumbar and thoracic regions of the spine. The current example comprises a generally planar textile based plate 210 with generally curvilinear a first side e1 shorter than a second side e2 both shorter than generally curvilinear third and fourth sides e3, e4 thus resulting in a plate 210 with a first end 237 (between point L5 and side e1) narrower than a second end 239 (between point L5 and side e2). As with the first described embodiment, the plate sides e1, e2, e3, e4 may be provided in any number of shapes including but not limited to curved, linear, squared, angled and the like to provide for preferential in situ plate seating as demanded by the physiological structure of the implant receiving tissues.

The plate's first end 237 comprises a first pair of anchoring apertures 212 aligned proximate to the fourth plate side e4 and a pair of anchoring apertures 212 aligned with the plate's third side e3 and a single aperture 212e aligned with the longitudinal midline of the plate 210. Additionally, the second plate end 239 comprises a first set of four apertures 212 aligned with the fourth plate side e4 and an additional set of four apertures 212 aligned with the third plate side e3, and a single aperture 212 aligned with the longitudinal midline of the plate 210. Provided with fourteen apertures in the above described configuration, the plate 210 provides a clinician with the opportunity to excise portions of the plate so that the resulting customized plate 210 can meet the demands presented by the physiological demands of a given implantation site.

To achieve preferred customization of the plate 210, the clinician may choose to cut through any number of plate surfaces along paths including but not limited to p30, p32, p34, p36 to achieve the desired plate 210 functionality. Furthermore, although described as excising portions of a plate, it can be appreciated by one skilled in the art that customization of the plate might also be achieved by merely cutting the plate matrix without excision of a plate 210 section.

The plate 210, as provided in the present embodiment and compared to the first embodiment, illustrates that an implant comprising any number of apertures 212 disposed in a variety of patterns within a variety of plate matrix configurations would be recognized by one skilled in the art as falling within the scope of the present invention.

Figure 39:
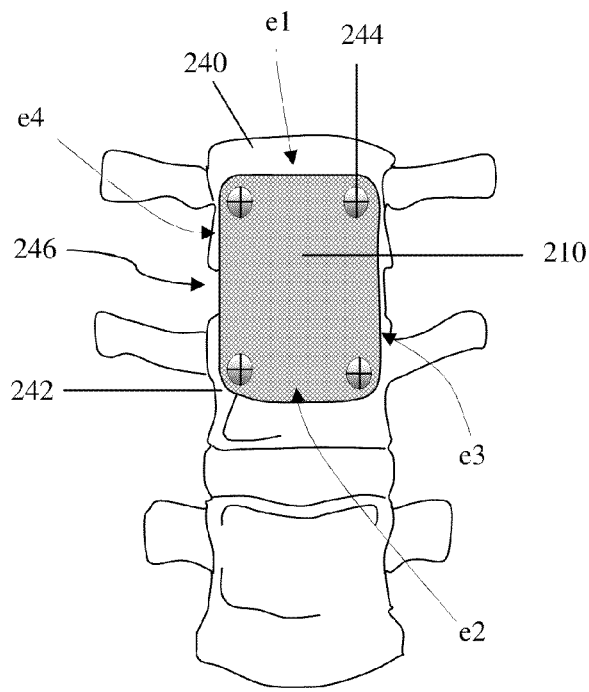
FIG. 39 is a view of adjacent anterior vertebral surfaces with a customizable plate according to another embodiment of the present invention affixed thereto.

FIG. 39 illustrates an example of the customizable plate 210 affixed to anterior tissues 240, 242 adjacent to an affected vertebral joint. The plate 210, as shown, illustrates a preferred implant after customization of a plate 210 such as, for example only, the embodiment illustrated in FIG. 38. The current therapeutic demands of the implantation site illustrated in FIG. 39 may require application of a textile based plate 210 with first and second sides e1, e2 of similar length to third and fourth sides e3, e4, and four anchoring apertures 212, one each included within the matrix proximate to a plate 210 corner. As shown, upon completing customization of the plate 210, screws 244 inserted through the apertures and into receiving tissues 240, 242 adjacent to the affected joint affix the implant to a targeted implantation site.

In the present example, the customized plate configuration reflects the demands of the desired joint spanning utility of the plate 210, and therefore provides a minimally invasive implant dimensioned to span the affected vertebral joint to at least partially immobilize the joint. Customization in this manner ultimately provides a minimally invasive implant which can achieve a desired therapeutic outcome, without the need for access to an extensive inventory of devices configured pre-operatively.

It can be appreciated that the present invention may be used in conjunction with complementary devices to achieve desired therapeutic outcomes for affected tissues. Thus, FIG. 40 illustrates a fourth embodiment of the present invention, excised from, for example only, a plate configured similarly to the embodiment of FIG. 36. The customized plate 210 of the present embodiment is shown fixed to anterior vertebral surfaces and restricting a fusion promoting disc implant 250 within an affected joint. Utilized in the current application, the plate 210 advantageously detains the disc implant 250 between adjacent vertebral bodies 240, 242 while simultaneously limiting extension across the affected joint.

To achieve the above described utility, the customized plate 210 of the current embodiment comprises first and second plate sides e1, e2 of similar length to third e3 and fourth (not shown) plate sides. Additionally, the resulting plate 210, for example only, comprises a textile based matrix including four anchoring apertures 212, one each positioned proximate to a plate corner. Fixation of the plate 210 to the tissues 240, 242 is achieved through the insertion of screws through the apertures 212 and into the receiving tissues 240, 242. As shown, the customized plate 210 provides a minimally invasive implant of sufficient length to span the affected joint, while also providing sufficient fixation apertures 212 with which to preferentially affix the plate 210 to receiving tissues and support plate 210 loads.

The first and second plate sides of the present embodiment are dimensioned to provide a plate of sufficient width so as to restrict the complimentary implant 250 within the affected joint, while the plate's third e3 and fourth e4 sides are dimensioned to optimally orient fixation apertures with the tissues targeted to receive the anchoring elements 244. To achieve the aforementioned preferential plate 210 configuration, a surgeon may excise portions of a plate 210 similar to the embodiment illustrated in FIG. 36.

Figure 41:
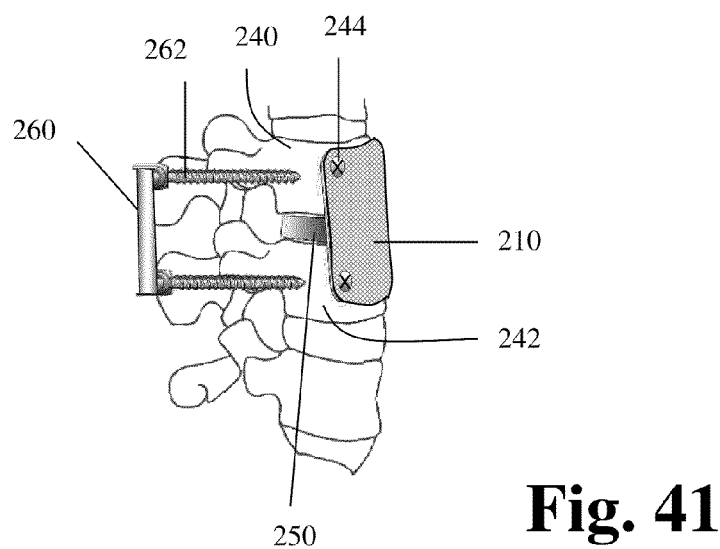
FIG. 41 is a lateral view of adjacent vertebrae with a customizable plate of FIG. 39 attached thereto and used in conjunction with a rod and screw assembly.

FIG. 41 shows another example of the customizable plate 210 of the present invention comprising a configuration similar to that shown in FIG. 39 used in conjunction with a rod 260 and screw 262 assembly. In the current iteration, immobilization of the affected vertebral joint is effected through application of a rod 260 and screw 262 assembly where bone screws 262 have been inserted posteriorly into the pedicles of adjacent vertebrae 240, 242, and joined with a rod attached to and extending between both screw 262 heads. A plate 210 of the present invention spans the anterior aspect of the disc space 246 and is affixed to the adjacent anterior vertebral body surfaces 240, 242 with screws 244 inserted through the anchor receiving apertures 212 and into receiving tissues 240, 242. As shown in the present iteration, the plate 210 detains the disc space insert 250 within the disc space 246 while complementing the immobilizing effect of the attached rod 260 and screw 262 assembly.

Figure 42:
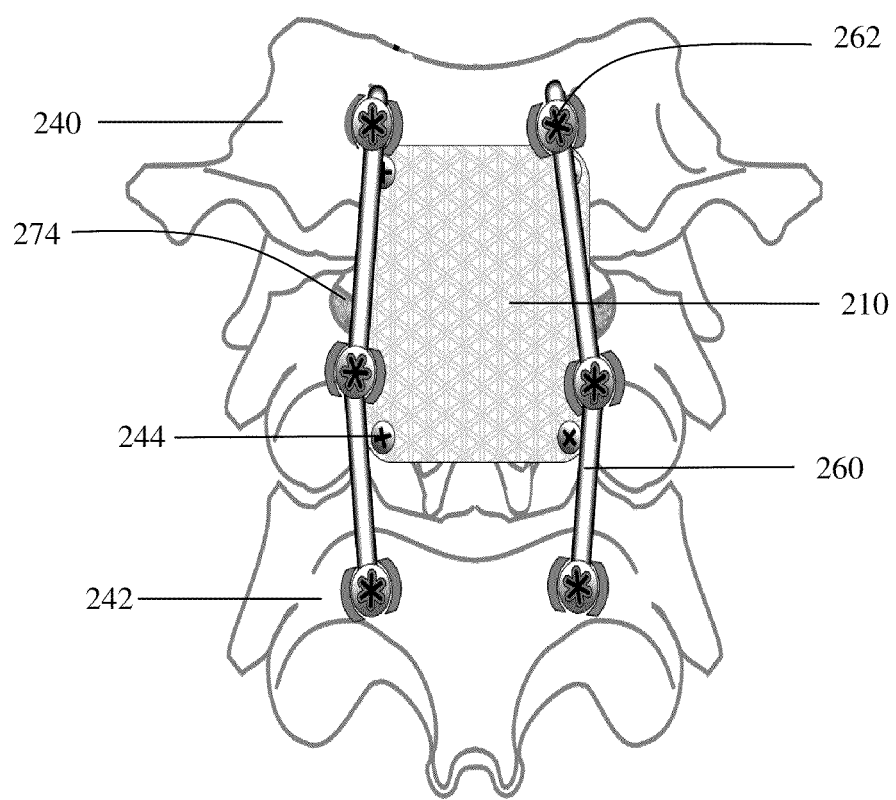
FIG. 42 is a posterior view of a customizable plate of FIG. 39 attached to adjacent vertebrae and used in conjunction with an interspinous process space spacer and rod and screw assembly.

FIG. 42 illustrates an additional example of the customizable plate 210 of the present invention showing a customized plate affixed to posterior aspects of adjacent vertebrae 240, 242 and used in conjunction with a posteriorly applied rod 260 and screw 262 assembly comprising four rods 260 attached to six screws 262. In the current application, the plate 210 is configured to detain an interspinous process space spacer 274 within an interspinous process space where adjacent interspinous processes have been removed. Although shown in use where adjacent spinous processes have been removed, it can be appreciated that the plate 210 may comprise a sufficient dimension or be customized to accommodate the presence of physiological structures including spinous processes. Therefore it can be appreciated that a plate may be customized to include apertures (not shown) through which physiological structures such as, for example only, spinous processes might intrude. As illustrated, the present embodiment of the invention restricts the interspinous process implant 274 within the interspinous process space while complementing the joint immobilizing effects of the rod 260 and screw 262 assembly.

To achieve the above stated utility, the clinician may choose to customize a plate 210 of dimensions similar to, for example only, the embodiment of FIG. 38. Once selected, the clinician can customize the plate 210 to provide a resulting appliance 210 which addresses the needs presented by the implantation site and the utility of the cooperative complimentary appliances. Therefore, the clinician may excise or cut portions of a plate 210 to result in the rectilinear form of the current customized embodiment comprising a plate matrix of first and second sides e1, e2 of lengths shorter than third and fourth plate sides e3, e4. The plate matrix of the present embodiment includes four anchoring apertures 212, one each proximate to a plate corner. The above described configuration provides a customized plate which may reside within the rod 260 and screw 262 assembly "foot print." Although described instantly above as comprising four apertures 212, it can be appreciated that apertures 212 may be included within the plate 210 which would align with and allow the screws 262 of the rod and screw assembly to pass therethrough.

It can be appreciated that the flexible nature of the plate 210 matrix described above and in the attached materials may provide for manipulation of the plate 210 into a low profile configuration to effect minimally invasive introduction of the plate 210 to the target implantation site. FIGS. 43-45 exemplify one potential method and device, by example only, for transporting one embodiment of the present invention through and/or around tissue to the targeted site. FIG. 43 shows an implant insertion device 280 comprising a first rod element 282 and a second cannulated rod element 284. The second rod element 284 comprises a cannulation of greater diameter than the outer diameter of the first rod element 282. Moreover the cannulation of the second rod member 284 may comprise a sufficient diameter to allow for the contemporaneous inclusion of both the plate 210 and second rod element 284.

Properly configured, the second rod element 284 extends between a targeted plate 210 implantation site to a extracorporeal position, thereby providing clinicians access to the targeted implantation site. The plate 210 may then be rolled or alternatively configured for insertion into the proximal cannulation aperture 286 of the second rod member 284. The first rod member 282 may then be inserted into the proximal cannulation aperture 286 of the second rod member 284 concurrently coming into contact with the previously inserted plate 210. Application of force to the proximal end 281 of the inserted first rod member 282 contemporaneously results in the application of force to a proximal plate 210 surface. In this manner the first rod member directs the plate 210 to travel distally through the cannulated second rod member 284 and ultimately exit the second rod member 284 through the distal cannulation aperture 285 at the targeted implantation site. Upon arrival at the implantation site, the plate may be preferentially oriented and attached to the targeted implantation site (FIG. 46).

While the present invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the invention is to cover all modifications, equivalents, and alternatives falling within the spirit of the invention as defined herein.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the invention is to cover all modifications, equivalents, and alternatives falling within the scope and spirit of the invention as defined herein. As such, a textile-based plate having any combination of features described in relation to any of the specific examples disclosed herein is within the scope of the present invention. The implant may be provided with any number of anchorage apertures other than the configurations shown without departing from the scope of the present invention. The implant may be formed at least partially from bioresorbable fibers. For example, in some instances it might be beneficial to have certain portions of the implant (if not the entire implant) be resorbed over time. Moreover, although shown and described by way of example as having specific utility in the human spine, it should be understood that the plate of the present invention may be used in relation to any bony structure in any part of the body without departing from the scope of the present invention.

What is claimed is:

1. A textile-based surgical plate comprising:
   a body portion having at least four apertures for receiving fixation elements therethrough, said body portion bounded by first and second opposing ends and first and second opposing sides;
   at least one load bearing filament extending through said body portion along a closed circuitous route and forming the outer periphery of at least four fixation apertures before completing one circuit;
   a plurality of longitudinal support filaments extending from the first opposing end of the body portion to the second opposing end of the body portion, at least a portion of the longitudinal support filaments extending generally parallel to a longitudinal midline of the body portion and maintaining the orientation of the load bearing filament within the body portion by engaging the load bearing filament; and
   a plurality of horizontal support filaments extending from the first opposing side of the body portion to the second opposing side of the body portion, the horizontal support filaments positioned in a non-parallel manner relative to the longitudinal support filaments,
   wherein said closed circuitous route forms a crossing diagonal route between apertures on the first opposing end and apertures on the second opposing end.

2. The textile-based surgical plate of claim 1, wherein said load bearing filament comprises a thread pair including a stitching thread and a backing thread, said stitching thread positioned on a stitching surface and said backing thread positioned on a backing surface.

3. The textile-based surgical plate of claim 1, wherein said horizontal and longitudinal support filaments each comprise a thread pair including a stitching thread and a backing thread, said stitching thread positioned on a stitching surface and said backing thread positioned on a backing surface.

4. The textile-based surgical implant of claim 3, wherein said load bearing filament is positioned between said thread pairs of said horizontal and longitudinal support filaments.

5. The textile-based surgical plate of claim 1, wherein at least one of said load bearing filament, said horizontal support filaments, and said longitudinal support filaments are composed of at least one of polyester fiber, polypropylene, polyethylene, ultra high molecular weight polyethylene (UHMWPe), poly-ether-ether-ketone (PEEK), carbon fiber, glass, glass fiber, polyaramide, metal, copolymers, polyglycolic acid, polylactic acid, biodegradable fibers, silk, cellulosic and polycaprolactone fibers, aramid fibers and alginate fibers.

6. The textile-based surgical plate of claim 1, further comprising:
   an aperture reinforcement filament positioned around each of said apertures, said aperture reinforcement filament defining the shape of said apertures and engaging at least one of said load bearing filament and said horizontal and longitudinal support filaments.

7. The textile-based surgical plate of claim 1, wherein the load bearing filament and horizontal and longitudinal support filaments are composed of at least one of the same and different materials.

8. The textile-based surgical plate of claim 1, wherein said body portion is sufficiently porous to allow for tissue ingrowth within said plate.

9. The textile-based surgical plate of claim 8, wherein said tissue ingrowth comprises at least one of hard and soft bone tissue.

10. The textile-based surgical plate of claim 1, wherein said body portion is densely stitched to prevent tissue ingrowth within said plate.

11. The textile-based surgical plate of claim 1, further comprising a border filament.

* * * * *